US007294472B2

(12) United States Patent
Gilchrist et al.

(10) Patent No.: US 7,294,472 B2
(45) Date of Patent: *Nov. 13, 2007

(54) METHOD FOR IDENTIFYING MODULATORS OF G PROTEIN COUPLED RECEPTOR SIGNALING

(75) Inventors: Annette Gilchrist, Barrington, IL (US); Heidi M. Hamm, Nashville, TN (US)

(73) Assignee: Caden Biosciences, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/411,336

(22) Filed: Apr. 11, 2003

(65) Prior Publication Data

US 2004/0018558 A1 Jan. 29, 2004

Related U.S. Application Data

(63) Continuation-in-part of application No. 09/852,910, filed on May 11, 2001.

(60) Provisional application No. 60/275,472, filed on Mar. 14, 2001.

(51) Int. Cl.
*C40B 20/00* (2006.01)
*C07H 21/04* (2006.01)

(52) U.S. Cl. .................. 435/7.1; 530/327; 530/300; 435/4; 435/DIG. 2; 435/DIG. 14; 435/DIG. 15

(58) Field of Classification Search ............... 435/7.1, 435/4, DIG. 2, DIG. 14, DIG. 15; 530/327, 530/300
See application file for complete search history.

(56) References Cited

U.S. PATENT DOCUMENTS

| | | | |
|---|---|---|---|
| 4,160,452 A | 7/1979 | Theeuwes | |
| 4,256,108 A | 3/1981 | Theeuwes | |
| 4,265,874 A | 5/1981 | Bonsen et al. | |
| 5,034,506 A | 7/1991 | Summerton et al. | |
| 5,733,731 A | 3/1998 | Schatz et al. | |
| 5,880,972 A | 3/1999 | Horlbeck | |
| 5,892,014 A | 4/1999 | Coughlin et al. | |
| 5,955,575 A | 9/1999 | Peri et al. | |
| 6,087,186 A | 7/2000 | Cargill et al. | |
| 6,156,511 A | 12/2000 | Schatz et al. | |
| 6,184,223 B1 | 2/2001 | Kahn et al. | |
| 6,300,312 B1 | 10/2001 | Chemtob et al. | |
| 6,617,114 B1* | 9/2003 | Fowlkes et al. | 435/7.1 |
| 6,864,060 B1* | 3/2005 | Fowlkes et al. | 435/7.1 |
| 6,864,229 B2* | 3/2005 | Kuliopulos et al. | 514/2 |
| 2004/0220198 A1 | 11/2004 | Haldar et al. | |

FOREIGN PATENT DOCUMENTS

WO WO98/19162 A1 5/1998

OTHER PUBLICATIONS

Gates, et al., Affinity Selective Isolation of Ligands from Peptide Libraries Through Display on a lac Repressor "Headpiece Dimer", *J. Mol. Biol.*, 255, 373-386, 1996.
Lewin, B., "G Proteins May Activate or Inhibit Target Proteins," Genes VII, Oxford University Press 2000, Chapter 26, pp. 809-811.
Acharya et al., "Transducin-α C-terminal Peptide Binding site Consists of C-D and E-F Loops of Rhodopsin", J. Biol. Chem., 272(10):6519-6524, 1997.
Adang et al., "The contribution of combinatorial chemistry to lead generation: an interim analysis," Curr. Med. Chem., 8(9):985-998, 2001 (Abstract Only).
Aris et al., "Structural Requirements for the Stabilization of Metarhodopsin II by the C Terminus of the α subunit of Transducin," J. Biol. Chem., 276(4):2333-2339, 2001.
Azpiazu et al., "A G Protein γ Subunit-specific Peptide Inhibits Muscarinic Receptor Signaling," J. Biol. Chem., 274(50):35305-35308, 1999.
Bae et al., "Molecular Determinants of Selectivity in 5-Hydroxytryptamine$_{1B}$ Receptor-G Protein Interactions", J. Biol. Chem., 272(51):32071-32077, 1997.
Bala et al., "Novel peptidomimics as angiotensin-converting enzyme inhibitors: a combinatorial approach," Bioorg. Med. Chem., 10(11):3685-91, 2002 (Abstract Only).
Barker et al., "Constitutively Active 5-Hydroxytryptamine$_{2c}$ Receptors Reveal Novel Inverse Agonist Activitiy of Receptor Ligands", J. Biol. Chem., 269(16):11687-11690, 1994.
Bertin et al., "Functional Expression of the Human Serotonin 5-HT1A Receptor in *Escherichia coli*", J. Biol. Chem., 267(12):8200-8206, 1992.
Blahos et al., "A Novel Site on the Gα-protein That Recognizes Heptahelical Receptors", J. Biol. Chem. 276(5):3262-3269, 2001.
Buck et al., "Role of Dynamic Interactions in Effective Signal Transfer for Gβ Stimulation of Phospholipase C-β2", J. Biol. Chem., 277(51):49707-49715, 2002.
Cheadle et al., "Identification of a Src SH3 Domain Binding Motif by Screening a Random Phage Display Library", J. Biol. Chem., 269(39):24034-24039, 1994.
Chidiac et al., "Inverse Agonist Activity of β-Adrenergic Antagonist", Mol. Pharmacol., 45:490-499, 1994.
Conklin et al., "Carboxyl-Terminal Mutations of $G_{q\alpha}$ and $G_{s\alpha}$ That Alter the Fidelity of Receptor Activation", Mol. Pharmacol., 50:885-890, 1996.
Conklin et al., "Substitution of three amino acids switches receptor specificity of $G_q\alpha$ to that of $G_i\alpha$", Nature, 363:274-276, 1993.
Copeland, Robert A., "Mechanistic considerations in high-throughput screening", Analytical Biochem., 320:1-12, 2003.
Costa and Herz, "Antagonists with negative intrinsic activity at δ opioid receptors coupled to GTP-binding proteins", Proc. Natl. Acad. Sci. USA, 86:7321-7325, 1989.

(Continued)

Primary Examiner—T. D. Wessendorf
(74) Attorney, Agent, or Firm—Rothwell, Figg, Ernst & Manbeck pc

(57) ABSTRACT

This invention relates to methods for identifying peptides and other compounds which block or enhance G protein coupled receptor mediated signaling with high affinity and specificity and/or which stabilize a particular conformer of a G protein coupled receptor. Assays, methods of treatment and other methods developed in conjunction with these methods also are disclosed.

17 Claims, 28 Drawing Sheets

OTHER PUBLICATIONS

Costa et al., "Drug Efficacy at Guanine Nucleotide-Binding Regulatory Protein-Linked Receptors: Thermodynamic Interpretation of Negative Antagonism and of Receptor Activity in the Absence of Ligand", Mol. Pharmacol., 41:549-560, 1992.

Cull et al., "Screening for receptor ligands using large libraries of peptides linked to the C terminus of the *lac* repressor", Proc. Natl. Acad. Sci. USA, 89:1865-1869, 1992..

Cwirla et al., "Peptide Agonist of the Thrombopoietin Receptor as Potent as the Natural Cytokine", Science, 276:1696-1699, 1997.

Dani, Maria, "Peptide Display Libraries: Design and Construction", J. of Receptor & Signal Transduction Research, 21(4):469-488, 2001.

Farfel et al., "The Expanding Spectrum of G Protein Diseases", New Engl. J. Med., 340(13): 1012-1020, 1999.

Flanagan et al., "Advances in understanding gonadotrophin-releasing hormone receptor structure and ligand interactions", Rev. of Reprod., 2:113-120, 1997.

Ford et al., "Molecular Basis for Interactions of G Protein βγ Subunits with Effectors", Science, 280:1271-1274, 1998.

Francken et al., "Human 5-hydroxytryptamine$_{5A}$ Receptors Activate Coexpressed G$_i$ and G$_o$ Proteins in *Spodoptera frugiperda* 9 Cells", Mol. Pharmacol., 57:1034-1044, 2000.

Garcia et al., "Transducin-α C-terminal mutations prevent activation by rhodopsin: a new assay using recombinant proteins expressed in cultured cells", EMBO J., 14(18):4460-4469, 1995.

Gilchrist et al., "Use of Peptides-on-Plasmids Combinatorial Library to Identify High-Affinity Peptides That Bind Rhodopsin", Methods in Enzymology, 315:388-404, 2000.

Gilchrist et al., "Gα COOH-Terminal Minigene Vectors Dissect Heterotrimeric G Protein Signaling", Protocols: Science's STKE, 118, 2002, (Abstract only).

Gilchrist et al., "A Dominant-Negative Strategy for Studying Roles of G Proteins in Vivo", J. of Biol. Chem., 274(10):6610-6616, 1999.

Gilchrist et al., "Antagonists of the Receptor-G Protein Interface Block G$_i$-coupled Signal Transduction", J. Biol. Chem., 273(24):14912-14919, 1998.

Glass et al., Agonist Selective Regulation of G Proteins by Cannabinoid CB$_1$ and CB$_2$ Receptors, Mol. Pharmacol., 56:1362-1369, 1999.

Greco et al. "Cancer Genere Therapy: 'Delivery, Delivery, Delivery'", Frontiers in Bioscience, 7:1516-1524, 2002.

Gromoll et al., "Functional and clinical consequences of mutations in the FSH receptor", Mol. and Cell. Endocrinol., 125:177-182, 1996.

Hall, David A., "Modeling the Functional Effects of Allosteric Modulators at Pharmacological Receptors: An Extension of the Two-State Model of Receptor Activation", Mol. Pharmacol., 58(6):1412-1423, 2000.

Hamm and Gilchrist, "Heterotrimeric G proteins", Current Opinion in Cell Biol., 8:189-196, 1996.

Hamm et al., "Site of G protein binding to rhodopsin mapped with synthetic peptides from the alpha subunit", Science, 241(4867):832-835, 1988. (Abstract only).

Hamm, Heidi E., "The Many Faces of G Protein Signaling," J. of Biol. Chem. 273(2):669-672, 1998.

Hasegawa et al. "Two Isoforms of the Prostaglandin E Receptor EP3 Subtype Different in Agonist-independent Constitutive Activity", J. Biol. Chem., 271(4):1857-1860, 1996.

Inanobe et al., "Molecular cloning and characterization of a novel splicing variant of the Kir3.2 subunit predominantly expressed in mouse testis", J. Physiol., 521.1:19-30,1999.

Kay et al., "Screening Phage-Displayed Combinatorial Peptide Libraries", Methods, 24:240-246, 2001.

Koivunen et al., "Identification of Receptor Ligands with Phage Display Peptide Libraries", J. Nucl. Med., 40(5):883-888, 1999.

König, et al., "Three cytoplasmic loops of rhodopsin interact with transducin", Proc. Natl. Acad. Sci. USA, 86:6878-6882, 1989.

Kostenis et al., "Molecular Basis of Receptor/G Protein Coupling Selectivity Studied by Coexpression of Wild Type and Mutant m2 Muscarinic Receptors with Mutant Gα$_q$ Subunits", Biochem., 36(36):1487-1495, 1997.

Lambright et al., "Structural determinants for activation of the α-subunit of a heterotrimeric G protein", Nature, 369:621-628, 1994.

Lambright et al., "The 2.0Å crystal structure of a heterotrimeric G protein", Nature, 379:311-319, 1996.

Leeb-Lundberg et al., "Antagonists of Bradykinin That Stabilize a G-protein-uncoupled State of the B2 Receptor Act as Inverse Agonists in Rat Myometrial Cells", J. Biol. Chem., 269(42):25970-25973, 1994.

Ley et al., "Solid-supported reagents for multi-step organic synthesis: preparation and application", Farmaco, 57(4):321-30, 2002. (Abstract Only).

Lichtarge et al., "Evolutionarily conserved G$_{αβγ}$ binding surfaces support a model of the G protein-receptor complex", Proc. Natl. Acad. Sci. USA, 93:7507-7511, 1996.

Lipinski et al., "Experimental and computational approaches to estimate solubility and permeability in drug discovery and development settings", Adv. Drug Delivery Rev., 23:3-25, 1997.

Martin et al., "Potent Peptide Analogues of a G Protein Receptor-binding Region Obtained with a Combinatorial Library", J. Biol. Chem., 271(1):361-366, 1996.

Matsuoka et al., "Sequence analysis of cDNA and genomic DNA for a putative pertussis toxin-insensitive guanine nucleotide-bindings regulatory protein α subunit", Proc. Natl., Acad. Sci. USA, 85:5384-5388, 1998.

Mazzoni and Hamm, "Interaction of Transducin with Light-activated Rhodopsin Protects It from Proteolytic Digestion by Trypsin", J. Biol. Chem., 271(47):30034-30040, 1996.

Mixon et al., "Tertiary and Quaternary Structural Changes in G$_{iα1}$ Induced by GTP Hydrolysis", Science, 270:954-960, 1995.

Neubig et al., "International Union of Pharmacology Committee on Receptor Nomenclature and Drug Classification. XXXVIII. Update on Terms and Symbols in Quantitative Pharmacology", Pharmacol. Rev., 55(4):597-606, 2003.

Nielsen et al., "Sequence-selective recognition of DNA by strand displacement with a thymine-substituted polyamide", Science, 254(5037):1497-1500, 1991. (Abstract only).

Onrust et al., "Receptor and βγ Binding Sites in the β Subunit of the Retinal G Protein Transducin", Science, 275:381-383, 1997. (Abstract only).

Osawa and Weiss, "The Effect of Carboxyl-terminal Mutagenesis of G$_t$α on Rhodopsin and Guanine Nucleotide binding", J. Biol. Chem., 270(52):31052-31058, 1995.

Pei et al., "A constitutively active mutant β$_2$-adrenergic receptor in constitutively desensitized and phosphorylated", Proc. Natl. Acad. Sci. USA, 91:2699-2702, 1994.

Rasenick et al., "Synthetic Peptides as Probes for G Protein Function", J. Biol. Chem., 269(34):21519-21525, 1994.

Ren et al., "Constitutively Active Mutants of the β$_2$-Adrenergic Receptor", J. Biol. Chem., 268(22):16483-16487, 1993.

Rodi et al., "Phage-display technology-finding a needle in a vast molecular haystack", Current Opinion in Biotechnology, 10:87-93, 1999.

Samama et al., "Negative Antagonists Promote an Inactive Conformation of the β$_2$-Adrenergic Receptor", Mol. Pharmacol., 45:390-394, 1994.

Schatz et al., "Screening of Peptides Libraries Linked to *lac* Repressor", Methods in Enzymology, 267:171-191, 1996.

Sondek et al., "Crystal structure of a G$_A$ protein βγ dimer at 2.1Å resolution", Nature, 379:369-374, 1996.

Sondek et al., "GTPase mechanism of Gproteins from the 1.7-Å crystal structure of transducin β—GDP —AlF$_4$", Nature, 372:276-279, 1994.

Sullivan et al., "Identification of receptor contact site involved in receptor-G protein coupling", Nature, 330:758-760, 1987.

Sundberg, Steven A., "High-throughput and ultra-high-throughput screening: solution-and cell-based approaches", Current Opinion in Biotechnology, 11:47-53, 2000.

Szardenings et al., "New highy specific agonistic peptides for human melanocortin MC$_1$ receptor", Peptides, 21:239-243, 2000.

Tiberi and Caron, "High Agonist-independent Activity Is a Distinguishing Feature of the Dopamine D1B Receptor Subtype", J. Biol. Chem., 269(45):27925-27931, 1994.

Vanhauwe et al., "Thrombin Receptors Activate G₀ Proteins in Endothelial Cells to Regulate Intracellular Calcium and Cell Shape Changes", J. Biol. Chem., 277(37): 34143-34149, 2002.

Vassart et al., "The G Protein-coupled Receptor Family and One of Its Members, the TSH Receptor", Ann. N.Y. Acad. Sci., 766:23-30, 1995.

Verrall et al. "The Thrombin Receptor Second Cytoplasmic Loop Confers Coupling to $G_q$-like G Proteins in Chimeric Receptors", J. Biol. Chem., 272(11):6898-6902, 1997.

Wall et al. "The Structure of the G Protein Heterotrimer $G_{i\alpha 1}\beta_1\gamma_2$", Cell, 83:1047-1058, 1995.

West et al., "Pertussis Toxin-catalyzed ADP-ribosylation of Transducin", J. Biol. Chem., 260(27):14428-14430, 1985.

Windh et al., "Differential Coupling of the Sphingosine 1-Phosphate Receptors Edg-1, Edg-3, and H218/Edg-5 to the $G_i$, $G_q$, $G_{12}$ families of Heterotrimeric G Proteins", J. Biol. Chem., 274(39):27351-27358, 1999.

Yu et al., "Inhibition of Subsets of G Protein-Coupled Receptors By Empty Mutants of G Protein α Subunits in $G_0$, $G_{11}$, and $G_{16}$", J. of Biol. Chem., 275 (1): 71-76, 2000.

Yu et al., "Interaction of the Xanthine Nucleotide Binding Goα Mutant With G Protein-coupled Receptors", J. of Biol. Chem., 273(46):30183-30188, 1998.

Zwick et al., "Phage-displayed peptide libraries", Current Opinion in Biotechnology, 9:427-436, 1998.

Anonymous, "Combinatorial Chemistry," Nat. Biotechnol., 18 (Supp):IT50-IT52, 2000.

Chen et al., "Functional Expression of a Human Thrombin Receptor in Sf9 Insect Cells: Evidence for an Active Tethered Ligand," Biochem J., 314:603-611, 1996.

Damaj et al., "Identification of G-protein Binding Sites of the Human Interleukin-8 Receptors by Functional Mapping of the Intracellular Loops," FASEB J., 10:1426-1434, 1996.

Dolle, R.E., "Comprehensive Survery of Combinatorial Library Snynthesis: 1999," Journal of Combinatorial Chemistry, 2(5):383-433, 2000.

Filteau et al., "Effects of Reciprocal Chimeras Between the C-terminal Portion of Third Intracellular Loops of the Human Dopamine $D_2$ and $D_3$ Receptors," FEBS Letters 447:251-256, 1999.

Forse et al., "Biology of Heterotrimeric G-Protein Signaling," Official Journal of the Society of Critical Care Medicine, 28(4):Supplement, pp. N53-N59, 2000.

Grey, N.S., "Combinatorial Libraries and Biological Discovery," Current Opinion in Neurobiology, 11:608-614, 2001.

Jakubik et al., "Activation of Muscarinic Acetylcholine Receptors Via Their Allosteric Binding Sites," Proc. Natl. Acad. Sci., USA, 93:8705-8709, 1996.

Kai et al., "G-protein Binding Domains of the Angiotensin II $AT_{1A}$ Receptors Mapped with Synthetic Peptides Selected from the Receptor Sequence," J. Biochem., 332:781-787, 1998.

Marin et al., "The Amino Terminus of the Fourth Cytoplasmic Loop of Rhodopsin Modulates Rhodopsin-Transducin Interaction," J. Biol. Chem., 275(3):1930-1936, 2000.

Mason et al., "A Gain-of-function Polymorphism in a G-protein Coupling Domain of the Human $\beta_1$-Adrenergic Receptor", J. Biol. Chem., 274(18):12670-12674, 1999.

Ulloa-Aguirre et al., "The Third Intracellular Loop of the Rat Gonadotropin-Releasing Hormone Receptor Couples the Receptor to $G_s$- and $G_{q/11}$-Mediated Signal Transduction Pathways: Evidence from Loop Fragment Transfection in $GGH_3$ Cells," Endocrinology, 139(5):2472-2478, 1998.

Weber, L., "High-Diversity Combinatorial Libraries," Current Opinion in Chemical Biology, 4:295-302, 2000.

Zhou et al., "Phenylalanine 138 in the Second Intracellular Loop of Human Thromboxane Receptor is Critical for Receptor-G-Protein Coupling," Biochemical and Biophysical Research Communications, 264:171-175, 1999.

Jones, Philip G., et al., "Non-Binding Site Modulation of G Protein-Coupled Receptor Signalling," Exp. Opin. Ther. Patents 9(12):1641-1654, 1999.

Edwards, Stephen W., et al., "Localization of G-Protein-Coupled Receptors in Health and Disease," TIPS 21: 304-308, Aug. 2000.

Akhter, Shahab A., et al., "Targeting the Receptor-$G_q$ Interface to Inhibit in Vivo Pressure Overload Myocardial Hypertrophy," Science, 280: 574-577, Apr. 24, 1998.

Carell, Thomas, et al., "New Promise in Combinatorial Chemistry: Synthesis, Characterization, and Screening of Small-Molecule Libraries in Solution," Chemistry & Biology 2: 171-183, Mar. 1995.

Coleman, David E., et al., "Structures of Active Conformations of $G_{i\alpha 1}$ and the Mechanism of GTP Hydrolysis," Science 265: 1405-1412, Sep. 2, 1994.

Ellis, Chad A., et al., Thrombin Induces Proteinase-Activated Receptor-1 Gene Expression in Endothelial Cells Via Activation of $G_i$-Linked Ras/Mitogen-Activated Protein Kinase Pathway, J. of Biol. Chem., 274 (19): 13718-13727, May 7, 1999.

Lui, Jie, et al., "Identification of a Receptor/G-Protein Contact Site Critical for Signaling Specificity and G-Protein Activation," Proc. Natl. Acad. Sci. USA 92: 11642-11646, Dec. 1995.

Krapivinsky, Grigory, et al., "$G_{\beta\gamma}$ Binding to GIRK4 Subunit Is Critical for G Protein-Gated $K^+$ Channel Activation," J. of Biol. Chem. 273(27): 16946-16952, Jul. 3, 1998.

Krapivinsky, Grigory, et al., "Gβγ Binding to GIRK4 Subunit Is Critical for G Protein-Gated $K^+$ Channel, $I_{KACh}$," J. of Biol. Chem. 270(49): 29059-29062, Dec. 8, 1995.

Tietze, Lutz F., et al., "Domino Reactions for Library Synthesis of Small Molecules in Combinatorial Chemistry," Curr. Opin. in Chem. Biol. 2: 363-371, 1998.

Sowell, Margaret O., et al., "Targeted Inactivation of $\alpha_{12}$ or $\alpha_{13}$ Disrupts Activation of the Cardiac Muscarinic $K^+$ Channel, $I_{K+Ach}$, in Intact Cells," Proc. Natl. Acad. Sci. USA 94: 7921-7926, Jul. 1997.

Höller, C., et al., "G Proteins As Drug Targets," Cell. Mol. Life Sci. 55: 257-270, 1999.

* cited by examiner

FIGURE 1
Bind GPCR to well
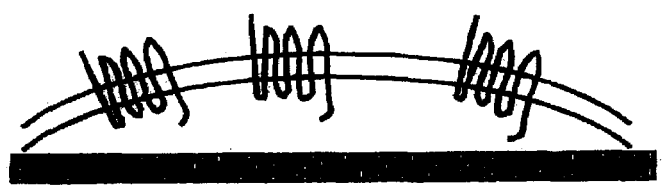
Add peptide library
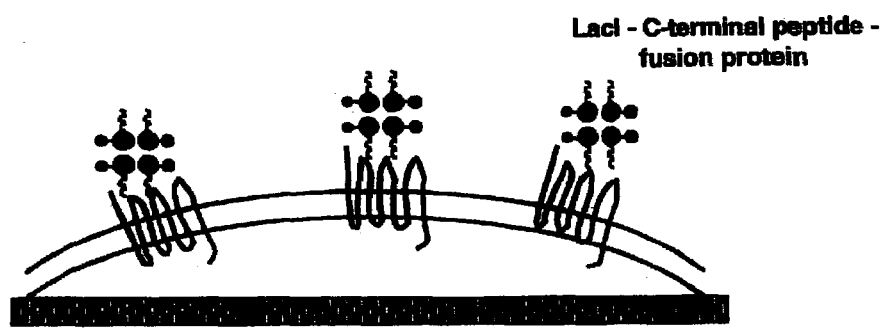
Use parent peptide to compete
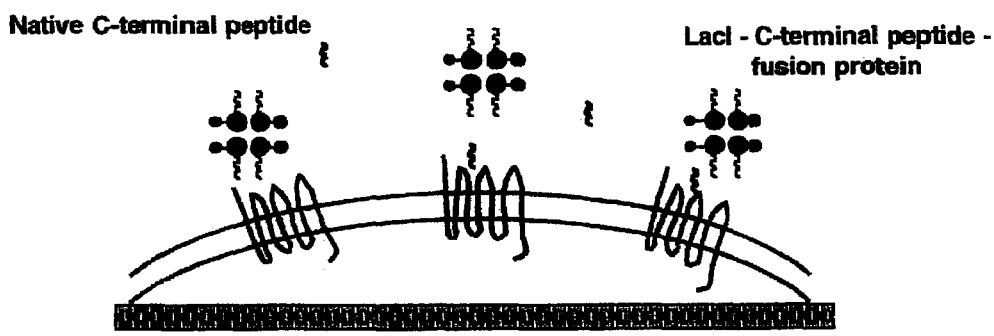

map of pJS142 vector

METHOD FOR IDENTIFYING MODULATORS OF G PROTEIN COUPLED RECEPTOR SIGNALING

This application is a continuation-in-part of prior co-pending application Ser. No. 09/852,910, filed May 11, 2001, which claims priority from prior co-pending provisional application Ser. No. 60/275,472, filed Mar. 14, 2001.

BACKGROUND OF THE INVENTION

1. Technical Field

The present invention generally pertains to the field of modulating activity of G protein-coupled receptors (GPCR) and of identifying and preparing G protein coupled receptor antagonist and agonist compounds, including direct, indirect, full, partial, inverse and allosteric agonists. The invention also encompasses compounds that bind to GPCR to stabilize a particular conformation of the GPCR. These compounds can serve as lead compounds for drug discovery purposes or for studying the GPCR three dimensional structure of specific conformations by such methods as X-ray crystallography or NMR. The invention also relates to an approach using high-throughput screening to identify small molecules that can bind to GPCRs and modulate their function by affecting the way in which they contact their cognate G protein(s). As a first step in identifying GPCR modulators, peptide analogs are identified that mimic or antagonize G proteins and bind with high affinity to the particular receptor under study. These peptides then are tested for their specificity. The most specific peptides are used in a competitive assay to screen for small molecules or other peptides that can, for example, (1) increase the binding of the high affinity peptide ("super agonist") or (2) can decrease the binding of the high affinity peptide, presumably by competing for binding at the GPCR ("antagonists").

2. Description of the Background Art

A great number of chemical messengers exert their effects on cells by binding to G protein-coupled receptors (GPCR). GPCR include a wide range of biologically active receptors such as hormone receptors, viral receptors, growth factor receptors, chemokine receptors, sensor receptors and neuroreceptors. These receptors are activated by the binding of ligand to an extracellular binding site on the GPCR and mediate their actions through the various G proteins. The molecular interactions that occur between the receptor and the G protein are fundamental to the transduction of environmental signals into specific cellular responses.

G protein-coupled receptors have seven transmembrane helices which form, on the intracellular side of the membrane, the G protein binding domain. Experiments have suggested that activation of the receptor by ligand binding changes conformation of the receptor, unmasking G protein binding sites on the intracellular face of the receptor. The transduction of the signal from the extracellular to intracellular environments requires the actions of heterotrimeric G proteins. The molecular interactions that occur between the receptor and the G protein are fundamental to the transduction of environmental signals into specific cellular responses. Heterotrimeric G proteins are thought to interact with GPCR in a multi-site fashion with the major site of contact being at the carboxyl terminus of the Gα subunit. Hamm et al., *Science* 241:832-835, 1998; Osawa and Weiss, *J. Biol. Chem.* 270:31052-31058, 1995; Garcia et al., *EMBO J.* 14:4460-4469, 1995; Sullivan et al., *J. Biol. Chem.* 269:21519-21525, 1994; West et al., *J. Biol. Chem.* 260:14428-14430, 1985.

In the inactive state, G proteins are heterotrimeric, consisting of one α, one β and one γ subunit and a bound deoxyguanosine diphosphate (GDP). Following ligand binding, the GPCR becomes activated. Conformational changes in the activated receptor lead to activation of the G protein, with subsequent decreased affinity of Gα for GDP, dissociation of the GDP and replacement with GTP. Once GTP is bound, Gα assumes its active conformation, dissociates from the receptor, and activates a downstream effector. Hydrolysis of GTP to GDP, catalyzed by the G-protein itself, returns the G-protein to its basal, inactive form. Thus, the G-protein serves a dual role, as both an intermediate that relays the signal from receptor to effector and as a clock that controls the duration of the signal. A variety of studies have implicated the carboxyl terminus of G protein α subunits in mediating receptor-G protein interaction and selectivity.

The carboxyl terminal 11 amino acids are most important to receptor interaction and to the specificity of this interaction. Martin et al., *J. Biol. Chem.* 271:361-366, 1996; Kostenis et al., *Biochemistry* 36:1487-1495, 1997. Other regions on Gα also are involved in receptor contact, however. Portions of the Gβγ dimer also have been implicated in GPCR binding. See Onrust et al., *Science* 275:381-384, 1997; Lichtarge et al., *Proc. Natl. Acad. Sci. USA* 93:7507-7611, 1996; Mazzoni and Hamm, *J. Biol. Chem.* 271:30034-30040, 1996; Bae et al., *J. Biol. Chem.* 272:32071-32077, 1997. The carboxyl terminal amino acid regions of Gα proteins (and other GPCR binding regions of the heterotrimeric G protein) not only provide the molecular basis of receptor-mediated activation of G proteins, but also play an important role in determining the fidelity of receptor activation. Conklin et al., *Nature* 363:274-276, 1993; Conklin et al., *Mol. Pharmacol.* 50:885-890, 1996.

The involvement of the carboxyl-terminal 11 amino acids of Gt (amino acids 340-350) in interactions with the activated GPCR (R*) is suggested by many studies, including (a) the finding that Pertussis toxin catalyzes the ADP-ribosylation of Cys0347, which uncouples Gt from R*; (b) a peptide corresponding to amino acids 340-350 of Gt can uncouple R* from Gt and can itself bind to R* and mimic the effects of Gt; (c) site-directed mutagenesis; and (d) the demonstration in related G proteins that specificity of coupling to particular receptors resides in their carboxyl terminus in interacting with R*.

The G proteins play important and intricate roles in determining the specificity and temporal characteristics of the cellular response to the ligand-binding signal. Hamm and Gilchrist, *Curr. Opin. Cell Biol.* 8:189-196, 1996. Multiple receptors can activate a single G protein subtype, and in some cases a single receptor can activate more than one G protein, thereby mediating multiple intracellular signals. In other cases, however, interaction of a receptor with a G protein is regulated in a highly selective manner such that only a particular heterotrimer is bound.

Recognition sites are the precise molecular regions on receptors to which the activating molecules bind. An agonist is an endogenous substance or a drug that can interact with a receptor and initiate a physiological response. A drug may interact at the same site as an endogenous agonist (i.e., hormone or neurotransmitter) or at a different site. Agonists that bind to an adjacent or a different site are termed allosteric agonists. As a consequence of the binding to allosteric binding sites, the interaction with the normal ligand may be either enhanced or reduced. The conformational change which the allosteric modulators induce in receptors concerns not only the binding domain for the classical ligands, but also the domain responsible for the interaction between the receptors and the G proteins.

The visual system is an example of one in which G protein signaling is important. Rod cells of the retina make up 95% of the photoreceptors and are highly sensitive to light. Rods allow vision at night or under conditions of very dim illumination. The rod visual protein rhodopsin resides in disk membranes in the rod outer segment (ROS). Rhodopsin is a prototypical GPCR. Helmreich and Hofmann, *Biochim. Biophys. Acta* 1286:285-322, 1996; Menon et al., *Physiol. Rev.* 81:1659, 2001; Teller et al., *Biochemistry* 40:7761, 2001. Rhodopsin is unique among GPCRs as it is not ligand activated.

Night vision relates to the ability of the organism to discriminate between slight differences in the intensity of dim light and, when dark-adapted, to detect small changes in light. Some persons report consistent difficulties in seeing at night, even when their eyes are fully dark-adapted. They cannot detect objects readily visible to others and show both confusion and slow recovery after brief exposure to relatively bright light sources. Maneuvering in dimly illuminated spaces and driving or flying at night present serious problems to these individuals. In addition, some individuals have nyctalopia, or true night blindness, which is diagnosed on the basis of a measurement of retinal sensitivity.

No definitive data on the occurrence of nyctalopia in the population are available, since measurements have never been made on a representative sample of the population. Studies of select groups (e.g., school children, service men), show that the normal population includes a percentage of persons of low visual sensitivity whose performance will be as poor as or poorer than that of many individuals whose nyctalopia is associated with disease or degenerative processes. For example, about 2 percent of Navy men were disqualified for night duties as "night blind" on this basis. It is also a disease of aging. As the general population ages, incidence of night blindness increases. Night blindness also has been observed in several diseases including:

(1) Retinitis pigmentosa (In the early stages of the disease, dark adaptation takes place, but at a retarded rate. As disease advances, rod function is progressively lost, and the absolute terminal threshold is elevated. More than 100,000 Americans have retinitis pigmentosa, and most people with retinitis pigmentosa are blind by the age of 40. See Farrar et al., *EMBO J.* 21(5):857-864, 2002;

(2) Glaucoma (Early impairment and progressive loss of rod sensitivity is observed in glaucoma. Cursiefen et al., *Doc. Ophthalmol.* 103(1):1-12,2001. Glaucoma is one of the leading causes of blindness in the U.S and one of the most common causes of blindness in individuals over age 60, one of the fastest growing groups in the U.S.);

(3) LASIK (Recent studies indicate a significant number of patients who undergo LASIK surgery fail a night vision test (30-60%). Miller et al., *CLAO J.* 27:84-88, 2001; Brunette et al., *Ophthalmology* 107:1790-1796, 2000;

(4) Side effects of drugs (Several medications can cause night blindness, including Methyltestosterone, Quinidinesis, Paramethadion and Trimethadione (anticonvulsants), Questran (cholesterol-lowering), Accutane (anti-acne), Hydroxychloroquine (anti-malarial), Videx (HIV), and Nefazodone (antidepressant)). Thus, the usefulness of a pharmaceutical approach to night blindness is clear. As the population ages, the number of affected individuals will increase.

Human dietary vitamin A deficiency can cause night blindness, and this can be reversed with vitamin A supplements. However, the night blindness associated with visual diseases such as retinitis pigmentosa (RP), cataracts, diabetic retinopathy, and glaucoma is only somewhat helped with vitamin A supplements, which do not change the course of the disease. Many of the mutations that cause retinal degeneration and visual loss are in genes that encode photoreceptor cascade proteins; others are in genes that encode photoreceptor structural proteins. Pang and Lam, *Hum. Mutat.* 19:189, 2002. Mutations in rhodopsin, PDEβ, or Gαt have been identified in different forms of congenital stationary night blindness. Pepe, *Prog. Retin. Eye Res.* 20:733-759, 2001. Stationary night blindness is not associated with retinal degeneration and manifests itself in the inability to see in the dark; daytime vision is largely unaffected. Congenital stationary night blindness (CSNB) refers to a group of non-progressive retinal disorders that are characterized predominantly by abnormal function of the rod system. Clinical heterogeneity even among family members with the same mutation raises the possibility that modifying factors, either genetic or environmental, influence the severity of the disease. Gottlob, *Curr. Opin. Ophthalmol.* 12:378-383, 2001.

In night blindness resulting from defects in rhodopsin, Gαt, or PDEβ, rod photoreceptors respond only to light intensities far brighter than normal, and the sensitivity of rods to light is similar to that of normal individuals who are not dark adapted. In fundus albipunctatus and in Oguchi disease, the rod photoreceptors can achieve normal sensitivity to dim light but only after 2 or more hours of dark adaptation, compared with approximately 0.5 hours for normal individuals. Dryja, *Am. J. Ophthalmol.* 130:547, 2000. In each of these forms of stationary night blindness, the poor rod sensitivity and the time course of dark adaptation correlate with the known or presumed physiologic abnormalities caused by the identified gene defects. Increasing the efficacy with which rhodopsin activates the phototransduction cascade is a possible new pharmacological approach to night blindness. Activated rhodopsin activates the rod visual G protein, Gt, which activates the visual transduction cascade. Pharmacologically increasing the effective signaling of rhodopsin can significantly impact people's ability to see and function in low light. The ability, therefore, to identify small molecule compounds that enhance the ability of G protein coupled receptors to signal would be a major benefit.

Because G proteins and their receptors influence a large number of intracellular signals mediated by a large number of different chemical ligands, considerable potential for modulation of disease pathology exists. Many medically significant biological processes are influenced by G protein signal transduction pathways and their downstream effector molecules. See Holler et al., *Cell. Mol. Life Sci.* 340:1012-1020, 1999. G protein-coupled receptors and their ligands are the target for many pharmaceutical products and are the focus of intense drug discovery efforts. Over the past 15 years, nearly 350 therapeutic agents targeting GPCRs have been successfully introduced into the market. Because of the ubiquitous nature of G protein-mediated signaling systems and their influence on a great number of pathologic states, it is highly desirable to find new methods of modulating these systems, including both agonist and antagonist effects. The ability to study the three-dimensional conformations of GPCRs in response to different individual ligands with different effects also is highly desirable, since these studies would aid in the search and development of drugs with particular structures which impart particular modulating effects on GPCRs.

Drug receptor theories are grounded in the law of mass action and include the concepts of affinity (the probability of the drug occupying a receptor at any given instant), intrinsic efficacy (intrinsic activity), which expresses the complex associations involving drug or ligand concentration, and activation states of receptors. Drugs classified as agonists interact with receptors to alter the proportion of activated receptors, thus modifying cellular activity. Conventional agonists increase the proportion of activated receptors; inverse agonists reduce it. Direct agonists act on receptors, while indirect agonists facilitate the actions of the endogenous agonist (the neurotransmitter itself). Allosteric modulation of receptor activation is a new approach which circumvents the development of tolerance.

Most currently available drugs affecting GPCRs act by antagonizing the binding between a G protein-coupled receptor and its extracellular ligand(s). On the other hand, receptor subtype-selective drugs have been difficult to obtain. An additional drawback to the classical approach of designing drugs to interfere with ligand binding has been that conventional antagonists are ineffective for some GPCRs such as proteinase activated receptors (PAR) due to the unique mechanism of enzymatic cleavage of the receptor and generation of a tethered ligand. In other cases, intrinsic or constitutive activity of receptors leads to pathology directly, thus rendering antagonism of ligand binding moot. For these reasons, alternative targets for blocking the consequences of GPCR activation and signaling are highly desirable. Increased understanding of the structural conformation of GPCRs under the influence of different agonists, antagonists or other ligands also allows design of compounds with highly specific effects on GPCRs.

One potential alternative target for inhibition by new pharmaceuticals has been the receptor-G protein interface on the interior of the plasma membrane. Konig et al., *Proc. Natl. Acad. Sci. USA* 86:6878-6882, 1989; Acharya et al., *J. Biol. Chem.* 272:6519-6524, 1997; Verrall et al., *J. Biol. Chem.* 272:6898-6902, 1997. The carboxyl terminus of Gα and other regions of the G protein heterotrimer conform to a binding site at the cytoplasmic face of the receptor. Sondek et al., *Nature* 379:311-319, 1996; Sondek et al., *Nature* 379:369-374, 1996; Wall et al., *Science* 269:1405-1412, 1996; Mixon et al., *Science* 270:954-960, 1995; Lambright et al., *Nature* 369:621-628, 1994; Lambright et al., *Nature* 379:311-319, 1996; Sondek et al., *Nature* 379:369-374, 1996; Wall et al., *Science* 269:1405-1412, 1996; Mixon et al., *Science* 270:954-960, 1995. Peptides corresponding to these binding regions or mimicking these regions can block receptor signaling or stabilize the active agonist-bound conformation of the receptor. Hamm et al., *Science* 241:832-835, 1988; Gilchrist et al., *J. Biol. Chem.* 273:14912-14919, 1998.

For example, in the case of rhodopsin, the rod photoreceptor, the Gα C-terminal peptide, Gα 340-350, stabilizes the receptor in its active metarhodopsin II conformation. Hamm et al., *Science* 241:832-835, 1988; Osawa and Weiss, *J. Biol. Chem.* 270:31052-31058, 1995. Two carboxyl terminal peptides from GαS (354-372 and 384-394), but not the corresponding peptides from Gα$i_2$, evoke high affinity agonist binding to $β_2$-adrenergic receptors and inhibit their ability to activate Gαs and adenylyl cyclase. Rasenick et al., *J. Biol. Chem.* 269:21519-21525, 1994. Thus, the carboxyl terminus of Gα is important in mediating the specificity of G protein responses. Drug discovery approaches which take advantage of this phenomenon, however, are not available. Jones et al., *Expert Opin. Ther. Patents* 9(12):1641, 1999.

In general, GPCRs require agonist binding for activation. However, for some receptors basic signaling activity may occur even in the absence of an agonist (constitutive activity). In addition, modifications to the receptor amino acid sequence can stabilize the active state conformation without the requirement for a ligand. Constitutive (agonist-independent) signaling activity has been demonstrated for both mutant and wild type (or native) form receptors (Tiberi and Caron, *J. Biol. Chem.* 269:27925-27931, 1994; Hasegawa et al., *J. Biol. Chem.* 271:1857-1860, 1996). A number of GPCRs that cause disease in humans, for example, receptors for thyroid-stimulating hormone (Vassart et al., *Ann N. Y. Acad. Sci.* 766:23-30, 1995), have been found to exhibit agonist-independent activity. An inverse agonist is an agent that binds to the receptor and suppresses this activity.

Experimentally, several single amino acid mutations have produced agonist-independent activity. β2 and α2 adrenergic receptors, for example, mutated at single sites in the third cytoplasmic loop, show constitutive activity. Ren et al., *J. Biol. Chem.* 268:16483-16487, 1993; Samama et al., *Mol. Pharmacol.* 45:390-394, 1994. In some cases, a large deletion mutation in the carboxyl tail or in the intracellular loops of GPCRs has led to constitutive activity. For example, in the thyrotropin releasing hormone receptor a truncation deletion of the carboxyl terminus or a smaller deletion in the second extracellular loop of the thrombin receptor renders the receptor constitutively active. Nussenzveig et al., *J. Biol. Chem.* 268:2389-2392, 1993; Matus-Leibovitch et al., *J. Biol. Chem.* 270:1041-1047, 1995; Nanevicz et al., *J. Biol. Chem.* 270:21619-21625, 1995.

These findings have led to a modification of traditional receptor theory. Samama et al., *J. Biol. Chem.* 268:4625-4636, 1993. It now is thought that receptors can exist in at least two conformations, an inactive conformation (R) and an activated conformation (R*), and that an equilibrium exists between these two states that markedly favors R over R* in the majority of receptors. It has been proposed that in some receptors (native and mutant) there is a shift in equilibrium in the absence of agonist that allows a sufficient number of receptors to be in the active R* state to initiate signaling. Therefore, in response to chemical or physical external stimuli, GPCRs undergo a conformational change leading to the activation of heterotrimeric G proteins which go on to initiate intracellular signaling events.

Several studies suggest that many GPCRs exhibit properties consistent with the existence of multiple conformational states. In rhodopsin, the existence of multiple conformers is evident from absorbance changes. Sakmar, *Prog. Nucleic Acid Res. Mol. Biol.* 59:1-34, 1998. Activation occurs by transition through intermediate conformations with the equilibrium between these forms showing a characteristic pH sensitivity. See Arnis and Hoffman, *Proc. Natl. Acad. Sci. USA* 90:7849-7853, 1993; Vogel and Siebert, *Biochemistry* 41:3529-3535, 2002. Pharmacological studies suggest that the existence of distinct receptor conformers can have functional significance. Studies of fusion proteins of beta adrenergic receptor and G proteins suggest that partial agonists stabilize a conformational state distinct from that stabilized by a full agonist. Seifert et al., *J. Pharmacol. Exp. Ther.* 297:1218-1226, 2001.

The observation in several receptors that different agonists acting at the same receptor can direct the relative activation of downstream pathways, a phenomenon called "signal trafficking," also suggests the presence of multiple populations of active receptor conformers. Kenakin, *Trends Pharmacol. Sci.* 16:232-238, 1995; Berg et al., *Mol. Pharmacol.* 54:94-104, 1998; Cordeaux et al., *J. Biol. Chem.*

276:28667-28675, 2001; Marie et al., *J. Biol. Chem.* 276: 41100-41111, 2001. Fluorescence studies also suggest the presence of different receptor conformational populations when complexed with functionally distinct agonists. Ghanouni et al., *J. Biol. Chem.* 276:24433-24436, 2001. This emerging support for the existence of distinct, functionally relevant conformers in several GPCRs suggests that, for these receptors, the molecular activation mechanism must provide the means for switching among multiple conformations. A method to study these conformers by methods such as crystallographic methods and NMR would be highly useful in the process of discovering compounds which can modulate or stabilize particular conformers.

Protein-protein interactions involved in regulatory phenomena are reversible and tend to involve only a small fraction of the protein surface. Generally, to identify peptides that block the protein-protein interactions of interest particular peptides are synthesized in an attempt to mimic sections of one of the native interacting proteins or active sequences are selected from random peptide libraries after screening. Peptides are made up of sequences of amino acids, however unlike DNA recognition, which is linearly coded into the sequence, peptide binding is dependent on three-dimensional structure.

The visual pigment, rhodopsin, is the most extensively studied member of the family of G protein receptors. Recently, the X-ray structure of crystalline bovine rhodopsin has been determined to a resolution of 2.8 Å. This has paved the way for an understanding of the structure-function relationships of a prototypical GPCR at the molecular level. Since rhodopsin constitutes greater than 90% of the disk membrane protein, measurements made on the proteins of disk membranes predominantly reflect the properties of rhodopsin in its native environment. Rhodopsin consists of the apoprotein opsin and the chromophore 11-cis retinal. Opsin, consisting of 348 amino acids, has a molecular mass of about 40 kDa and folds into seven transmembrane helices of varying length and one short cytoplasmic helix. The retinylidene chromophore (the aldehyde of vitamin A1) is covalently bound to Lys-296 in helix 7 via a protonated Schiff base and keeps the receptor in an inactive conformation.

Light absorption causes a rapid 11-cis to all-trans isomerization of the chromophore which induces a series conformational of changes of the opsin moiety. This reaction occurs with high efficiency (quantum yield 0.67) and the primary photoproduct, photorhodopsin, is formed within a very short time (200 fs). Subsequently, photorhodopsin thermally relaxes within a few picoseconds to a distorted all-trans configuration, bathorhodopsin. On a nanosecond time scale, bathorhodopsin establishes an equilibrium with a blue-shifted intermediate before the mixture decays to form lumirhodopsin. Lumirhodopsin then is transformed into metarhodopsin I and subsequently metarhodopsin II, the active conformation for G protein coupling. Thus, there are two conformational switches in rhodopsin which are controlled by the protonation of specific amino acids of the protein: the transition from the inactive Meta I state to the active Meta II state and, in the absence of bound retinal, the transition from the inactive to the active state of opsin. According to current models, the receptor is kept in an inactive conformation by electrostatic interactions between charged groups in the protein, which are neutralized by the proton uptake involved in the transition to an active state conformation.

The active receptor species Meta II decays slowly within minutes, by hydrolysis of the Schiff base and dissociation of the receptor into the apoprotein opsin and retinal. Researchers have shown that opsin is in a pH-dependent conformational equilibrium between an active and an inactive state. During the decay of Meta II at neutral pH, most structural changes of Meta II formation are reverted and the decay product opsin eventually adopts an active conformation similar to that of Meta II.

Four distinct steps can be observed in the process of GPCR activation: (1) creation of the signal by a photon or by ligand binding; (2) transduction of the signal through the membrane; (3) interaction with the G protein; and (4) activation of the second messenger. Although the phases clearly differ in the kind of processes taking place, they are not discrete and independent. For example, allostery between ligand binding and G protein binding has been observed for several GPCRs, as well as cation-dependent allosteric regulation of agonist and antagonist binding. Wessling-Resnick and Johnson, *J. Biol. Chem.* 262:12444-12447, 1987; Hepler and Gilman, *Trends Biol. Sci.* 17:383-387, 1992; Nunnari et al., *J. Biol. Chem.* 262:12387-12392, 1987; Neve, *Mol. Pharmacol.*, 39:570-578, 1991; Neve et al., *Mol. Pharmacol.* 39:733-739, 1991.

A number of cytoplasmic proteins interact exclusively with light-activated rhodopsin (R*). Because the crystal structure depicts the inactive form of rhodopsin as not interacting significantly with cytoplamic proteins, this structure can provide only indirect information about the R* state. In addition, two regions of the cytoplasmic surface domain of inactive rhodopsin structure (amino acid residues 236-239 and 328-333) have not been fully resolved by crystal structure analysis. Therefore, tools which can stabilize particular conformers would be useful for studying structure of GPCRs such as rhodopsin.

Negative antagonism is demonstrated when a drug binds to a receptor that exhibits constitutive activity and reduces this activity. Negative antagonists appear to act by constraining receptors in an inactive state. Samama et al., *Mol. Pharmacol.* 45:390-394, 1994. Although first described in other receptor systems, negative antagonism has been shown to occur with GPCRs such as opioid, β2-adrenergic, serotonin type 2C, bradykinin, and D1B dopamine receptors. Schutz and Freissmuth, *J. Biol. Chem.* 267:8200-8206, 1992; Costa and Herz, *Proc. Natl. Acad. Sci. USA* 86:7321-7325, 1989; Costa et al., *Mol. Pharmacol.* 41:549-560, 1992; Samama et al., *Mol. Pharmacol.* 45:390-394, 1994; Pei et al., *Proc. Natl. Acad. Sci. USA* 91:2699-2702, 1994; Chidiac et al., *Mol. Pharmacol.* 45:490-499, 1994; Barker et al., *J. Biol. Chem.* 269:11687-11690, 1994; Leeb-Lundberg et al., *J. Biol. Chem.* 269: 25970-25973, 1994; Tiberi and Caron, *J. Biol. Chem.* 269: 27925-27931, 1994.

That being stated, the concept of constitutively active receptors offer insights which explain pathophysiologic conditions. For example, a constitutively active receptor in a disease process such as hypertension may no longer be under the influence of the sympathetic nervous system. In hypertension, a constitutively active GPCR may be expressed in any number of areas including the brain, kidneys or peripheral blood vessels. A newly recognized class of drugs (negative antagonists or inverse agonists) which reduce undesirable constitutive activity can act as important new therapeutic agents. Thus, a technology for identifying negative antagonists (or understanding and stabilizing the conformational change in a GPCR that binding a negative antagonist compound causes) of both native and mutated GPCRs has important predictable as well as not yet realized pharmaceutical applications. Furthermore, because at least some constitutively active GPCRs are tumorigenic, the identification of negative antagonists for these GPCRs can lead to the development of anti-tumor and/or anti-cell proliferation drugs.

Mutagenesis studies of the carboxyl terminal region of Gαt have identified several specific amino acid residues in this binding region crucial for Gαt activation by rhodopsin. Martin et al., *J. Biol. Chem.* 271:361-6, 1996. Substitution of three to five carboxyl-terminal amino acids from Gαq with corresponding residues from Gαi allowed receptors which signal exclusively through Gαi subunits to activate the chimeric α subunits and stimulate the Gαq effector, phospholipase C β. Conklin et al., *Nature* 363:274-276, 1993; Conklin et al., *Mol. Pharmacol.* 50:885-890, 1996. All of these studies suggest that Gα carboxyl peptide sequences are responsible for the specificity of the signaling responses of the individual G proteins. There are 16 unique Gα subunits (Gαi$_1$, Gαi$_2$, Gαi$_3$, GαO$_1$, GαO$_2$, GαZ, Gαt, Gαq, Gα11, Gα14, Gαs, Gα12, Gα13, Gα15/16, GαOLF and Gαgust) thought to mediate specific interaction with different GPCRs, several hundred of which have been cloned. Thus, peptides corresponding to G protein regions which bind the GPCR could be used as competitive inhibitors of receptor-G protein interactions. Hamm et al., *Science* 241-832-835, 1988; Gilchrist et al., *J. Biol. Chem.* 273:14912-14919, 1998. Drug discovery approaches which take advantage of this opportunity, however, are not available. Jones et al., *Expert Opin. Ther. Patents* 9(12):1641-1654, 1999.

Identification of potent lead compounds for use in modern high throughput screening assays and computerized design of new compounds using information about the desired three-dimensional conformation of receptor molecules, for example, are important aspects of the modern drug discovery process. One of the major challenges confronting those using these types of methods is the difficulty of identifying useful binding compounds from very large combinatorial libraries of potential candidate molecules. When literally hundreds of thousands of compounds are screened, characterizing the compounds which test positive for binding, for modulatory activity or for stabilization of a conformation (including false positives) is an expensive and time-consuming process. Hence, a method which can identify potent and useful lead compounds for high throughput screening and useful binding partners for three dimensional conformational studies and which reduce the number of false positives in the screening process would be very desirable.

SUMMARY OF THE INVENTION

Accordingly, the invention provides a method of identifying a G protein coupled receptor signaling modifying peptide, which comprises providing a peptide library based on a native G protein coupled receptor binding peptide; screening the peptide library for high affinity binding to the G protein coupled receptor; and selecting a member of the peptide library having binding to the G protein coupled receptor of higher affinity than that of the native peptide. The screening may be performed by testing for binding to an intact G protein coupled receptor or to at least an intracellular fragment of a G protein coupled receptor.

The G protein coupled receptor binding peptide may be a G protein subunit or fragment thereof which is, for example from about 7 to about 70 amino acids long or from about 7 to about 55 amino acids long or from about 8 to about 50 amino acids long or from about 9 to about 23 amino acids long, and most preferably about 11 amino acids long. The G protein subunit fragment preferably is a Gα subunit or a Gα subunit carboxyl terminal peptide but alternatively may be a Gβγ dimer.

Screening may comprise a competitive binding assay, which preferably is characterized by co-incubation of members of the peptide library with the G protein coupled receptor binding peptide, for example in an enzyme-linked immunosorbant assay wherein the peptide library members are capable of providing a detectable signal and/or wherein binding to the G protein coupled receptor is determined by measuring a signal generated from interaction of an activating ligand with the G protein coupled receptor.

The peptide library preferably is a combinatorial peptide library or a protein-peptide fusion protein library such as, for example a peptide display library or a maltose binding protein-peptide fusion protein library.

In another embodiment, the invention also provides a method of identifying a G protein coupled receptor signaling modifying compound, which comprises providing a library of candidate compounds to screen for binding to the G protein coupled receptor; providing a high affinity G protein coupled receptor binding peptide; screening the library of candidate compounds for high affinity binding to the G protein coupled receptor in competition with the high affinity G protein coupled receptor binding peptide; and identifying a member of the library of candidate compounds having binding to the G protein coupled receptor of equal or higher affinity than that of the high affinity G protein coupled receptor binding peptide or a member of the library of candidate compounds binding of which results in increased binding affinity of the high affinity G protein coupled receptor binding peptide. Screens may be performed by testing for binding to an intact G protein coupled receptor or to at least an intracellular fragment of a G protein coupled receptor.

The G protein coupled receptor binding peptide may be a G protein subunit or fragment thereof which is, for example from about 7 to about 70 amino acids long or from about 7 to about 55 amino acids long or from about 8 to about 50 amino acids long or from about 9 to about 23 amino acids long, and most preferably about 11 amino acids long. The G protein subunit fragment preferably is a Gα subunit or a Gα subunit carboxyl terminal peptide but alternatively may be a Gβγ dimer.

Screening may comprise a competitive binding assay, which preferably is characterized by co-incubation of members of the peptide library with the G protein coupled receptor binding peptide, for example in an enzyme-linked immunosorbant assay wherein the peptide library members are capable of providing a detectable signal and/or wherein binding to the G protein coupled receptor is determined by measuring a signal generated from interaction of an activating ligand with the G protein coupled receptor.

The library of candidate compounds preferably is a focused library of candidate compounds based on the structure of the high affinity G protein coupled receptor binding peptide. The library of candidate compounds may be a combinatorial library of, for example drug-like molecules or a focused small molecule library whose members, for example may be based on the chemical structure of the high affinity G protein coupled receptor binding peptide.

The invention also provides G protein coupled receptor signaling modifying peptides and compounds identified according to the methods described above, as well as methods of modifying G protein coupled receptor signaling in a cell having a G protein coupled receptor which comprise administering such compounds to the cell. Also provided are methods of inhibiting G protein coupled receptor signaling which comprise contacting a compound with the G protein coupled receptor which interferes with binding of the G protein coupled receptor to its cognate G proteins.

In a further embodiment, the invention provides a method for identifying a G protein coupled receptor signaling modifying compound, which comprises providing a peptide identified according to at least one of the methods described above, wherein the peptide is labeled to provide a detectable peptide signal; providing a library of candidate G protein coupled receptor signaling modifying compounds; contacting the peptide with the G protein coupled receptor under conditions such that the peptide binds to the G protein coupled receptor; removing unbound peptide from the G protein coupled receptor; measuring the signaling activity of the peptide-bound G protein coupled receptor and measuring the detectable peptide signal; contacting the members of the library of candidate G protein coupled receptor signaling modifying compounds with the peptide-bound G protein coupled receptor; measuring the signaling activity of the peptide bound G protein coupled receptor and measuring the detectable peptide signal; determining whether the G protein coupled receptor signaling activity is increased or decreased after contact with the candidate compound and whether G protein coupled receptor peptide binding is increased or decreased after contact with the candidate compound; and identifying compounds for which contact with the peptide-bound G protein coupled receptor results in both an increase in peptide binding to the G protein coupled receptor and an increase in G protein coupled receptor signaling, identifying compounds for which contact with the peptide-bound G protein coupled receptor results in both a decrease in peptide binding to the G protein coupled receptor and a decrease a G protein coupled receptor signaling and identifying compounds for which contact with the peptide-bound G-protein coupled receptor results in increased binding affinity of the peptide identified according to a method described above. Methods for measuring the signaling activity of the peptide-bound G protein coupled receptor may be selected from the group consisting of measuring inositol phosphate accumulation; measuring intracellular $Ca^{2+}$ levels; measuring adenyl cyclase activity; measuring transendothelial electrical resistance; measuring stress fiber formation; measuring ligand binding; measuring receptor expression; measuring receptor desensitization; measuring kinase activity; measuring phosphatase activity; measuring nuclear transcription factors; measuring all migration (chemotaxis); measuring superoxide formation; measuring nitric oxide formation; measuring cell degranulation; measuring GIRK activity; measuring actin polymerization; measuring vasoconstriction; measuring cell permeability; measuring apoptosis; measuring cell differentiation; measuring membrane association of a protein that translocates upon GPCR activation, such as protein kinase C; measuring cytosolic accumulation of a protein that translocates upon GPCR activation, such as protein kinase C; and measuring nuclear association of a protein that translocates upon GPCR activation, such as Ran.

In yet a further embodiment, the invention provides compounds selected from the group consisting of SEQ ID NOS: 2, 4, 6, 8, 10, 12, 13, 15, 17, 21, 23, 25-27, 30, 32, 34, 36, 38, 40, 45-85, 94-111, 125-150, 160-164, 175-178 and 183-264.

In yet a further embodiment, the invention provides a method for providing a therapeutic G protein coupled receptor signaling modifier peptide to a mammal which comprises administering to the mammal an expression construct which expresses a compound selected from the group consisting of SEQ ID NOS: 2, 4, 6, 8, 10, 12, 13, 15, 17, 21, 23, 25-27, 30, 32, 34, 36, 38, 40, 45-85, 94-111, 125-150, 160-164, 175-178 and 183-264. Further, the invention provides a method for treating a disease state in which excess G protein coupled receptor signaling is a causative factor, which comprises administering a compound selected from the group consisting of SEQ ID NOS: 2, 4, 6, 8, 10, 12, 13, 15, 17, 21, 23, 25-27, 30, 32, 34, 36, 38, 40, 45-85, 94-111, 125-150, 160-164, 175-178 and 183-264.

In yet a further embodiment, the invention provides a method of identifying a G protein coupled receptor signaling enhancer, which comprises providing a peptide library based on a native G protein coupled receptor binding peptide; screening the peptide library for high affinity binding to the G protein coupled receptor; selecting a member of the peptide library having binding to the G protein coupled receptor of higher affinity than that of the native peptide; providing a library of candidate compounds to screen for binding to the G protein coupled receptor; screening the library of candidate compounds for high affinity binding to the G protein coupled receptor in competition with a member of the peptide library selected above; and identifying a member of the library of candidate compounds having binding to the G protein coupled receptor of equal or higher affinity than that of the peptide selected above or identifying a member of the library of candidate compounds binding of which results in increased binding affinity of the peptide selected above. Screening methods for use in this embodiment may include testing for binding to an intact G protein coupled receptor or testing for binding to at least an intracellular fragment of a G protein coupled receptor. The G protein coupled receptor binding peptide may be a G protein subunit or fragment thereof, for example a G protein subunit fragment from about 7 to about 70 amino acids long, from about 7 to about 55 amino acids long, from about 8 to about 50 amino acids long, from about 9 to about 23 amino acids long or most preferably about 11 amino acids long. The G protein subunit fragment preferably is a Gα subunit or a Gα subunit carboxyl terminal peptide but alternatively may be a Gβγ dimer.

Screening may comprise a competitive binding assay, which preferably is characterized by co-incubation of members of the peptide library with the G protein coupled receptor binding peptide, for example in an enzyme-linked immunosorbant assay wherein the peptide library members are capable of providing a detectable signal and/or wherein binding to the G protein coupled receptor is determined by measuring a signal generated from interaction of an activating ligand with the G protein coupled receptor.

The library of candidate compounds preferably is a focused library of candidate compounds based on the structure of the high affinity G protein coupled receptor binding peptide. The library of candidate compounds may be a combinatorial library of, for example drug-like molecules or a focused small molecule library whose members, for example may be based on the chemical structure of the high affinity G protein coupled receptor binding peptide.

Enzyme-linked immunosorbant assays for use in the inventive method may comprise the steps of immobilizing the G protein coupled receptor onto a solid support; providing a protein-peptide fusion protein display library; incubating members of the protein-peptide fusion protein display library with the immobilized G protein coupled receptor in the presence of the G protein coupled receptor binding peptide under conditions such that members of protein-peptide fusion protein display library having a binding affinity for the G protein coupled receptor at least as high as the G protein coupled receptor binding peptide bind to the immobilized G protein coupled receptor; removing unbound members of the protein-peptide fusion protein display library; incubating the bound protein-peptide fusion protein display library with antibodies which specifically recognize the protein portion of the protein-peptide fusion protein display library members under conditions such that the antibodies specifically bind to the protein-peptide fusion protein display library members; removing unbound antibodies; and detecting the bound antibodies. The protein-peptide fusion protein display library preferably is a maltose binding protein-peptide fusion protein display library and the antibodies preferably are anti-maltose binding protein antibodies. Binding to the G protein coupled receptor preferably is determined by measuring a signal generated from interaction of the signalling enhancer with the G protein coupled receptor.

The peptide library preferably is a combinatorial peptide library, for example a protein-peptide fusion protein library such as a maltose binding protein-peptide fusion protein library or any suitable peptide display library. Libraries of candidate compounds preferably are focused libraries of candidate compounds based on the structure of the compound selected above as having binding to the G protein coupled receptor of higher affinity than that of the native peptide. The library may be a peptide library or a small molecule library.

In yet a further embodiment, the invention provides compounds identified by a method as described above. In yet further embodiments, the invention provides a method for treating a disease state in which alterations in G protein coupled receptor signaling is a causative factor and a method for treating a disease state in which alterations in G protein coupled receptor signaling is a causative factor both of which comprise administering these compounds. In yet a further embodiment the invention provides a method of determining the three-dimensional structure of a G protein coupled receptor, which comprises contacting the G protein coupled receptor with a compound identified by at least one of the methods described above under conditions such that binding occurs and a conformation of the G protein coupled receptor is stabilized; co-crystallizing the G protein coupled receptor-compound binding pair; subjecting the co-crystallized binding pair to X-ray crystallography; and determining the three-dimensional structure of the co-crystallized binding pair, wherein atomic coordinates of the G protein coupled receptor are obtained. In yet a further embodiment, the invention provides a method of determining the three-dimensional structure of a G protein coupled receptor, which comprises contacting the G protein coupled receptor with a compound identified by at least one of the methods described above under conditions such that binding occurs and a conformation of the G protein coupled receptor is stabilized; subjecting the binding pair to nuclear magnetic resonance study; and determining the three-dimensional structure of the binding pair, wherein atomic coordinates of the G protein coupled receptor are obtained.

In yet a further embodiment, the invention provides a method of isolating a G protein coupled receptor binding partner, which comprises providing a solid support comprising bound compound identified by at least one of the methods described above; providing a library of candidate G protein coupled receptor binding partner compounds; contacting the library of candidate compounds with the solid support under conditions such that binding of the candidate compounds to the compound occurs; eluting unbound and nonspecifically bound candidate compounds from the solid support; and recovering bound candidate compounds from the solid support.

In yet a further embodiment, the invention provides a method of designing small molecules that modify activation of a G protein coupled receptor, which comprises determining the three-dimensional structure of a G protein coupled receptor according to at least one of the methods described above; and designing candidate structures by computer modeling based on the atomic coordinates, wherein the candidate structures are predicted to bind to the G protein coupled receptor.

In yet a further embodiment, the invention provides a nucleic acid which comprises a DNA that encodes a peptide identified by at least one of the methods described above, wherein the DNA is operably linked to a heterologous transcriptional regulatory sequence, an expression vector which comprises this nucleic acid and a cell transfected with the expression vector. The invention also provides an antibody that specifically recognizes a peptide identified by any of the methods described above, such as, for example, a monoclonal antibody, a polyclonal antibody, a humanized antibody or a single chain antibody.

BRIEF DESCRIPTION OF THE DRAWINGS

FIG. 1 is a schematic diagram showing the basic two-step platform.

FIG. 16A presents fluorescence ([$Ca^{++}$]$_i$ level) increase 30 seconds after thrombin addition. FIG. 16B shows the kinetics of [$Ca^{++}$] fluorescence changes after cell stimulation with thrombin.

DETAILED DESCRIPTION OF THE PREFERRED EMBODIMENTS

Figure 2:
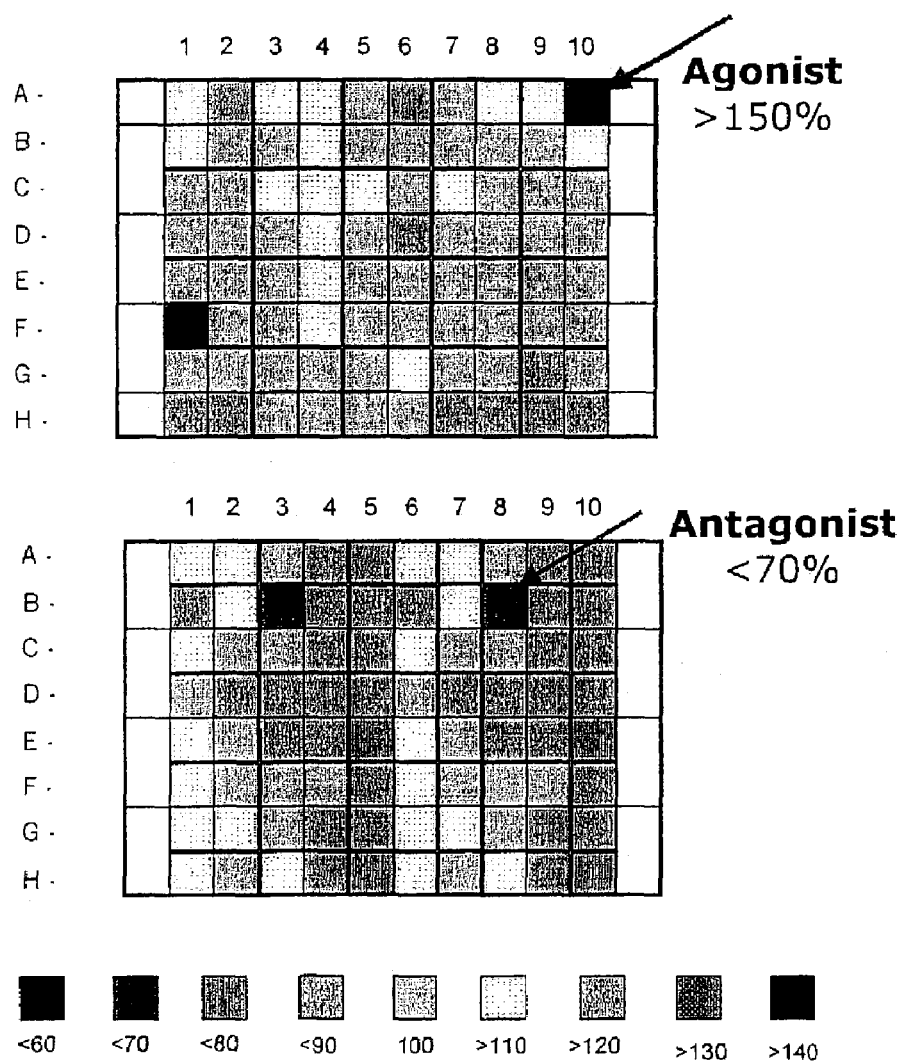
FIG. 2 is a schematic diagram showing the basis for the affinity screening method used to separate and identify GPCR binding peptides.

The present invention involves a method of identifying compounds which can interfere with or increase binding between a G protein-coupled receptor (GPCR) and its cognate G protein(s) and compounds which stabilize a particular conformation of a GPCR for conformational study. These compounds modulate G protein-mediated signaling and thus can be used as pharmaceuticals, as lead compounds for identification of potential useful drugs, as components of assays which identify drug candidates or as binding partners in conformational studies by known methods, such as for example X-ray crystallography or nuclear magnetic resonance.

Methods for screening and drug identification use peptides that mimic the structure of the GPCR binding regions of G proteins and thus are able to modulate receptor-G protein interactions specifically or specifically bind to a given receptor with high affinity. These high affinity peptides can be delivered into cells in the context of an expression construct to act as blockers or agonists of specific receptor-mediated cellular responses in vitro and in vivo or can be administered directly to a patient. The peptides also form the basis of a screening, identification and selection process to provide traditional pharmaceutical compounds or to study structure-function relationships in binding. In particular, the invention allows one to identify high affinity analog peptides that block or mimic compounds at the receptor-G protein interface for a particular G protein and to use these high affinity analogs in a high throughput screen to identify other peptides or small molecules that likewise specifically antagonize or agonize GPCR signaling for a G protein or class of G proteins.

Small molecules can be used in analogous high throughput screening processes to identify further compounds. "Small molecule" denotes any non-peptide organic compound which binds or interferes with binding to the interfacial region of a GPCR or is a candidate for such action. Such molecules that bind to and stabilize a particular conformer of a GPCR also are included in the definition of "small molecule" as used herein. Peptides or small molecules directed at the receptor-G protein interface can be designed using the inventive method to inhibit or enhance biological processes that employ signaling through a GPCR or to bind to and stabilize a particular GPCR conformer. Such compounds which bind to, interfere into binding to or stabilize a conformer of the GPCR-G protein interface (including but not limited to agonists, inverse agonists, allosteric agonists, blockers, antagonists, inhibitors, negative antagonists, partial agonists, and enhancers, as well as compounds which bind to and stabilize a particular conformer) are termed "modifiers" or "modifying" compounds, and may include both peptides and small molecules. This approach to drug design is useful in targeting G protein-GPCR interactions for which there are no available ligands, orphan receptors the ligands of which are not known, mutant constitutively activated receptors, antibody-crosslinked irreversibly activated receptors such as TSH receptors in Graves' Disease, and proteinase activated receptors (PAR). It works equally well, however, with any GPCR-G protein interaction and more broadly, with receptor-protein interactions in general.

Because the method is useful for identifying high affinity compounds that can bind to and enhance or inhibit virtually any GPCR, the approach is useful in identifying compounds which can prevent, ameliorate or correct dysfunctions or diseases in which a specific class of G proteins is relevant. Conditions and disease states for which GPCR enhancers and inhibitors are useful include, but are not limited to: stroke; myocardial infarction; restenosis; atherosclerosis; hypotension; hypertension; angina pectoris; acute heart failure; cardiomyocyte apoptosis; cancers; infections such as bacterial, fungal, protozoan and viral infections, and particularly infections caused by HIV-1 or HIV-2; septic shock; pain; chronic allergic disorders; asthma; inflammatory bowel disease; osteoporosis; rheumatoid arthritis; Graves' disease; post-operative ileus; urinary retention; testotoxicosis; ulcers; obesity; benign prostatic hypertrophy; and psychotic and neurological disorders including anxiety, epilepsy, schizophrenia, manic depression, Parkinson's disease, Alzheimer's disease, delirium, dementia, drug addiction, anorexia, bulimia, mood disorders and sleep disorders; smoking cessation and any other disease or condition that can be treated by C protein coupled receptor inhibition and any other disease or condition that can be treated by G protein coupled receptor activation. Treatment of this diverse set of disorders is possible because the receptors to which various G proteins bind differ enough to allow the creation of a battery of analog peptides which can specifically interface with different GPCR or different classes or groups of GPCR. The relationship of G proteins and G protein signalling to various diseases and conditions such as those listed above is known in the art.

With the inventive screening methods, the sequences identified in a particular screen do not bind to all receptors, but only to the particular receptor of interest. The interaction between a G protein and a GPCR is quite specific. For example, a difference in one amino acid can substantially reduce or eliminate the ability of the $G\alpha i_{1/2}$ peptide to bind the A1 adenosine G protein coupled receptor-G protein interface. Gilchrist et al., *J. Biol. Chem.* 273:14912-14919, 1998. Both upstream regulation of GTP/GDP exchange on G proteins and G protein-mediated effector activation may be inhibited with interfacial binding compounds. Thus, high affinity analog peptides can be designed to specifically interfere with or stabilize a particular action of one GPCR. Likewise agonizing or enhancing peptides also specifically affect one GPCR. These specifically-acting peptide analogs are useful both as pharmaceutical compounds per se, and as potent lead compounds in modern high throughput screens for other peptides and small molecule binders having the same specific GPCR interaction.

The inventive methods, in one embodiment, rely as first step on screening for small molecules that enhance or inhibit the ability of the receptor to interact with the heterotrimeric G protein. Using rhodopsin and transducin, the screen has found small molecules that significantly enhance rhodopsin's ability to form MII, the active form of rhodopsin. Such small molecules can serve as lead compounds in drug discovery efforts directed towards potential therapeutic agents to combat night blindness. Using the screen to identify small molecules, and then testing the identified compounds using in vitro and in vivo analysis will result in discovery of potent, high affinity compounds.

This invention therefore can be used to identify small molecules that enhance the ability of rhodopsin to signal. The inventive methods involve, in one embodiment, screening compound libraries to discover more molecules that increase binding of G protein peptides to activated rhodopsin. The methods also include testing these molecules in a number of assays to determine their effects on rhodopsin signaling, including MII stabilization, guanosine 5'-O-(3-[$^{35}$S]thio)triphosphate (GTPγS) binding, and 3',5' cyclic GMP phosphodiesterase (PDE) activation.

Additionally, the methods involve testing the small molecules for their specificity by measuring their effects using another GPCR, for example, human thrombin receptor (PAR1), which also has been shown to couple to Gt. Seibert et al., *Vision Res.* 42:517,1999. Enhancement of the sensitivity of vision in vivo can be tested according to a method of the invention using electroretinography (ERG) of wild type and mutant mice. Chang et al., *Vision Res.* 42:517-525, 2002. The inventive methods also optionally involve optimizing the chemical structure of enhancers or antagonists, performing pharmacokinetic, toxicological and metabolism studies of the discovered chemical entities, and large animal efficacy studies, and clinical trials for a pharmacological treatment for night blindness. Therefore, the methods of the invention can be used, for example, to identify small molecules that enhance the binding of the high affinity Gt peptides to light activated rhodopsin, determine whether the small molecules enhance rhodopsin signaling in vitro, determine if the small molecules are specific for rhodopsin, or if they can enhance other GPCR-G protein signaling events, and test the small molecules in a mouse model for stationary night blindness for increased sensitivity of vision as measured by ERG.

A first step was to identify peptides with sequences based on the C-terminus of Gt that bind with high affinity to either light-activated or dark-adapted rhodopsin. These peptide analogs were then tested for their specificity to binding to rhodopsin versus other GPCRs, as well as their ability to stabilize the MII conformation of the receptor. The methods of the invention also identify small molecules that bind light-activated rhodopsin and by doing so enhance the binding of the high affinity peptide analogs. The binding affinity ($EC_{50}$) of the compound is the first criterion of a successful drug candidate. The identified small molecules are tested in vitro for their ability to enhance rhodopsin signaling using assays such as Mil stabilization and MII decay, GTPγS binding, and PDE activation.

Upon activation, rhodopsin undergoes a conformational change that allows its interaction with and activation of Gt, leading ultimately to the stimulation of PDE. The binding of Gt to light-activated rhodopsin induces a high affinity receptor state that can be measured spectrophotometrically by stabilization of the active, signaling metarhodopsin II state of the receptor. Using a split-beam SLM Aminco DW2000 spectrophotometer, for example, one can determine if the receptor undergoes proper conformational changes following light activation. This assay shows the small molecule acting on the conformation of the receptor. If rhodopsin's active intermediate, metarhodopsin II (MII), is stabilized by the presence of the small molecule, the activation energy of the receptor is lowered. Using the inventive assay system, compounds were identified that allow the receptor to enter the active, MII conformation without hetereotrimeric G protein, which normally is required. The "enhancers" stabilize the active (signaling) conformation of the receptor. "Inhibitors" block the binding of transducin to rhodopsin and thus inhibit the receptor from entering the proper conformation even in the presence of agonist (light) and G protein.

Metarhodopsin II decay can be used to examine the differences in compound potencies are due to changes in MII decay. It could be postulated that differences could be due to effects of a compounds to non-specifically attach the retinal Schiff's base linkage of MII. Thus, one can compare the time dependent MII decay in the presence of the individual compounds. In the process of receptor activation, the Gα subunit binds a GTP molecule. GTPγS binding assays can determine the ability of the receptors to signal, with an increase in GTPγS binding indicating receptor-mediated release of the GDP from the α subunit and subsequent binding of GTP. Conversion of inactive transducin (Gt•GDP) to the active state (Gt•GDP) is accompanied by dissociation of the Gα from Gβγ. The free Gα•GTP then activates cGMP phosphodiesterase (PDE) by binding to and dissociating its two inhibitory γ subunits. As a result, the released catalyzing α and β subunits of activated PDE (PDE*) can convert cGMP to GMP. Therefore, compounds which affect rhodopsin signaling can be tested for their affects on PDE assays.

Generally, small molecules that display an appropriate dose curve when used to compete off the high affinity peptide fusion proteins, with a resulting $EC_{50}<100$ μM for binding to rhodopsin are suitable for continued study and are tested for the ability to stabilize MII. Preferably, those with an $EC_{50}<10$ μM for MII stabilization are analyzed further. Further analysis may include thermal stability of rhodopsin in the presence of the small molecules (MII decay), and GTPγS binding (an assay for the small molecule's effects on function). The rate of GTPγS-binding is controlled by a rate-limiting GDP release of Gα subunits. Native Gαt, in the presence or absence of Gβγt, displays very slow intrinsic rates of GDP release. Therefore, an increase in guanosine 5'-O-(3-[$^{35}$S]thio)triphosphate (GTPγS) binding indicates receptor mediated release of the GDP from the α subunit and subsequent binding of the GTP.

GTPγS binding assays may be performed as follows or using any method known in the art. Gα subunits (1 mM) alone, or Gα subunits in the presence of the small molecules to be assayed are mixed with 2 mM Gβγt or 2 mm Gβγt and urea-washed ROS membranes (500 nM rhodopsin) and incubated for 3 min at 25° C. Binding reactions may be started by addition of 5 mm [$^{35}$S]GTPγS (0.1 mCi). Aliquots of 50 μl are withdrawn at several timepoints, mixed with 1 ml ice-cold 20 mm Tris.2HCl (pH 8.0) buffer containing 130 mM NaCl and 10 mM MgSO₄ and passed through Whatman™ cellulose nitrate filters (0.45 mm). The filters are washed three times with the same buffer (3 ml, ice-cold) and counted in a liquid scintillation counter after dissolution in 3a70B mixture. See Skiba et al., *J. Biol. Chem.* 271: 413-424, 1996 for exemplary methods which may be used with the invention. The skilled person will recognize variations and adjustments which may be made to the assay, and such variations are considered within the scope of this invention. The $k_{app}$ values for the binding reactions may be calculated by fitting the data to the equation, GTPγS bound (% bound)= 100% $(1-e^{-kt})$. The small molecule(s) also may be tested for the ability to affect PDE activation. Gtα binding to PDEγ relieves the inhibitory effect of the gamma subunit on the catalytic α and β subunits of PDE and allows the hydrolytic activity of these subunits to be increased almost 300 fold.

Activation of Gtα by rhodopsin can be monitored in the presence or absence of the small molecules using fluorescence spectroscopy at 20° C. as described by Cerione, *Methods Enzymol.* 237:409-423, 1994. This assay measures the Gα:GTPγS (complex between a subunit of transducin and GTPγS) formation rate catalyzed by wild-type rhodopsin upon illumination. The excitation wavelength is 295 nm (2 nm bandwidth), and fluorescence emission is monitored at 340 nm (12 nm bandwidth). Briefly, rhodopsin (40 nM) is added to a solution of Gt (250 nM) in a reaction mixture containing 10 mM Tris (pH 7.2), 2 mM MgCl₂, 100 mM NaCl, 1 mM DTT, and 0.01% n-dodecyl β-maltoside. The solution is stirred for 300 sec to equilibrate. GTPγS (5 μM) is added to the reaction mixture to a final concentration of 5 μM, and the increase in fluorescence is followed for and additional 2000 sec. To calculate the activation rates, the slopes of the initial fluorescence increase after GTPγS addition were determined through the data points covering the first 60 sec. The values in the presence of the small molecules may be normalized to the value obtained for wild-type rhodopsin with no compounds taken as 1.00. Those molecules which appear to be acting directly on rhodopsin in these assays, or variations on these assays readily apparent to the person of skill in the art are taken to the next level of testing. The small molecules also are assayed for the ability to modulate rhodopsin-transducin signaling specifically without affecting processes mediated by other GPCRs.

Preferred small molecule "enhancers" and "inhibitors" are uniquely specific, not only for the receptor, but for the receptor-G protein interaction. As there are over 1000 GPCRs, and no simple way to determine the effect of compounds on each and every one of them individually, a few select and representative GPCR signaling systems may be tested. Functional coupling of the human thrombin receptor (PAR1) with Gt has been demonstrated. Seibert, *Eur. J. Biochem.* 266(3):911-916, 1999. Testing for effects on PAR1 may include determining if the small molecule(s) have an effect on thrombin-mediated signal transduction events such as adenylyl cyclase activity, calcium influx, and inositol phosphate accumulation. Other tests for functional coupling to PAR1 or other GPCRs are known in the art and may be used as well.

Adenylyl cyclase activity may be measured in a final volume of 50 μl with [α-$^{32}$P]ATP (1 mM; 120-400 cpm/pmol) as the substrate and [2,8-$^{3}$H]cAMP (2 mM; 200,000 cpm/pmol) to monitor recovery in an assay mixture containing 5 mM MgCl₂, 1 mM EDTA, 1 mM 2-mercaptoethanol, 100 μM papaverine, 1 μg/ml bovine serum albumin, and an ATP-regenerating system consisting of 20 mM creatine phosphate and 120 units creatine phosphokinase/ml in 25 mM Tris-HCl buffer, pH 7.5. The concentration of ATP and cAMP may be determined spectrophotometrically at 259 nm, using ε values of 15.4 and 14.6 mM$^{1}$ cm$^{-1}$, respectively. The assay may be initiated by addition of protein and after a 10 min incubation at 37° C. the reaction is stopped with 2 volumes stop solution (2% SDS/45 mM ATP/13 mM cAMP). The samples then may be heated (e.g. to 100° C. for 3 minutes) and the formed cyclic [α-$^{32}$P]AMP recovered. See Gilchrist et al., *J. Biol. Chem.* 276:25672-25679, 2001, the disclosures of which are hereby incorporated by reference. Finally, the compounds passing the previous steps may be tested in an animal model of night blindness as described by Chang et al., *Vision Res.* 42:517-525, 2002, the disclosures of which are hereby incorporated by reference.

To assess the effects of small molecules on photoresponses in an in vivo system, electroretinography of mice exposed to the small molecule(s) may be used to measure the amplitude of both the a- and b-waves. Plots of the amplitude against the logarithm of relative light intensities indicate if the compounds are affecting only rod signaling. The sensitivity for eliciting a threshold b wave within normal limits also may be measured. Mutant animals also may be tested to observe not only the effects of enhancers on wild type rhodopsin signaling, but also the effects on animals with night blindness.

The small molecules to be tested may be dissolved in sterile PBS and administered as eye drops. Experiments may be repeated using IV or IM injections if initial results are negative. The most promising candidates undergo the steps needed to take them from an identified compound to a lead compound. This approach identifies a pharmacological treatment for night blindness which circumvents the need for more invasive procedures such as gene therapy, laser ablation and retinal replacement.

Mapping the sites of interaction between proteins involves identifying parts of the interface between two proteins using synthetic peptides corresponding to interfacial regions. The peptides are identified because they act as competitive inhibitors of the interaction. NMR studies of peptide structures in their bound conformation using trNOESY, combined with analysis of activity of substituted peptide analogs to define the minimal structural requirements for interaction were used to understand the structural basis of rhodopsin-transducin interaction as well as G protein-effector interaction. Peptides corresponding to the C-terminus of Gt can be used to stabilize rhodopsin in its active conformation (MII) or in an inactive conformation. The 3-dimensional structures of heterotrimeric G proteins reveals that the last 7 amino acids of G protein α subunits are unstructured, indicating that this region of the α subunit is critical for binding to the cytoplasmic surface of an activated receptor with induced fit. This interaction is quite specific since a difference in a single amino acid can affect the affinity by 1000 fold.

High throughput screening is a recent technology that has been developed primarily within the pharmaceutical industry. It has emerged in response to the profusion of new biological targets and the need of the pharmaceutical industry to generate novel drugs rapidly in a changed commercial environment. Its development has been aided by the invention of new instrumentation, by new assay procedures, and by the availability of databases that allow huge numbers of data points to be managed effectively. High throughput screening combined with combinatorial chemistry, rational design, and automation of laboratory procedures has led to a significantly accelerated drug discovery process compared to the traditional one-compound-at-a-time approach. Screens may be performed manually, however robotic screening of the compound libraries is preferred as a time- and labor-saving device.

One critical aspect of the drug discovery process is the identification of potent lead compounds. A purely random selection of compounds for testing is unlikely to yield many active compounds against a given receptor. Typically, pharmaceutical companies screen 100,000 or more compounds per screen to identify approximately 100 potential lead compounds. On average, only one or two of these compounds actually produce lead compound series. Therefore, companies have been assaying larger and larger data sets in the search for useful compounds. Compound accessibility then becomes an issue: historical compound collections are limited in size and availability. In contrast, large combinatorial chemistry libraries can be synthesized on demand, but at significant technical difficulty and cost. As the library sizes expand, the difficulty becomes selecting the desired compounds from these very large combinatorial libraries. When literally hundreds of thousands of compounds are screened, it makes characterizing the candidate lead compounds an expensive and time-consuming process, particularly when many of the "hits" turn out to be false positives.

The multi-step approach to the drug discovery process described here provides a solution to many of these problems. One embodiment of this invention takes advantage of the properties of G protein α subunit carboxyl termini to identify peptides which act as high affinity, competitive inhibitors or agonists of G protein/GPCR interactions. The method, however, can be used with any specific protein-protein, protein-small molecule, protein-nucleic acid interaction or the like. In addition, peptides based on any region of a Gα subunit or any region of a Gβγ dimer which is involved in GPCR binding may be used in the same way. Many such GPCR binding regions are known in the art. The identification of high affinity competitors forms a first step in a screening and selection method which overcomes many of the disadvantages of high throughput screening by providing specific, high affinity lead compounds against which to test potentially useful pharmaceuticals. Because peptides selected by this method have affinity for their binding partner up to 1,000 times higher or more than the native protein, this step is one key to successfully screening and identifying useful pharmaceutical compounds.

A subsequent step of the preferred process involves high throughput screening of candidate peptide or small molecule pharmaceutical compounds against the high affinity lead peptides identified in the first step. Because the lead peptide compounds are potent and specific binders to the desired receptor, screening assays test for compounds that can decrease the binding of the peptide ("blockers") or that increase the binding of the peptide ("agonists"). The assay system allows one to measure both binding and function simultaneously as the peptides all serve to mimic a required step, that of specific receptor-G protein binding. By using this site, the system facilitates identification of those candidate compounds which bind not only with useful affinities (nM to μM range) but by the very virtue of their selection process will affect function by either increasing or decreasing the G protein binding. The high throughput screening step of the drug discovery process is thereby greatly simplified, because the number of false positive compounds, and compounds which are identified as binders but which bind only with low affinity, is reduced or virtually eliminated. Only those compounds with a high chance of success will be identified by the screen, therefore useful compounds can be identified directly and there are many fewer compounds which need to be characterized and further studied to confirm that the compounds are specific, potent pharmaceutical compounds. In addition, the method identifies a compound through binding directly to the precise site of interest, so that the mechanism of binding and the mechanism of action of the newly identified pharmaceutical compound does not have to be discovered and confirmed later by a separate process.

The identified high affinity peptides also may be used according to the inventions to identify GPCR inverse agonists. High affinity peptides identified in a first step of the inventive method bind the receptor and stabilize it in an active or R* conformation. Screens which are used to identify potent agonists seek out compounds which can compete with this binding and also stabilize the GPCR in its R* state. Inverse agonists, on the other hand, stabilize the GPCR in an inactive or R state. Therefore, screens designed to detect dissociation of the high affinity peptide or a decrease in its affinity for the GPCR are used to identify inverse agonists.

Although this description provides examples relative to the interaction between a G protein coupled receptor and its cognate Gα protein, the methodology can be used to identify peptide inhibitors of most protein-protein interactions, specifically including any interaction between a GPCR and any region of a Gα or Gβγ G protein subunit. The high affinity peptides selected by this method may be used in high throughput screening to identify small molecules that can be used as modulators of a variety of specific biological process.

To produce very high affinity peptide GPCR blockers, the tertiary structure of a wild-type Gα carboxyl terminal peptide or any other GPCR binding peptide in its receptor-bound conformation may be studied, for example, using trNOESY (NMR). Dratz et al., *Nature* 363:276-280, 1993. Structural data derived from these types of studies of G protein regions are combined with analysis of activity of substituted peptide analogs to define the minimal structural requirements for interaction of peptides or any ligand with GPCR. The following experimental systems are examples of systems which can be used to define receptor-G protein interactions: (i) rhodopsin-transducin (Gαt) in retinal rod cells, (ii) β-adrenergic receptor-Gαs in C6 glioma cells, (iii) adenosine A1 receptor-Gαl in Chinese hamster ovary cells, (iv) GABA$_B$ receptors-Gαl in rat hippocampal CA1 pyramidal neurons, (v) muscarinic M2 receptor-Gαl in human embryonic kidney cells, and the like. Any GPCR or group of GPCR which is convenient or desired can be used to define the interaction requirements, and skilled workers are aware of many methods to understand structure-activity relationships in receptor binding of this kind. Any of these methods are contemplated for use in these methods and may substitute for the particular methods of the exemplified embodiment.

The plasmid display method provides an efficient means of identifying specific and potent peptides that can serve as competitive inhibitors of protein-protein interactions. Using the information gleaned from structure-activity studies, a library of variant peptides encoding sequences related to a GPCR-binding region, for example the Gα subunit carboxyl terminus, for each of the classes of the Gα subtypes or Gβγ can be prepared. Exemplary native sequences upon which libraries may be based include those listed in Table III, below. Libraries advantageously contain peptides with computer-generated random substitutions within the sequence, and allow one to test a large number of peptide sequences at one time. Preferably, peptide sequences in each library are constructed such that approximately 50% of the amino acid residues are identical to the native GPCR binding region and the remaining amino acid residues are randomly selected from any amino acid. The peptides may range in size from about 7 to about 55 amino acid residues or from about 8 to about 50 amino acids long or from about 7 to about 70 amino acid residues or longer, preferably from about 9 to about 23 amino acid residues or about 9 to about 15 amino acid residues. Undecamer peptides are most preferred. Libraries may be constructed in which about 10% to about 90% of the amino acid residues unchanged from the native sequence; however, about 30% to about 70% unchanged is preferred and about 50% is most preferred.

Alternatively, a synthetic peptide library can be based on any protein known to interact with a GPCR, using randomly created overlapping regions of the protein. The peptides may be about 7-70 amino acids long or about 8-50 amino acids long or preferably about 9 to about 23 or about 9 to about 15 amino acids long and most preferably about 11 amino acids long. Oligonucleotides encoding the peptides advantageously may be cloned to the 3' end of the LacI gene, with a linker sequence at the N-terminus of the peptide. The linker sequence is not mandatory for successful screening, but is generally preferred. Restriction enzyme sites may be placed at either end of the peptide coding sequence for cloning purposes. See Table I below for a schematic representation of a peptide library and an example of one peptide. Additional peptides which also can be used are shown in Tables II and III, below. The oligonucleotides encoding the actual peptide sequences are synthesized with 70% of the correct base and 10% each of the remaining bases, leading to a biased peptide library with an approximately 50% chance of having the correct amino acid at any specific position along the peptide sequence. Different ratios of bases may be used to achieve the desired mutagenesis rate at any particular position in the sequence.

TABLE I

Example for Construction of a Synthetic Peptide Library.

```
                        Q   R   M   H   L   R   Q   Y   E   L   L (SEQ ID NO:13)
gaggtggt nnknnknnknnk attcgtgaaaacttaaaagattgtggtcgtttc taa ctaagtaaagc
   A        B                      C                     D       E
```

(SEQ ID NO:14) n = any nucleotide base; k = guanidine or thymidine; A = restriction enzyme site; B = linker sequence; C = oligonucleotide encoding peptide sequence; D = stop codon; E = restriction enzyme site.

TABLE II

Gα Subunit Peptides and Corresponding DNA Constructs.

| Gα Subunit | Sequence | | | | | | | | | | | SEQ ID NO: |
|---|---|---|---|---|---|---|---|---|---|---|---|---|
| Gt | I | K | E | N | L | K | D | C | G | L | F | 15 |
|  | atc | aag | gag | aac | ctg | aaa | gac | tgc | ggc | ctc | ttc | 16 |
| Gi1/2 | I | K | N | N | L | K | D | C | G | L | F | 17 |
|  | ata | aaa | aat | aat | cta | aaa | gat | tgt | ggt | ctc | ttc | 18 |

TABLE II-continued

Gα Subunit Peptides and Corresponding DNA Constructs.

| Gα Subunit | Sequence | | | | | | | | | | SEQ ID NO: |
|---|---|---|---|---|---|---|---|---|---|---|---|
| GRi1/2 | N | G | I | K | C | L | F | N | D | K | L | 19 |
| | aac | ggc | atc | aag | tgc | ctc | ttc | aac | gac | aag | ctg | 20 |
| Gi3 | I | K | N | N | L | K | E | C | G | L | Y | 21 |
| | att | aaa | aac | aac | tta | aag | gaa | tgt | gga | ctt | tat | 22 |
| Go2 | I | A | K | N | L | R | G | C | G | L | Y | 23 |
| | atc | gcc | aaa | aac | ctg | cgg | ggc | tgt | gga | ctc | tac | 24 |
| Go1 | I | A | N | N | L | R | G | C | G | L | Y | 25 |
| | att | gcc | aac | aac | ctc | cgg | ggc | tgc | ggc | ttg | tac | 26 |
| Gz | I | Q | N | N | L | K | Y | I | G | L | C | 27 |
| | ata | cag | aac | aat | ctc | aag | tac | att | ggc | ctt | tgc | 28 |
| G11 | L | Q | L | N | L | K | E | Y | N | L | V | 2 |
| | ctg | cag | ctg | aac | ctc | aag | gag | tac | aac | ctg | gtc | 29 |
| Gq | L | Q | L | N | L | K | E | Y | N | A | V | 30 |
| | ctc | cag | ttg | aac | ctg | aag | gag | tac | aat | gca | gtc | 31 |
| Golf | Q | R | M | H | L | K | Q | Y | E | L | L | 32 |
| | cag | cgg | atg | cac | ctc | aag | cag | tat | gag | ctg | ttg | 33 |
| G14 | L | Q | L | N | L | R | E | F | N | L | V | 34 |
| | cta | cag | cta | aac | cta | agg | gaa | ttc | aac | ctt | gtc | 35 |
| G15/16 | L | A | R | Y | L | D | E | I | N | L | L | 36 |
| | ctc | gcc | cgc | tac | ctg | gac | gag | atc | aac | ctg | ctg | 37 |
| G12 | L | Q | E | N | L | K | D | I | M | L | Q | 38 |
| | ctg | cag | gag | aac | ctg | aag | gac | atc | atg | ctg | cag | 39 |
| G13 | L | H | D | N | L | K | Q | L | M | L | Q | 40 |
| | ctg | cat | gac | aac | ctc | aag | cag | ctt | atg | cta | cag | 41 |
| Gs | Q | R | M | H | L | R | Q | Y | E | L | L | 13 |
| | cag | cgc | atg | cac | ctt | cgt | cag | tac | gag | ctg | ctc | 42 |
| 5'-gatccgccgccaccatggga- | | | | | | | | | | | -tgaa-3' | |

(SEQ ID NOS:43, 44)

TABLE III

Exemplary Native G Protein Sequences for Library/Minigene Construction.*

| Name | Sequence | SEQ ID NO: |
|---|---|---|
| hGt | IKENLKDCGLF | 15 |
| hGi1/2 | IKNNLKDCGLF | 17 |
| G05_DRO | IKNNLKQIGLF | 45 |
| GAF_DRO | LSENVSSMGLF | 46 |
| Gi-DRO | IKNNLKQIGLF | 45 |
| hGi3 | IKNNLKECGLY | 21 |
| hGO-1 | IANNLRGCGLY | 25 |
| hGO-2 | IAKNLRGCGLY | 47 |
| GAK_CAV | IKNNLKECGLY | 21 |
| G0_XEN | IAYNLRGCGLY | 48 |
| GA3_CAEEL | IQANLQGCGLY | 49 |
| GA2_CAEEL | IQSNLHKSGLY | 50 |
| GA1_CAEEL | LSTKLKGCGLY | 51 |
| GAK_XEN | IKSNLMECGLY | 52 |
| GA1_CAN | VQQNLKKSGIM | 53 |
| hGZ | IQNNLKYIGLC | 27 |
| hG15 | LARYLDEINLL | 36 |
| GA2_SCHPO | LQHSLKEAGMF | 54 |
| hG12 | LQENLKDIMLQ | 38 |
| hG13 | LHDNLKQLMLQ | 40 |
| GAL_DRO | LQRNLNALMLQ | 55 |
| GA2_YST | ENTLKDSGVLQ | 56 |
| hG14 | LQLNLREFNLV | 34 |
| hG11 | LQLNLKEYNLV | 2 |
| hGQ | LQLNLKEYNAV | 30 |
| GQ_DROME | LQSNLKEYNLV | 57 |
| G11_XEN | LQHNLKEYNLV | 58 |
| Gq_SPOSC | IQENLRLCGLI | 59 |
| GA1_YST | IQQNLKKIGII | 60 |
| GA1_NEUCR | IIQRNLKQLIL | 61 |
| CryptoGba1 | LQNALRDSGIL | 62 |
| GA3_UST | LTNALKDSGIL | 63 |
| GA1_KLU | IQQNLKKSGIL | 64 |
| GA3_UST | LTNALKDSGIL | 63 |
| GA1_DIC | NLTLGEAGMIL | 64 |
| GA2_KLU | LENSLKDSGVL | 65 |
| GA2_UST | ILTNNLRDIVL | 66 |
| Mgs-XL | QRMHLPQYELL | 67 |
| hGs | QRMHLRQYELL | 13 |
| hGolf | QRMHLKGYELL | 68 |
| GA1_COPCO | LQLHLRECGLL | 69 |
| GA1-SOL | RRRNLFEAGLL | 70 |
| GA2_SB | RRRNLLEAGLL | 71 |
| GA1_SB | RRRNPLEAGLL | 72 |
| GA1_UST | IQVNLRDCGLL | 73 |
| GA4_UST | RENLKLTGLVG | 74 |
| GA1_ORYSA | DESMRRSREGT | 75 |
| GQ1_DROME | MQNALKEFNLG | 76 |
| GA2_DIC | TQCVNKAGLYS | 77 |
| GS-SCH | LQHSLKEAGMF | 54 |
| GA-SAC | ENTLKDSGVLQ | 56 |
| GA1-CE | IISASLKMVGV | 78 |
| GA2-CE | NENLRSAGLHE | 79 |
| GA3-CE | RLIRYANNIPV | 80 |
| GA4-CE | LSTKLKGCGLY | 51 |
| GA5-CE | IAKNLKSMGLC | 81 |
| GA6-CE | IGRNLRGTGME | 82 |
| GA7-CE | IQHTMQKVGIQ | 83 |
| GA8-CE | IQKNLQKAGMM | 84 |
| GA5-DIC | LKNIFNTIINY | 85 |

*For production of minigene constructs each nucleotide sequence should be constructed to encode the amino acids MG at the N-terminus of the peptide by using 5'-gatccgccgccaccatggga-(SEQ ID NO:43) and -tgaa-3' (SEQ ID NO:44).

The peptides advantageously are synthesized in a display system for convenience and efficiency of performing the binding reactions. For example, plasmid or phage display systems, as are known in the art, may be employed. While peptide display systems are preferred, any method which allows efficient contact of the peptides with a GPCR and determination of binding may be used.

A peptide display ("peptides on plasmids") library is a convenient system for use with this invention which exploits the high affinity bond between LacI and lacO. The "peptides on plasmids" display is preferred for use with this invention for two major reasons. The technique is easily set up in the laboratory. In addition, the fusion of the peptide at the carboxyl terminus of the presenting protein mimics the normal presentation for carboxyl terminal peptides during the screen. If amino terminal or interior peptides are being tested, the peptide may be cloned at the appropriate position to mimic native presentation.

The "peptides on plasmids" method for testing carboxyl terminal peptides generally works as follows. Persons of skill in the art will be able to modify these methods as needed to accommodate different conditions using this general description and the examples below as a guide. A library of peptides is created by degenerate PCR based on the native GPCR-binding peptide of interest and fused to the carboxyl terminus of LacI. The peptide library is expressed via a plasmid vector carrying the fusion gene. The plasmid also contains the Lac operon (LacO), and when $E.$ $coli$ transcribes and translates the LacI fusion protein, it binds back as a tetramer to the encoding plasmid through its lacO DNA binding sequence, displaying the inserted sequences of interest on the plasmid. Following transcription and translation, variant peptides encoding different sequences related to the native peptide sequence therefore are displayed as carboxyl terminal extensions of the lacI gene. Thus, a stable LacI-peptide-plasmid complex is formed which can be screened for binding to receptor. Methods described in Gates et al., $J.$ $Mol.$ $Biol.$ 255:373-386, 1996, the disclosures of which are hereby incorporated by reference, are suitable. See Examples 7 and 9 for exemplary methods.

The $E.$ $coli$ strain used to display the peptides was ARI814, which has the following genotype: Δ(srl-recA) endA1 nupG lon-11 sulA1 hsdR17 Δ (ompT-fepC) 266 ΔclpA319::kan ΔlacI lacZU118. The strain contains the hsdR17 allele that prevents restriction of unmodified DNA introduced by transformation or transduction. The ompT-fepC deletion removes the gene encoding the OmpT protease, which digests peptides between paired basic residues. The lon-11 and clpA mutations also limit proteolysis by ATP-dependent, cytoplasmic proteases. The deletion of the lacI gene prevents expression of the wild-type lac repressor, which would compete with the fusion constructs for binding to the lacO sites on the plasmid. The lacZ mutation prevents waste of the cell's metabolic resources to make β-galactosidase in the absence of the repressor. The endA1 mutation eliminates a nuclease that has deleterious effects on affinity purification and the recA deletion prevents multimerization of plasmids through RecA-catalyzed homologous recombination. This strain was selected also for its robust growth properties and high yields of immunocompetent cells. Transformation efficiencies of $2\times10^{10}$ colonies per mg DNA typically were achieved. Although this strain of $E.$ $coli$ is preferred, those of skill in the art are aware of many alternatives which are convenient for use with the methods described. Therefore, any suitable and convenient bacterial strain known in the art is contemplated for use with this invention.

The LacI-peptide fusion protein library may be released from the bacteria by gentle enzymatic digestion of the cell wall using lysozyme. After pelleting the cell debris, the lysate then can be added directly to immobilized receptor for affinity purification or used without purification. The display library of these peptides is screened to identify those peptides which bind with high affinity to a particular GPCR. In this way, it is possible to screen for and identify high affinity peptides which bind GPCR and can interfere with or enhance activation of the pre-selected specific G protein. The library can be screened against any desired GPCR. Since the combinatorial library contains peptides based on a particular Gα or Gβγ subunit, any GPCR which binds to or mediates signaling through that subunit or class of subunits can be used. Multiple libraries, based on the carboxyl terminal sequences or other regions of different G protein subunits may be constructed for screening the same or different GPCR.

To screen the plasmid display library, a G protein coupled receptor of interest advantageously may be immobilized on microtiter plates for screening by ELISA. A plasmid preparation (bacterial lysate) then may be added to the wells. This screening procedure, involving allowing the peptides displayed on the library plasmids to bind receptor, is sometimes referred to as "panning." Sequences that bind the receptor stick to the well so that non-binding sequences can be removed by a washing step. The adherent plasmids then can be expanded and used to transform $E.$ $coli$. The "panning" process generally is repeated 2 to 8 times. In general, however, 3 to 4 sequential screens are sufficient and preferred. In the later rounds of panning, parent peptide (wild type sequence) preferably is co-incubated with the plasmid preparation to bind receptors and serve as a competitive inhibitor. In this way, only high affinity sequences on the display library are captured by the immobilized receptor. The same competitive inhibition advantageously may be performed using a high affinity peptide or small molecule which has already been identified, rather than the native peptide. See FIG. 1 for a schematic diagram generally describing the "panning" procedure and Example 7 for a specific embodiment. The selection process in this embodiment preferably is carried out in low salt buffers because high salt concentrations destabilize the LacI-lacO complex, and could lead to peptides becoming associated with the incorrect plasmid. For the same reason, the panning buffers preferably contain lactose, which causes the LacI to bind more tightly to lacO.

The selection process of this invention allows the identification of peptide sequences with higher and higher affinity binding with each round of panning. For example, diversity in an unpanned library may look like the sequences given in Table IV, below, i.e. highly randomized. After successive rounds of selection, the selected adherent peptides would look more like those given in Table V, below.

TABLE IV

Diversity in Unpanned Gq Library.

| | | SEQ. ID NO. |
|---|---|---|
| Native | LQLNLKEYNLV | 2 |
| clone #1 | LLLQLVEHTLV | 86 |
| clone #2 | HRLNLLEYCLV | 87 |
| clone #3 | EQWNMNTFHMI | 88 |
| clone #4 | SQVKLQKGHLV | 89 |
| clone #5 | LRLLL*EYNLG | 90 |
| clone #6 | RRLKVNEYKLL | 91 |
| clone #7 | LQLRLREHNLV | 92 |
| clone #8 | HVLNSKEYNQV | 93 |

TABLE V

Selection in Panned Gα11 Library.

|  |  | SEQ ID NO. |
|---|---|---|
| Native | LQLNLKEYNLV | 2 |
| Round 1 |  |  |
| 1 | MKLNVSESNLV | 94 |
| 2 | LQTNQKEYDMD | 95 |
| 3 | LQLNPREDKLW | 96 |
| 4 | RHLDLNACNMG | 97 |
| 5 | LR*NDIEALLV | 98 |
| 6 | LVQDRQESILV | 99 |
| Round 2 |  |  |
| 1 | LQLKHKENNLN | 100 |
| 2 | LQVNLEEYHLV | 101 |
| 3 | LQFNLNDCNLV | 102 |
| 4 | MKLKLKEDNLV | 103 |
| 5 | HQLDLLEYNLG | 104 |
| 6 | LRLDFSEKQLV | 105 |
| Round 3 |  |  |
| 1 | LQKNLKEYNMV | 106 |
| 2 | LQYNLMEDYLN | 107 |
| 3 | LQMYLRGYNLV | 108 |
| 4 | LPLNPKEYSLV | 109 |
| 5 | MNLTLKECNLV | 110 |
| 6 | LQQSLIEYNLL | 111 |

LacI is normally a tetramer and the minimum functional DNA binding species is a dimer. Thus, the peptides are displayed multivalently on the fusion protein, leading to binding to the immobilized receptor in a cooperative fashion. This cooperative binding permits the detection of binding events of quite low intrinsic affinity. The sensitivity of the assay is an advantage in that initial hits of low affinity can be identified, but the disadvantage is that the signal in the ELISA does not necessarily correlate with the intrinsic affinity of the bound peptides.

One preferred ELISA, where signal strength is better correlated with affinity, involves fusing the sequences of interest from a population of clones in frame with a gene encoding a protein, for example E. coli maltose binding protein (MBP). Once the sequences have been transferred into the monomeric fusion protein, they can be overexpressed in E. coli and used as either crude lysates or purified fusion proteins for assay by an ELISA which detects the protein bound to receptor or any convenient assay. Controls having the vector alone which expresses TGGG linker only fused to MBP, or having Gt:340-350K341R peptide fused to MBP may be used, if desired. Frozen cell stocks preferably are kept in 25% glycerol at −80° C. The high affinity Gα peptides fused to MBP preferably are analyzed by ELISA, where the resulting signal correlates to the peptide's affinity for light-activated rhodopsin. The MBP-peptide fusions are expressed and purified over an amylose affinity column and used to measure the relative affinities of peptides of interest. Those samples with an absorbance of at least two standard deviations above background may be considered to contain high affinity binding peptides. Any desired cut-off point may be used, however, depending on the assay parameters and the needs of the operator.

A suitable ELISA may be performed as follows, however those of skill in the art will be able to modify the techniques for the conditions in their assays. Serial dilutions of MBP-peptide fusion proteins are added to 96-well plates with immobilized light-activated rhodopsin previously blocked with 0.1% BSA. After 1 hour at 37° C., the wells are washed with phosphate buffered saline (PBS)/0.1% Tween 20, and probed with an anti-MBP antibody, followed by a goat-anti-rabbit antibody conjugated to horseradish peroxidase. Color development of the assay is allowed to proceed for 20 minutes, after which the $A_{450}$ is measured on a microtiter plate reader. See Gilchrist et al., Methods Enzymol. 315: 388-404, 2000, the disclosures of which are hereby incorporated by reference.

The purified fusion proteins can be further tested by measuring their ability to compete for the site of binding on the receptor using native peptide, a LacI-peptide fusion protein, or heterotrimeric G protein. Use of competitive ELISA allows one to calculate $IC_{50}$ values for the binding of individual fusion protein to the immobilized receptor.

Peptide fusion proteins can be analyzed in a competitive ELISA format using a fusion protein co-incubation to prevent the binding of lower affinity peptide fusion proteins to the GPCR. Any convenient protein which does not interfere with peptide binding may be used, including for example, glutathione-S-transferase, green fluorescent protein or ubiquitin, however a maltose binding protein fusion protein such as MB-Gα$_t$340-350K341R is preferred. Competitive ELISA indicates which peptide sequences have the highest affinity for light activated rhodopsin. Several different assay formats are suitable. For example, synthetic Gt:340-350K341R peptide may be used to compete with the MBP fusion proteins containing the Gα high affinity peptides for binding. In addition, MBP fusion proteins containing the Gα high affinity peptides may be used to compete with LacI-Gt:340-350K341R peptide fusion protein for binding to light-activated rhodopsin. Recombinant heterotrimeric Gt also may be tested against the high affinity peptides. The relative affinity of the variant peptides may be assessed using an ELISA format where a constant concentration of MBP-Gα peptide fusion proteins is competed by serial dilutions of native peptide, LacI-Gαt peptide fusion protein or recombinant heterotrimeric Gt. The wells advantageously may be probed with an anti-MBP antibody to measure the amount of MBP-Gα peptide fusion protein remaining bound. The dose-response curves may be analyzed by non-linear regression to calculate an $EC_{50}$.

Cloning the library into pJS142 creates a BspEI restriction site near the beginning of the random coding region of the library. Conveniently, digestion with BspEI and ScaI allows the purification of a 900 base pair DNA fragment that may be subcloned into pELM3, a vector that directs the MBP fusion protein to the cytoplasm, a reducing environment. Alternatively, the fragment can be cloned into pELM15, a vector which directs the MBP fusion protein to the periplasm, an oxidizing environment. pELM3 and pELM15 are simple modifications of the pMALc2 and pMALp2 vectors, respectively, available commercially (New England Biolabs). Digestion of pELM3 with AgeI and ScaI allows efficient cloning of the BspEI-ScaI fragment from the pJS142 library. Any suitable method may be used which is convenient to achieve the desired result. Modifications of these methods are well known by those of skill in the art of molecular biology and are contemplated for use here.

Proof that the high affinity peptides competitively bind to GPCR and interfere with or enhance its recognition of G protein can be obtained using a competitive binding assay in the presence of a heterotrimeric G protein. For example, if rhodopsin is the GPCR used in the screen, heterotrimeric G protein, transducin (Gt) may be used. Gt binds rhodopsin with multiple epitopes and is membrane-bound via myristoylation of the α subunit and farnesylation of the α subunit carboxyl terminus. Poor binding by carboxyl terminal native peptide LacI constructs and/or heterotrimeric Gt indicates high affinity binding of the MBP-peptide fusion proteins. An analogous strategy of panning, peptide synthesis and binding studies may be employed for determining high affinity peptides that bind any GPCR, for example the thrombin receptors (PAR1, PAR3, PAR4), dopamine receptors (D1, D2, D3, D4, D5), vasopressin receptors (V1a, V1b, V2) and histamine receptors (H1, H2, H3), using carboxyl terminal peptide libraries for any Gα subunit, for example Gαi, Gαs and Gαq. Once peptide analogs with higher binding affinities have been elucidated, they can be exploited to inhibit GPCR-G protein interaction.

The peptides selected by this method, characterized by high affinity, specific blockade of or enhancement of a desired GPCR-mediated signaling event, may be used as therapeutic agents such as traditional pharmaceuticals or gene therapies to treat disorders which would benefit by modifying GPCR activity or used to screen additional libraries of compounds able to compete with the high affinity peptide analogs or to modulate (i.e., increase or decrease) the binding affinity of the high affinity peptide analogs or the high affinity peptide analog-fusion proteins.

Any method known in the art for selecting and synthesizing small molecule libraries for screening is contemplated for use in this invention. Small molecules to be screened are advantageously collected in the form of a combinatorial library. For example, libraries of drug-like small molecules, such as β-turn mimetic libraries and the like, may be purchased from for example ChemDiv, Pharmacopia or Combichem or synthesized and are described in Tietze and Lieb, *Curr. Opin. Chem. Biol.* 2:363-371, 1998; Carrell et al., *Chem Biol.* 2:171-183, 1995; U.S. Pat. No. 5,880,972, U.S. Pat. No. 6,087,186 and U.S. Pat. No. 6,184,223, the disclosures of which are hereby incorporated by reference.

Any of these libraries known in the art are suitable for screening, as are random libraries or individual compounds. In general, hydrophilic compounds are preferred because they are more easily soluble, more easily synthesized, and more easily compounded. Compounds having an average molecular weight of about 500 often are most useful, however, compounds outside this range, or even far outside this range also may be used. Generally, compounds having c logP scores of about 5.0 are preferred, however the methods are useful with all types of compounds. Simple filters like Lipinski's "rule of five" have predictive value and may be used to improve the quality of leads discovered by this inventive strategy by using only those small molecules which are bioavailable. See Lipinski et al., *Adv. Drug Delivery Rev.* 23:3-25, 1997.

Combinatorial chemistry small molecule "libraries" can be screened against drug targets. The idea is that diversity of chemical structures increases the chances of finding the needle in the $10^{200}$ possible small organic molecule haystack. These collections provide an excellent source of novel, readily available leads. For example, ChemDiv uses more than 800 individual chemical cores, a unique Building Block Library, and proprietary chemistry in designing its Diversity Collections (small molecule libraries) to assemble 80,000-100,000 compounds a year. CombiLab lead library sets of 200-400 compounds also can be produced as a follow-up. In addition, ChemDiv's compounds are designed to ensure their similarity to drugs adjusted according to proprietary algorithms of "drug-likeness definitions" (group similarity and advanced neural net approaches), and a variety of intelligent instruments for ADME&T (Absorption, Distribution, Metabolism, Excretion and Toxicity) properties prediction, such as partition coefficient, solubility, dissociation coefficients, and acute toxicity.

Thus, focused synthesis of new small molecule libraries can provide a variety of compounds structurally related to the initial lead compound which may be screened to choose optimal structures. Preferably, a library of compounds is selected that are predicted to be "drug-like" based on properties such as pKa, log P, size, hydrogen bonding and polarity. The inventive multi-step approach which yields high affinity peptides in the first step, and small molecules in a subsequent step reduces the number of artificial hits by eliminating the lower affinity small molecules that would be selected and have to be assayed in a normal high throughput screening method. In addition, it focuses the search for molecules that can modulate the binding of a peptide the mimics the G protein rather than screening for binding to any site on the receptor. Other advantages of this technology are that it is simple to implement, amenable to many different classes of receptors, and capable of rapidly screening very large libraries of compounds.

Screening of the peptides or small molecules may be performed conveniently using receptors from any source. Generally, it is convenient to purify receptor from cells and reconstitute the receptor in lipid vesicles or to use membranes isolated from insect or mammalian cells that express or overexpress the receptor. PAR1 and rhodopsin are convenient receptors, however any suitable receptor is contemplated for use with this invention. The receptors used for screening may be purified from a natural source or purified from cells which overexpress the receptor and reconstituted in lipid vesicles. Membranes containing the receptor may be prepared from cells which natively express the receptor, for example Sf9 cells which express PAR1, or from cells which have been genetically engineered to express the receptor, for example mammalian or insect cells overexpressing PAR1. Peptides identified from screening a receptor (PAR1) expressed by three different methods are shown in Tables XI, XII, and XIII. The results indicate the methods give similar results showing a high degree of conservation, (N348;L349) being identified for all three methods of receptor expression. Initially, it is advantageous to determine the binding affinity of the peptide fusion protein or high affinity peptide against which the peptides or small molecules are screened. This allows the amount of receptor and peptide MBP peptide fusion protein or small molecule in the assay to be optimized.

Generally, it is convenient to test the libraries using a one well-one compound approach to identify compounds which compete with the peptide fusion protein or high affinity peptide for binding to the receptor. A single compound per well can be used, at about 1 µM each or at any convenient concentration depending on the affinity of the receptor for the compounds and the peptide against which they are being tested. Compounds may be pooled for testing, however this approach requires deconvalution. Compounds may be pooled in groups of about 2 to about 100 compounds per well, or more, or about 10 to about 50 compounds per well at about 10 nM each or at any convenient concentration depending on the affinity of the receptor for the compounds being tested. Several different concentrations may be used if desired. Peptides desirably are screened using a pooled approach because of the layer members of peptides which are screened in the first instance. Peptides may be screened individually as well, but preferably are screened in pools of about $10^4$-$10^{12}$ peptides per well or about $10^8$-$10^{10}$ peptide per well or most preferably about $10^9$ peptides per well.

ELISA, or any other convenient assay, such as fluorescence assays or radioimmunoassay may be used to determine (1) if one or more peptides in each well reduce the amount of binding by the high affinity peptide fusion protein or high affinity peptide, or (2) if one or more peptides in each well bind to the receptor. Compounds may be tested at a series of concentrations as well, and this generally is preferred if the affinity of the peptide or peptide fusion protein is not known. In an ELISA, wells in which the $OD_{450}$ is half or less than half than that of control wells (no tested compounds) generally are considered "positive" and may be further studied. Any suitable cut-off point may be used, however, depending on the assay components and the goals of the assay.

Screening against the high affinity peptide analogs can be performed using the desired GPCR immobilized onto microtiter wells, biochips, or any convenient assay surface. Binding assays performed in solution also are suitable. One, several, or thousands of candidate small molecule pharmaceutical compounds can be screened for binding to the receptor in the presence or absence of a high affinity peptide analog. The assays preferably are performed in the presence of a high affinity binding peptide to ensure that only those candidate compounds which can successfully compete for binding against the high-affinity binding peptide will be captured by the receptor. Alternatively, organic compounds or small molecules which have been identified by screening as competitively binding in the presence of a high affinity peptide analog also may be used as lead compounds in screening for further small molecule candidate compounds with even higher affinity. In either screening process, binding may be detected by any convenient method, for example by ELISA, fluorescence assays or radioimmunoassays.

By using a two-step protocol to identify compounds which block G protein signaling, high throughput screening of compounds and characterization of the selected compounds is significantly reduced in both time and cost, because only potent and strongly binding compounds are selected. The first step of identification of high affinity peptides which strongly compete with G proteins for their site of binding on G protein-coupled receptors insures this because the high affinity peptides are designed and tested for the particular desired binding specificity, ability to modify function within a cellular system and ability to modify functions in vivo.

Preferably, only the most strongly binding and effective peptide analogs or small molecules are used in the second or subsequent screening step. This two- or multi-step protocol reduces the number of false positives and identification of compounds which bind only weakly by eliminating the lower affinity small molecules that would be detected and then further studied if a conventional high throughput screening method were used. This method, therefore, is simple to implement, inexpensive, composed of only a few components, amenable to many different classes of receptors, and capable of rapidly screening large libraries of compounds. This method enables efficient identification of new classes of small organic peptidomimetic molecules that function as inhibitors or enhancers of receptor action, for example, thrombin receptor modifiers, dopamine receptor modifiers, histamine receptor modifiers, or vasopressin receptor modifiers. These identified compounds can target a single GPCR, a class of GPCR, or block or enhance a single G protein pathway activated by GPCR.

Thorough evaluation of the selected compounds (either peptides or small molecules) for use as therapeutic agents may proceed according to any known method. Properties of the compounds, such as $pK_a$, log P, size, hydrogen bonding and polarity are useful information. They may be readily measured or calculated, for example from 2D connection tables, if not already known prior to identification by the inventive method as a useful compound. Association/dissociation rate constants may be determined by appropriate binding experiments. Parameters such as absorption and toxicity also may be measured, as well as in vivo confirmation of biological activity. The screen may be optimized for small molecules according to methods known in the art. Additionally, it is preferable to use a software system for presentation of data that allows fast analysis of positives. See Example 36 and FIG. 2.

Pharmaceutical preparations are prepared by formulating the peptides or small molecules identified by the inventive screen according to methods well known in the art, with any suitable pharmaceutical excipient or combination of pharmaceutical excipients. Preparations may be made for administration by any route, such as intravenous, intramuscular, subcutaneous, oral, rectal, vaginal, transdermal, transmucosal, sublingual and the like, however, parenteral routes generally are preferred for peptide preparations. Any suitable vehicle may be used, for example saline or lactated Ringer's, for intravenous administration.

Dosages for treatment of GPCR-related diseases or conditions will depend on many factors such as the nature of the disorder, the GPCR involved, the route of administration, factors relating to the general physical condition and health of the patient and the judgment of the treating physician. Persons of skill in the art are well aware of these factors and consider manipulation of dosage to obtain an optimum result to be routine. Generally, dosages for intravenous administration may vary between about 0.01 mg/kg and 1000 mg/kg, however, this range can be expanded depending on the patient's needs. Such an expanded range is considered within the scope of this invention.

Alternatively, peptides according to this invention may be provided to cells, in vivo or ex vivo, by delivery of an expression construct. Gene therapy can be performed in vivo as a direct introduction of the genetic material. The in vivo gene transfer would introduce the oligonucleotides encoding the peptides to cells at the site they are found in the body, for example to skin cells on an arm, or to lung epithelial cells following inhalation of the gene transfer vector. Alternatively, ex vivo gene transfer, the transfer of genes into viable cells that have been temporarily removed from the patient and are then returned following treatment (e.g. bone marrow cells) could also be employed.

Gene transfer vectors can be engineered to enter specific tissues or cells. Transductional targeting allows the gene transfer vectors to interact with specific cell surface receptors. Transductional targeting also can take advantage of the rate of cellular division by using gene transfer vectors that target rapidly dividing cells such as tumor cells. Transcriptional targeting recruits distinct cellular promoter and enhancer elements to influence transcription of the therapeutic gene. Transfection efficiencies are also enhanced by engineering vectors with monoclonal antibodies, carbohydrate ligands, and protein ligands that help deliver genes to specific cells.

The gene transfer vectors used to produce the high affinity peptides inside cells could be viral vectors (e.g. Retrovirus, Adenovirus, Adeno-Associated Virus, Herpes Simplex Virus, or Vaccinia Virus). As an alternative, non-viral vectors also may be used, these include such methods as injection of naked DNA, or introduction of either DNA or peptides by attachment to positively charged lipids, or cationic liposomes, electroporation or ballistic DNA injection (limited to ex-vivo applications), as well as introduction of branched peptides.

Tet-inducible retroviral vectors for the native C-terminal sequences that co-expresses GFP driven by an internal ribosomal entry site (IRES) from encephalomyocarditis virus (p-Tet-Ti-GFP) may be used. These vectors can be modified so that they encode the high affinity peptide sequences. In addition, the high affinity peptide can be driven by a sequence allowing for spatial or temporal expression. For in vitro studies, viral supernatants may be collected from a pantropic producer line such as GP-293 (Clontech) in serum-free media. Viral supernatants may be concentrated by ultracentrifugation at 4° C. for 2 hr at 22,000 rpm, and the pellets resuspended in $\frac{1}{100}$ the original volume in serum-free media with a titer of at least $10^8$ IU(infectious units)/ml and stored at −80° C.

Murine leukemia virus (MLV) derived retroviral vectors are commonly used vehicles for stable delivery of therapeutic genes into endothelial cells. For the retrovirus studies in vivo, high affinity peptides advantageously are subcloned into a replication-defective murine Moloney retrovirus vector which is Tet-inducible and co-expresses GFP driven by an internal ribosomal entry site (IRES) from encephalomyocarditis virus (pTet-GFP). These constructs may then be transiently transfected into a producer line to generate cell-free titers of $10^6$-$10^{10}$ IU/ml. If needed, a pantropic retroviral expression system which utilizes VSV-G, an envelope glycoprotein from the vesicular stomatitis virus (GP-293; Clontech), may be utilized to overcome low transfection efficiencies. By using this innovative cell-based gene transfer method one can obtain stable, long-term, and localized gene expression of the high affinity C-terminal peptides.

To conclusively demonstrate that the compounds identified by this method can modulate G protein signaling events implicated in disease syndromes in vivo, antagonism or enhancement of selective G protein signal transduction events may be confirmed. One method of testing the ability of compounds to compete with native G protein binding involves expressing peptides that block the receptor-G protein interface in cells bearing the receptor. Plasmid constructs that encode GPCR-binding region peptides, such as carboxyl terminal peptide sequences from the various Gα subunits (see Table VI) can be used to express them in cells in vivo, ex vivo or in vitro, so that the metabolic effects of selective GPCR blockade can be studied qualitatively and quantitatively. Such studies provide proof that the binding which the compounds possess is useful in vivo to modulate selective G protein signals.

Expression of the peptides is conveniently achieved using the minigene approach by methods such as those described in Examples 23 and 24, however any suitable method may be used. Minigene vectors allow the high affinity peptides to be evaluated in cellular systems prior to high throughput screening. Any desired peptide sequence may be expressed using these methods. Those of skill in the art are well aware of alternative methods for construction, transfection and expression of protein and peptide constructs comprising the high affinity peptide analogs, and such methods are contemplated for use with them.

Human embryonic kidney cells advantageously are cultured in DMEM (Gibco) with 10% fetal bovine serum (Gibco), and Pen/Strep (5000 U/ml; 5000 μg/ml/Gibco) in an atmosphere of 95% air/5% $CO_2$ at 37° C. The cells may be plated at 60-70% density the day before transfection and transiently transfected for 1.5 hours with DNA (3 μg) for pcDNA 3.1 vector with the insert (pcDNA3.1-high affinity peptide) or vector alone using an Effectene kit from Qiagen. After transfection, cells are washed once before adding complete HMEC media. When required, selection for cells carrying the minigenes may be performed by adding Neomycin to the media 48 hrs after transfection. To monitor efficiency of transfection cells are transfected with the GFP plasmid (Clonetech). When necessary, transfectants may be selected using 300 μg/mL geneticin (G418). The expression of the vectors in HEK transfectants can be confirmed using reverse transcription (RT) PCR and Northern blot analysis for mRNA expression, and expression of the peptides can be characterized by HPLC as described previously. See Gilchrist et al., *Methods Enzymol.* 344:58-69, 2002, the disclosures of which are hereby incorporated by reference.

TABLE VI

Exemplary Sequences of C-terminal Minigene Peptides.

| Peptide Name | Sequence | SEQ ID NO: |
|---|---|---|
| Gαi | MGIKNNLKDCGLF | 112 |
| GαiR | MGNGIKCLFNDKL | 113 |
| Gαq | MGLQLNLKEYNAV | 114 |
| Gαq** | MGLQLNLKEYNTL | 115 |
| Gα12 | MGLQENLKDIMLQ | 116 |
| Gα13 | MGLHDNLKQLMLQ | 117 |

As discussed above, many receptors interact with and activate multiple G proteins. Using the minigene strategy to introduce the high affinity-binding carboxyl terminal peptides into cells, it is possible to inhibit specific G protein-coupled receptor interactions with individual G proteins, thus demonstrating the feasibility of specific G protein blockade in vivo with compounds identified by the inventive method. For those receptors which activate multiple G proteins each of which activates a distinct set of signaling pathways mediating a specific set of responses (for example, the thrombin receptor), one pathway can be inhibited without substantially affecting the others.

To selectively antagonize G protein signal transduction events in vivo by expressing peptides that block the receptor-G protein interface, minigene plasmid vectors were designed to express the C-terminal peptide sequence of the various Gα subunits following their transfection into mammalian cells. A control minigene vector also was created, encoding the carboxyl terminus of $Gαi_{1/2}$ in random order (GαiR, see Table VI). One important element necessary for the minigene approach to block intracellular signaling pathways effectively in vivo is expression of adequate amounts of the desired peptides. Therefore, expression of the minigene should be confirmed by a convenient method of detecting mRNA, protein or both. Any convenient method known in the art can be used.

To determine the cellular efficacy of the minigene approach for expressing GPCR binding peptides, and to show the specific inhibition of one G protein pathway in response to a given receptor activation signal without affecting others, compounds advantageously may be assayed in a system designed to exhibit a measurable cellular signaling endpoint. One example of such a system is the thrombin receptor, PAR1, in endothelial cells. This receptor activates multiple G proteins. Several signaling endpoints, including transcription analysis of induced PAR1 gene expression; biochemical analysis of effector molecules including [$Ca^{2+}$], MAP kinase ("MAPK") activity, adenylyl cyclase activity, and inositol phosphate accumulation; as well as functional assays such as cell proliferation and endothelial permeability are available to measure specific activation or modulation of activation of different G proteins by ligand binding at this receptor. Signaling activity may be measured by any convenient method, including: measuring inositol phosphate accumulation; measuring intracellular calcium concentration levels; measuring transendothelial electrical resistance; measuring stress fiber formation; measuring ligand binding (agonist, antagonist, inverse agonist, etc.); measuring receptor expression; measuring receptor desensitization; measuring kinase activity; measuring phosphatase activity; measuring nuclear transcription factors; measuring cell migration (chemotaxis); measuring superoxide formation; measuring nitric oxide formation; measuring cell degranulation; measuring GIRK activity; measuring actin polymerization; measuring vasoconstriction; measuring cell permeability; measuring apoptosis; measuring cell differentiation; measuring membrane association of a protein that translocates upon GPCR activation, such as protein kinase C; measuring cytosolic accumulation of a protein that translocates upon GPCR activation, such as protein kinase C; measuring cytosolic accumulation of a protein that translocates upon GPCR activation, such as src; and measuring nuclear association of a protein that translocates upon GPCR activation, such as Ran. The functional effects of Gα C-terminal minigenes in the mechanism of thrombin-induced cell retraction, as measured by the change in transendothelial electrical resistance (TEER) also can be used to measure G protein inhibition.

For example, thrombin-mediated PAR1 gene induction was inhibited in human microvascular endothelial cells (HMEC) expressing the Gαi minigene construct. Expression of the Gαq minigene construct, however, affected thrombin-mediated inositol phosphate accumulation. Expression of Gαq also specifically decreased both thrombin-induced intracellular [Ca$^{++}$]$_i$ rise and thrombin-induced MAPK activity.

Thrombin activation of the Gαi mechanism in HMEC decreases cAMP levels increased in response to isoproterenol (which acts through Gαs). Assay for cAMP level increases in response to isoproterenol alone may be compared to increases after thrombin pre-incubation in cells expressing Gαi to show that expression of the GPCR binding peptide blocks Gαi signaling.

Recent work by Gohla et al., *J. Biol. Chem.* 274:17901-17907, 1999, elegantly demonstrated that thrombin receptors induce stress fiber accumulation via Gα12 in an EGF receptor-independent manner. Stress fiber formation appears to be Rho dependent. Both G12 and G13 have been implicated in the Rho signaling pathway. Therefore, expression of Gα12 and Gα13 GPCR-binding peptides in HMEC were used to determine whether these peptides could block the appearance of stress fibers in response to thrombin.

The extracellular signal-regulated kinase (ERK) subfamily of mitogen-activated protein kinases (MAPKs) regulates numerous cell signaling events involved in proliferation and differentiation. This forms the basis of another assay which can determine whether GPCR binding peptides can affect a specific G protein mediated pathway. Transfection of HMEC cells with minigenes encoding GPCR binding peptides along with HA-MAPK followed by immunoprecipitation of the HA-MAPK permits measurement of the effects only on cells expressing GPCR binding peptides.

Many studies have shown that the M$_2$ muscarinic receptor (mAChR) couples exclusively to the Gi/GO family. See Dell'Acqua et al., *J. Biol. Chem.* 268:5676-5685, 1993; Lai et al., *J. Pharm. Exp. Ther.* 258:938-944, 1991; Offermanns et al., *Mol. Pharm.* 45:890-898, 1994; Thomas et al., *J. Pharm. Exp. Ther.* 271:1042-1050, 1994. The M$_2$ mAChR can efficiently couple to mutant Gαq** in which the last five amino acids are substituted with the corresponding residues from Gαi or GαO, suggesting that this receptor contains domains that are specifically recognized by the carboxyl terminus of Gαi/O subunits. See Liu et al., *Proc. Natl. Acad. Sci. USA* 92:11642-11646, 1995.

To test inhibition of G protein-coupled receptor-mediated cellular responses by carboxyl terminal Gα peptides expressed using minigene constructs, prototypical directly Gβγ activated channels (GIRK channels) regulated by a pertussis toxin-sensitive M$_2$ mAChR was chosen as the model. In this model, the importance of the Gα carboxyl terminus and the downstream effector system have been well established. See Krapivinsky et al., *J. Biol. Chem.* 270:29059-29062, 1995; Krapivinsky et al., *J. Biol. Chem.* 273:16946-16952, 1998; Sowell et al., *Proc. Natl. Acad. Sci. USA* 94:7921-7926, 1997. Inhibition of M$_2$ mAChR activation of inwardly rectifying potassium currents can be tested to demonstrate inhibition of a downstream functional response following agonist stimulation of GPCR on cells transiently transfected with a Gα carboxyl terminal peptide minigene or treated with a pharmaceutical compound identified by screening against high affinity Gα peptides.

GIRK channels modulate electrical activity in many excitable cells. See Breitwiese et al., *J. Membr. Biol.* 152:1-11, 1996; Jan et al., *Curr. Opin. Cell Biol.* 9:155-160, 1997; Wickman et al., *Curr. Opin. Neurobiol.* 5:278-285, 1995. Because the channel opens as a consequence of a direct interaction with Gβγ, whole cell patch clamp recording of T$_{KACh}$ can be used to demonstrate inhibition of a downstream functional response following agonist stimulation of GPCR on cells transiently transfected with a Gα carboxyl terminal peptide minigene or treated with a pharmaceutical compound identified by screening against high affinity Gα peptides. Superfusion of cells expressing GIRK1/GIRK4 with their ligand, acetylcholine (ACh), activates inwardly rectifying potassium currents.

Using well-established receptor models accepted to be indicative of in vivo cellular results, this type of data can show that the individual G proteins activated via a given GPCR have specific roles in mediating cellular events and can be modulated in a specific fashion by ligands mimicking GPCR binding regions of individual Gα subunits. In particular, for receptors such as the thrombin receptor, which activate multiple G proteins, each of which activates a distinct set of signaling pathways mediating a specific set of responses, it is possible using the inventive methods to block one pathway while leaving all the others functional. The high affinity peptide analogs identified in vitro by consecutive affinity purification and competitive binding are capable of specifically inhibiting the downstream consequences of G protein signaling.

The assays described above clearly establish the ability of compounds identified by in vitro competitive binding studies to modulate a particular GPCR-G protein interaction selectively, even when the GPCR regulates multiple G proteins within the cell. Moreover, the peptides compete very effectively with the native sequence. In addition, the minigene approach described above and exemplified in the examples below allows a systematic test of the roles of other G proteins such as Gα12 and Gα13, which may be involved in the mechanism of increase of endothelial permeability, and clearly demonstrates the viability of this approach to select and identify Gα subunit modulating compounds. The peptides therefore are suitable for use in treatment of any disorder or syndrome characterized by G protein signaling excess.

In another aspect, the invention relates to methods to identify the G proteins with which a specific orphan receptor is coupled, using the materials provided by the invention. For example, the described methods can be used to test any GPCR with a battery of Gα subunit peptides to determine which species of G protein(s) mediates the effects of the receptor. The methods described in Examples 12-14 are suitable. Those of skill in the art are capable of designing other assays, or variations and modifications using these assays as guides.

Rhodopsin can be measured spectrophotometrically in many of its conformational states. The high affinity, biologically active rhodopsin state can be easily differentiated from its precursor, MI, by the "extra" MII assay. See Example 35. This assay relies on the observation that under conditions of high pH and low temperature, MII is stabilized in the presence of Gt and can be spectrophotometrically measured. The ability of the C-terminal peptide to stabilize Meta II in the same manner as the heterotrimeric Gt, provides the tools to investigate the structural basis of the interaction of G proteins with the agonist binding sites of activated receptors.

The screening platform according to one embodiment of the invention can identify small molecules that increase the binding of the high affinity peptides which mimic G protein or stabilize the active conformation of the GPCR. These small molecules have an appropriate dose curve, and have an $EC_{50}$ in the low μM range. Samples of urea-washed rod outer segments typically have little or no (<5%) stabilization of MII unless G protein is added, however, the small molecules identified by the invention in one example screen stabilize the active (signaling) conformation of rhodopsin (MII). Addition of the small molecule alone results in 70% stabilization. The $EC_{50}$ for stabilization of MII also appears to be in the low μM range. Further, these same small molecules were added to human embryonic kidney (HEK) cells with measurement of their calcium response to a second GPCR do not enhance signaling of an unrelated GPCR and do not appear to cause an acute toxic response.

Drug discovery has evolved from an essentially random screening of products, into a process that includes the rational and combinatorial design of large numbers of synthetic molecules as potential bioactive agents, such as agonists, antagonists and inverse agonists, as well as the structural characterization of their biological targets, which may be polypeptides, proteins, or nucleic acids. Several approaches to facilitating the understanding of the structure of the therapeutic targets have been developed. These include sequencing of proteins and nucleic acids (Findlay et al., *Protein Sequencing: A Practical Approach*, IRL Press, Oxford, 1989; Adams et al., *In Automated DNA sequencing and Analysis*, Academic Press, San Diego, 1994), elucidation of secondary and tertiary structures via NMR (Jefson, *Ann. Rep. Med. Chem.* 23:275, 1998; Erikson and Fesik, *Ann. Rep. Med. Chem.* 27:271-289, 1992), X-ray crystallography (Erikson and Fesik, *Ann. Rep. Med. Chem.* 27:271-289, 1992) and computer algorithms for predicting protein folding (Copeland, *Methods of Protein Analysis: A Practical Guide to Laboratory Protocols*, Chapman and Hall, New York, 1994; Creighton, *Protein Folding*, W.H. Freeman and Co., 1992). Experiments such as ELISA (Kemeny and Challacombe, *ELISA and other Solid Phase Immunoassays: Theoretical and Practical Aspects*; Wiley, N.Y., 1988) and radioligand binding assays (Berson and Yalow, *Clin. Chim. Acta*, 22:51-60, 1968; Chard, *An Introduction to Radioimmunoassay and Related Techniques*, Elseveier press, Amsterdam/New York, 1982), surface-plasmon resonance (Karlsson et al., *Anal. Biochem.* 300:132-138, 2002), and scintillation proximity assays (Kariv et al., *J. Biomol. Screen.* 4:27-32, 1999) also can be used to understand the nature of the receptor-G protein interaction.

Peptides that block the protein-protein interactions of interest do so by binding to the surface of one of the interacting proteins and mimicking the interactions of the complete protein with the receptor. One can study the conformation of the active receptor-bound peptides when they are exchanging with the bound form, using transferred-NOESY NMR methods or X-ray diffraction if the peptides are more tightly bound. The bound peptide conformations can provide useful templates for the design of non-peptide small molecule drug leads which block the protein-protein interactions of interest. The binding sites of the peptides on the receptors also can be investigated using photochemical crosslinking, by substitution of peptide residues with photoactivatable amino acid analogs, crosslinking of the peptide to the receptor binding sites, cleavage of the receptor into peptide fragments and mass spectrometry analysis of the location of the binding sites. Combining structural data from a variety of experiments allows the development of models of the interacting protein surfaces using computer graphics and guides the design of novel non-peptide molecules to modulate the interactions.

In X-ray diffraction crystallography, a crystalline form of the molecule under study is exposed to a beam of X-rays and the intensity of defracted radiation is measured at a variety of angles from the angle of incidence. The beam of X-rays is diffracted into a plurality of diffraction "reflections," with each reflection representing a reciprocal lattice vector. From the diffraction intensities of the reflections, the magnitudes of a series of numbers, known as "structure factors," are determined. The structure factors in general are complex numbers, having a magnitude and a phase in the complex plane, and are defined by the electron distribution within the unit cell of the crystal.

Crystals can be formed of receptor or portions of receptor bound to peptides that stabilize a particular conformation of interest. The methods of this invention, which identify peptides using combinatorial techniques that scan the complete set of possible amino acid sequences to find those that bind specifically to a particular receptor with high affinity, can identify peptides that bind to particular conformations of a GPCR. These peptides can be bound (and co-crystallized) with the receptor for structural determination studies by NMR or crystallography. Co-crystallization in this manner may be performed according to any method known in the art, for example the methods of Kimple et al., *Nature* 416:878-881, 2002, the disclosures of which are hereby incorporated by reference.

Therefore, in another embodiment, assays for identifying peptides that bind to a particular conformer of a GPCR are performed according to the methods described above for selection of the high affinity peptide analogs that bind activated rhodopsin. Once the high affinity peptides have been identified, they can be used in peptidomimetic studies. Compounds that mimic the conformation and desirable features of a particular peptide, e.g., an oligopeptide, but that avoid undesirable features, e.g., flexibility (loss of conformation) and metabolic degradation, are known as "peptidomimetics." Peptidomimetics that have physical conformations that mimic the three dimensional structure of the high affinity peptide analogs, that have surface active groups that allow binding to the receptor, or that have physical conformations that mimic the three dimensional structure of the high affinity peptide analogs can be used to make pharmaceutical compositions. Drugs with the ability to mimic the function of the high affinity peptide analogs that bind to the designated receptors can be identified using rational drug design according to this invention. The compounds preferably include the surface active functional groups of the high affinity peptide analogs, or substantially similar groups, in the same or substantially similar orientation, so that the compounds possess the same or similar biological activity. The surface-active functional groups in the high affinity peptide analogs possess a certain orientation when the receptor is present, in part due to their secondary or tertiary structure. Rational drug design involves both the identification and chemical modification of suitable compounds that mimic the function of the parent molecules.

The physical conformation of the peptidomimetics are determined, in part, by their primary, secondary and tertiary structure. The primary structure of a peptide is defined by the number and precise sequence of amino acids in the high affinity peptide analogs. The secondary structure is defined by the extent to which the polypeptide chains possess any helical or other stable structure. The tertiary structure is defined by the tendency for the polypeptides to undergo extensive coiling or folding to produce a complex, somewhat rigid three-dimensional structure.

Computer modeling technology allows scientists to visualize the three-dimensional atomic structure of a selected molecule and derive information that allows the rational design of new compounds that will mimic the molecule or which will interact with the molecule. The three-dimensional structure can be determined based on data from X-ray crystallographic analyses and/or NMR imaging of the selected molecule, or from ab initio techniques based solely or in part on the primary structure, as described, for example, in U.S. Pat. No. 5,612,895. The computer graphics systems enable one to predict how a new compound will link to the target molecule and allow experimental manipulation of the structures of the compound and target molecule to perfect binding specificity.

Many databases and computer software programs are available for use in drug design. For example, see Ghoshal et al., *Pol. J. Pharmacol.* 48(4):359-377, 1996; Wendoloski et al., *Pharmacol. Ther.* 60(2):169-183, 1993; and Huang et al., *J. Comput. Aided Mol. Des.* 11:21-78, 1997. Databases including constrained, metabolically stable non-peptide moeties may be used to search for and to suggest suitable analogs of the high affinity peptides identified in the screen. Searches can be performed using a three dimensional database for non-peptide (organic) structures (e.g., non-peptide analogs, and/or dipeptide analogs) having three dimensional similarity to the known structure of the active regions of these molecules. See, for example, Allen, *Acta Crystallogr. B.* 58:380-388, 2002.

Alternatively, three dimensional structures generated by other means such as molecular mechanics can be consulted. In addition, search algorithms for three dimensional database comparisons are available in the literature. Rufino et al., *J. Comput. Aided Mol. Des.* 8:5-27, 1994. Commercial software for such searches is also available from vendors such as Accelrys Inc. (9685 Scranton Road, San Diego, Calif. 92121-3752). The searching is done in a systematic fashion by simulating or synthesizing analogs having a substitute moiety at every residue level. Preferably, care is taken that replacement of portions of the backbone does not disturb the tertiary structure and that the side chain substitutions are compatible to retain the high affinity peptide/receptor interactions.

Using information regarding the bond angles and spatial geometry of the critical amino acids, one can use computer programs as described herein to develop peptidomimetics. Thermal protein unfolding, or thermal "shift" assays have been used to determine whether a given ligand binds to a target receptor protein. In a physical thermal shift assay, a change in a biophysical parameter of a protein is monitored as a function of increasing temperature. For example, in calorimetric studies, the physical parameter measured is the change in heat capacity as a protein undergoes temperature-induced unfolding transitions. Differential scanning calorimetry may be used to measure the affinity of a ligand for a G protein coupled receptor. Grauschopf et al., *Biochemistry* 39:8878:87, 2000; Brandts et al., *Biochemistry* 29:6927-40, 1990. Thus, using methods common to those skilled in the arts, the high affinity peptides may be assayed for their ability to modulate thermal shift of the receptor.

Because of the difficulty in obtaining high-resolution crystallographic structures from GPCRs, a variety of biophysical methods have been applied to characterize the interactions between the G protein, the receptor and the ligand. These include fluorescence resonance energy transfer (FRET) experiments performed with fluorescence-labeled peptide analogs (Bettio et al., *Biopolymers* 60:420-37, 2001), bioluminescence resonance energy transfer (BRET) experiments (Ayoub et al., *J. Biol. Chem.* 277:21522-8, 2002), photoaffinity labeling (Turek et al., *J. Biol. Chem* 277:16791-16797, 2002), fluorescence spectroscopy (Ghanouni et al. *J. Biol. Chem.* 276:24433-24436, 2001), site-direct spin labeling (Hubbell et al., *Nat. Struct. Biol.* 7:735-739, 2000), Fourier transform infrared difference spectroscopy (Vogel et al., *Biochemistry* 35:11149-11159, 1996), and intrinsic tryptophan fluorescence spectroscopy. Farrens et al., *J. Biol. Chem.* 270:5073-5076, 1995.

The following non-limiting examples are provided to illustrate certain aspects of this invention.

EXAMPLES

Example 1

Construction of a Peptide Library

Figure 3:
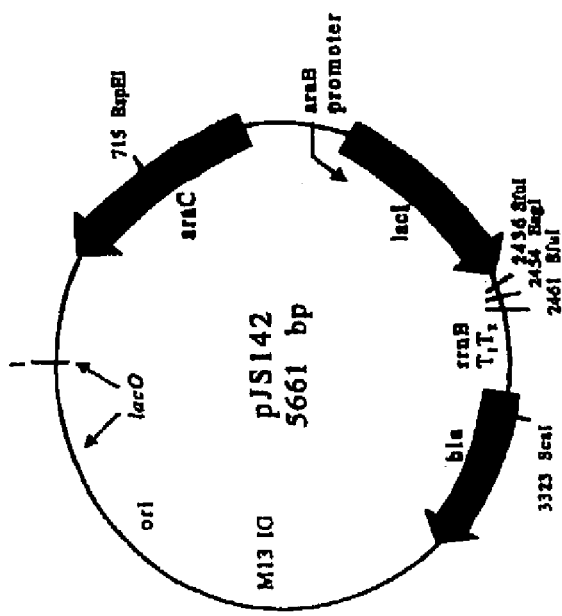
FIG. 3 is a schematic diagram of vector pJS142.

Construction of a biased peptide library has been described previously. Martin et al., *J. Biol. Chem.* 271:361-366, 1996; Schatz et al., *Meth. Enzymol.* 267:171-191, 1996. The vector used for library construction was pJS142 (see FIG. 3). This vector had a linker sequence between the LacI and the biased undecamer peptide coding sequence, as well as restriction sites for cloning the library oligonucleotide. The oligonucleotide synthesized to encode the mutagenesis library was synthesized with 70% of the correct base and 10% of each of the other bases at each position. This mutagenesis rate leads to a biased library such that there is approximately a 50% chance that any of the 11 codons will be the appropriate (native) amino acid and approximately a 50% chance that it will be another amino acid. In addition, a linker of four random NNK (where N denotes A, C, G or T and K denotes G or T) codons were synthesized at the 5' end of the sequence to make a total of 15 randomized codons. Using this method, a library with greater than $10^9$ independent clones per microgram of vector used in the ligation was constructed based on the carboxyl terminal sequence of Gαt (IKENLKDCGLF; SEQ ID NO:15). The nucleic acid used for creating this library was:

```
5'-GAGGTGGTNNKNNKNNKNNKattcaaggagaacctgaaggactgcgg
cctcttcTAACTAAGTAAAGC-3',
wherein N = A/C/G/T and K = G/T; SEQ ID NO:118).
```

Example 2

Sequences for the Creation of Gα Subunit Peptide Libraries

Libraries were created using the methods of Example 1 and the sequences listed below in Table VII.

PBS with 5 mM EDTA and washed twice in PBS. The pellet was either used immediately for membrane preparation or stored frozen at −20° C. Pellets were homogenized in 20 mM Tris-HCl, pH 7.5, with 5 mM EDTA and 0.5 mM PMSF, using a Dounce homogenizer (10 strokes) and sonicated for 10 seconds. Nuclear debris and intact cells were removed by centrifugation at 3000 rpm for 10 minutes. The supernatant was sedimented at 12,000×g for 30 minutes and the resulting pellet suspended in 25 mM Tris-HCl, pH 7.5, 25 mM $MgCl_2$, 10% sucrose, 0.5 mM PMSF, 50 μg/mL antipain, 1 μg/mL aprotinin, 40 μg/mL bestatin, 100 μg/mL chymostatin, 0.5 μg/mL leupeptin and 0.7 μg/mL pepstatin. The membranes were aliquoted and frozen at −80° C.

TABLE VII

C-Terminal Gα Subunit Peptide Library Constructs.

| Gα Subunit | RE | Linker | Peptide Coding Region | Stop | RE | SEQ ID NO: |
|---|---|---|---|---|---|---|
| Gs | 5-GAGGTGGT | NNKNNKNNKNNK | attcgtgaaaacttaaaagattgtggtcgtttc | TAA | CTAAGTAAAGC-3' | 14 |
| G11 | 5-GAGGTGGT | NNKNNKNNKNNK | ctgcagctgaacctgaaggagtacaatctggtc | TAA | CTAAGTAAAGC-3' | 119 |
| G12 | 5-GAGGTGGT | NNKNNKNNKNNK | ctgcaggagaacctgaaggacatcatgctgcag | TAA | CTAAGTAAAGC-3' | 120 |
| G13 | 5-GAGGTGGT | NNKNNKNNKNNK | ctgcatgacaacctcaagcagcttatgctacag | TAA | CTAAGTAAAGC-3' | 121 |
| G15 | 5-GAGGTGGT | NNKNNKNNKNNK | ctcgcccggtacctggacgagattaatctgctg | TAA | CTAAGTAAAGC-3' | 122 |
| Gz | 5-GAGGTGGT | NNKNNKNNKNNK | atacagaacaatctcaagtacattggcctttgc | TAA | CTAAGTAAAGC-3' | 123 |

Example 3

Isolation of Membranes from Insect Cells Expressing Thrombin Receptor

Sf9 cells (2×10⁸ cells) were cultured with 200 ml of Grace's insect cell culture medium (Life Technologies, Inc., Grand Island, N.Y.) containing 0.1% Pluronic F-68 (Life Technologies, Inc., Grand Island, N.Y.)), 10% fetal calf serum, and 20 μg/ml gentamicin in a 1-liter spinner flask at 27° C. for 25 hours. Sf9 cells were infected with the ThR/pBluebac recombinant virus at a multiplicity of infection of 3-5, and cultured at 27° C. for 4 days. The cells were harvested, washed with phosphate buffered saline, and then resuspended in 10 mM Tris-HCl, pH 7.4. Cells were then homogenized with a hand-held homogenizer set at low speed for 20 seconds. The broken cells then were sedimented at 17,000×g for 15 minutes. The supernatant was discarded, and the pellet resuspended in a buffer consisting of 50 mM Tris-HCl, pH 7.4 and 10% glycerol. Concentration of receptor in the membrane preparation ranged from 1-10,000 pmole/mg. For screening, a final concentration of 200 μg/ml was used. The thrombin receptors were tested for their ability to bind to the native Gq-C terminal peptide using a MBP-GQ fusion protein.

Example 4

Isolation of Membranes from Mammalian Cells Overexpressing Thrombin Receptor PAR1 receptor cDNA (2.1 kb insert) was obtained by polymerase chain reaction and cloned into the mammalian expression vector pBJ5. The resulting plasmid was transfected into Chinese hamster ovary cells by the calcium phosphate coprecipitation method. The PAR1-transfected cells were grown with Dulbecco's modified Eagle's medium containing 10% fetal calf serum, 100 units/mL penicillin and 100 μg/mL streptomycin. The cells were detached using

Example 5

Preparation of Rod Outer Segments

Bovine rod outer segments (rhodopsin-containing membranes) were prepared from fresh retinas under dim red light as described by Arsharky et al., *J. Biol. Chem.* 269:19882-19887, 1994. The retinas were placed in a beaker for dissection filled with 200 mL of 30% (w/v) sucrose in isolation buffer (90 mM KCl, 30 mM NaCl, 2 mM $MgCl_2$, 0.1 mM EDTA, 1 mM DTT, 50 μM phenylmethylsulfonyl fluoride, 10 mM MOPS, pH 7.5) on ice with constant moderate stirring of the solution during dissection. Following dissection, the retina solution was left in the dark for one hour on ice. The retina-sucrose solution was distributed into eight 50 mL tubes and sedimented at 3000×g for four minutes at 4° C. The supernatant was decanted into eight fresh centrifuge tubes and placed on ice. The tubes were filled to 1.5 cm below top with isolation buffer, then sedimented at 17,000×g for 20 minutes ("spin 1").

The pellets were resuspended in a small volume of 30% sucrose and consolidated from eight tubes into four tubes. The tubes were filled to 1.5 cm below top with 30% sucrose, sedimented at 5000×g for four minutes at 4° C., and the supernatant decanted into four clear tubes. These tubes were filled to 1.5 cm below top with isolation buffer and sedimented at 17,000×g for 20 minutes at 4° C. ("spin 2").

A stepwise sucrose gradient was prepared in six gradient tubes using the solutions in Table VIII, below, with a sequence from top to bottom of #2, #3, #4.

TABLE VIII

Sucrose Gradient Solutions.

| Solution | #2 (0.84 M) | #3 (1.0 M) | #4 (1.14 M) |
|---|---|---|---|
| 42% Sucrose | 51.30 g | 61.05 g | 69.75 g |
| 1.0 M MOPS | 750 μL | 750 μL | 750 μL |

TABLE VIII-continued

| | Sucrose Gradient Solutions. | | |
|---|---|---|---|
| Solution | #2 (0.84 M) | #3 (1.0 M) | #4 (1.14 M) |
| 2.0 M KCl | 2250 μL | 2250 μL | 2250 μL |
| 3.0 M NaCl | 750 μL | 750 μL | 750 μL |
| 2.0 M MgCl$_2$ | 75 μL | 75 μL | 75 μL |
| Total Weight | 83.25 g | 84.75 g | 86.25 g |

The pellets from "spin 1" and "spin 2" were resuspended in isolation buffer using 1 mL 26% sucrose buffer per tube. After making a slurry, each tube was homogenized with a 1 mL pipette and the tubes consolidated. The pellet solution was carefully laid onto the sucrose gradients and was not allowed to invade the gradient layers. The gradient tubes were subjected to 24,000×g for 30 minutes at 4° C. in a swinging bucket rotor, after which the orange layer containing the membranes was collected carefully, to avoid disturbing the pellet or the dark solution near the pellet. The membranes were distributed into six 50 mL tubes and placed on ice. The tubes then were filled to 1.5 cm below top with isolation buffer and sedimented at 17,000×g for 20 minutes at 4° C. The supernatant was discarded and the pellets resuspended in 1 mL isolation buffer containing 5 μg/mL pepstatin and 10 μg/mL E-64. This suspension was stored in a foil-wrapped 15 mL conical tube at −80° C. until needed, then thawed, homogenized in EDTA buffer (10 mM Tris, pH 7.5, 1 mM EDTA 1 mM DTT) and sedimented at 30,000×g for 30 minutes. The supernatants were discarded and the pellets resuspended and sedimented again as described above. The pellets then were resuspended in urea buffer (10 mM Tris, pH 7.5, 1 mM EDTA, 1 mM DTT, 7 M urea), homogenized and sedimented at 45,000 kg for 40 minutes. These pellets were resuspended and homogenized in Buffer A (200 mM NaCl, 10 mM MOPS, pH 7.5, 2 mM MgCl$_2$, 1 mM DTT, 100 μM PMSF), then sedimented at 30,000×g for 30 minutes. The pellets each were resuspended and homogenized by pipetting in 1 mL buffer A and stored at −80° C. in 100 μL aliquots in foil-covered tubes for use in assays. For screening, the receptor was added to wells at 10 μg/ml. Binding assays were performed as in Example 18.

Example 6

Purification of PAR1 Thrombin Receptor from Insect Cells and Reconstitution of Receptors into Lipid Vesicles Sf9 cells (2×10$^8$ cells) were cultured in Grace's insect cell culture medium (Life Technologies, Inc., Grand Island, N.Y.) containing 0.1% Pluronic F-68 (Life Technologies), 10% fetal calf serum and 20 μg/mL gentamicin in a 1 L spinner flask at 27° C. for 25 hours. The cells were infected with ThR/pBluebac (recombinant virus) at a multiplicity of infection of 3-5 and cultured at 27° C. for four days. The cells were harvested, washed with phosphate buffered saline containing 2.7 mM EDTA and stored at −70° C. until used. The cells were resuspended in lysis buffer (2.5 mM Tris-HCl, pH 7.2, 7.5 mM NaCl, 10 mM EDTA, 1 mM phenylmethylsulfonyl fluoride, 10 mg/mL leupeptin, 10 mg/mL aprotinin, 50 mM NaF) and washed. All subsequent steps were done on ice with cold buffers and centrifuge rotors at or below 4° C. The cells were homogenized for one minute at maximum speed and sedimented for 45 minutes at 30,000×g. The pellet was resuspended in lysis buffer and the homogenation/washing step repeated three times. The resulting pellet was resuspended in 30 mL solubilization buffer (20 mM Tris-HCl, pH 7.4, 15 mM EGTA, 1 mM phenylmethylsulfonyl fluoride, 10 mg/mL leupeptin, 10 mg/mL aprotinin, 50 mM NaF, 0.1% (w/v) digitonin, 0.1% (w/v) Na deoxychoate) and then homogenized for one minute. The suspension was stirred for 90 minutes at 4° C. and then sedimented for 60 minutes at 30,000×g. The supernatant was loaded onto an anti-PAR1 monoclonal antibody column equilibrated with solubilization buffer containing 0.2% digitonin. After application of the supernatant, the column was washed with 10 column volumes of 10 mM Tris-HCl buffer, pH 7.4, containing 0.2% (w/v) Na dodecyl maltoside. The receptor was eluted using 10 mM triethylamine, pH 11.8. The eluted fractions were neutralized immediately using 1 M HEPES, pH 6.4. The pooled fractions were dialyzed against 50 mM HEPES buffer, pH 7.4, containing 50% (v/v) glycerol, 0.1 M NaCl and 0.2% (w/v) Na dodecyl maltoside. Aliquots were stored at −80° C.

For preparation of lipid vesicles, 200 μL phosphatidylserine (50 mg/mL in CHCl$_3$; Matreya) was dried in a rotary evaporator for 30 minutes or using a stream of dry N$_2$. After addition of 200 μL buffer A (50 mM HEPES, 100 mM NaCl, 0.2% (w/v) Na dodecylmaltoside), the tube was sealed under an N$_2$ atmosphere and sonicated in a bath sonicator for 30 minutes. Reconstitution of receptors into lipid vesicles was performed the same day, using purified receptor prepared as in Example 5. Purified receptor stocks (200 μg/mL) were thawed on ice and 50 μL was incubated for 20 minutes at 4° C. with the appropriate agonist peptide (100 nM final concentration). In the case of thrombin receptor, the agonist is thrombin receptor agonist peptide (CalbioChem). After addition of 80 μL sonicated lipids and 50 μL buffer A, the samples were mixed using a vortex machine and placed on ice for 10 minutes. The samples then were loaded onto a 1 mL Extracti-gel™ column which had been washed with 0.2% BSA and pre-equilibrated with 5 mL Buffer A without Na dodecylmaltoside. The reconstituted vesicles were eluted from the column with 2.5 mL HEK buffer.

Samples (100-200 μL) were collected for purity analysis by SDS-PAGE. The concentration for each batch generally was about 10-1000 μg/ml. For use, receptor was placed in microtiter plates at about 1-100 μg/ml. The purified, reconstituted thrombin receptors were tested for their ability to bind to the native Gq-C terminal peptide using a MBP-Gq fusion protein. As a control, empty vesicles also were tested for their ability to bind to the native Gq-C terminal peptide using a MBP-Gq fusion protein.

Example 7

Identification of GPCR-Binding High Affinity Peptide Analogs (Panning)

Electrocompetent cells were produced as follows. A single colony of ARI814 bacteria was grown overnight at 37° C. in 5 ml sterile SOP (20 g/L Bacto-tryptone; 10 g/L Bacto-yeast extract; 5 g/L NaCl; 2.5 g/L anhydrous K$_2$HPO$_4$; 1 g/L Mg$_2$SO$_4$.7H$_2$O). One milliliter of this overnight growth was added to 500 ml SOP and the bacteria were allowed to grow until the OD$_{600}$ read 0.6-0.8. All further washing steps were done in the cold. The cells were placed in an ice-water bath for at least 15 minutes, then subjected to centrifugation at 4000×g for 15 minutes at 4° C. followed by resuspension in 500 ml 10% glycerol. After sitting on ice for 30 minutes, the cells were washed twice more in 500 ml and 20 ml 10% glycerol with sedimentation as above, and finally sedimented at 5000×g for 10 minutes at 4° C. and resuspended in 1 mL 10% glycerol. Cells were quick-frozen using dry ice and isopropanol in 100 μL aliquots for later use.

To transfect, aliquots (40 μL) of thawed ARI814 cells were placed into each of three chilled microcentrifuge tubes. A peptide display library based on the undecamer carboxyl terminal peptide of Gαt (SEQ ID NO:15) was prepared according to Example 1. Two microliters of library plasmid were added to the tubes and mixed. For the first round of "panning," 200 μl of the plasmid library was added. For subsequent rounds, three sets of transfections were performed (adherent plasmids from wells containing receptor (+); adherent plasmids from wells containing no receptor (−); and the PRE sample which was not incubated). See below.

In each round of panning, less library was used (round 2:100 μl; round 3:50 μl; round 4:10 μl). After the panning was completed, the DNA for the LacI fusion protein was eluted. This DNA (50 μl) was used to transfect *E. Coli* cells by electroporation, using cold, sterile 0.1 cm electrode gap cuvettes. The cuvettes were pulsed one time using a BioRad *E. coli* Pulsar set to 1.8 kV, 25 μF capacity, time constant 4-5 mseconds, with the Pulser Controller unit at 200 mΩ. Immediately, 1 mL of SOC was added and the mixture transferred to a labeled 17×100 mm polystyrene tube. The tube was shaken for one hour at 37° C. Aliquots were taken from each set to plate 100 μL undiluted to $10^{-6}$ dilution samples on LB-Amp plates. Counts of the PRE plates indicated library diversity, while comparison of the (+) and (−) plates indicated whether specific clones were being enriched by the panning procedure.

The remaining ~900 μL in the + receptor tube was added to a 1 L flask containing 200 mL LB-AMP media, pre-warmed to 37° C., and grown at 37° C., shaking until $OD_{600}$=0.5. The tube of cells then were placed in an ice water bath for at least 10 minutes, and kept chilled at or below 4° C. during the subsequent washing steps. The cells were sedimented at 5000×g for six minutes, resuspended in 100 mL WTEK buffer, sedimented at 5000×g for six minutes, resuspended in 50 mL TEK buffer, resedimented at 5000×g for six minutes and resuspended in 4 mL HEK buffer. The cells were divided into the cryovials and stored at −70° C. One tube was used for the next round of panning and the other saved as a backup.

The panning process is illustrated in FIG. 1. For screening of the library by "panning," rhodopsin receptors prepared according to Example 5 were immobilized directly on Immulon 4 (Dynatech) microtiter wells (0.1-1 μg of protein per well) in cold 35 mM HEPES, pH 7.5, containing 0.1 mM EDTA, 50 mM KCl and 1 mM dithiothreitol (HEK/DTT). After shaking for one hour at 4° C., unbound membrane fragments were washed away with HEK/DTT. The wells were blocked with 100 μl 2% BSA in HEKL (35 mM HEPES; 0.1 mM EDTA; 50 mM KCl; 0.2 M α-lactose; pH 7.5, with 1 mM DTT). For rounds 1 and 2, BSA was used for blocking; in later rounds 1% nonfat dry milk was used. For the first round of panning, about 24 wells of a 96-well plate were used. In subsequent rounds, 8 wells with receptor and 8 wells without receptor were prepared.

The Gt library was thawed (2 mL aliquot) and mixed with 6 mL lysis buffer on ice. Lysis buffer contains 4.25 mL HE (25 mM HEPES; 0.1 mM EDTA; pH 7.5); 1 mL 50% glycerol; 750 μL 10 mg/mL protease-free BSA in HE; 10 μL 0.5 M DTT; and 6.25 μL 0.2 M PMSF. Freshly prepared lysozyme solution (150 μL 10 mg/mL lysozyme in cold HE) was added and the tube was gently inverted several times and incubated on ice for no more than two minutes. The extent of lysis is evidenced by an increase in viscosity that can be observed by noting the slow migration of bubbles to the top of the tube after mixing. Lysis was terminated by mixing in 2 mL 20% lactose and 250 μL 2M KCl. The tube was centrifuged immediately at 13,000×g for 15 minutes at 4° C. and the supernatant transferred to a new tube. A small aliquot of 0.1% (the PRE sample) was saved in a separate, labeled tube. The blocked rhodopsin receptor-coated plate was rinsed four times with HEKL/1% BSA and exposed to room light for less than five minutes on ice to activate the rhodopsin for light-activated rhodopsin (Table IX), or left in the dark for dark-adapted (inactive) rhodopsin (Table X). Immediately thereafter, the crude bacterial lysate from the peptide library (200 μL) was added to each well and allowed to shake gently for one hour at 4° C. For round 2, this same procedure was followed. In round 3, the amount of lysate used was reduced to 100 μL. In subsequent rounds, the lysate was diluted 1:10 in HEKL/BSA. In all rounds, 5-10 μL 200 μM native peptide was added to the wells to chase off peptides that were bound with lower affinity.

After incubation with the bacterial lysate, the wells were washed four times into cold HEKL/1% BSA. Sonicated salmon sperm DNA (200 μL 0.1 mg/mL in HEKL/1% BSA was added to each well and shaken gently for 30 minutes at 4° C. The plates were washed four times with cold HEKL and twice with cold HEK, then eluted by adding 50 μL/well 1 mM IPTG/0.2 M KCl in HE with vigorous shaking at room temperature for 30 minutes. The eluants from each group of wells (+ or − receptor) were combined in one or more microcentrifuge tubes as necessary. The volume of the PRE sample which had been saved previously was brought up to match the volume of the eluant samples and precipitated in parallel with them. To precipitate, 1/10 volume of 5M NaCl was mixed with each of the samples, then 1 μL 20 mg/mL glycogen was mixed with the samples. An equal volume of RT isopropanol was then added and mixed thoroughly. The samples were subjected to centrifugation at 13,000×g for 15 minutes and the supernatant aspirated. The pellet was washed with 500 μL cold 80% ethanol and again subjected to centrifugation at 13,000×g for 10 minutes. The pellets of plasmid DNA were resuspended in sterile, double-distilled water, 200 μL for the PRE sample and 4 μL for the + or − receptor samples and stored at −20° C.

Both light-activated rhodopsin and dark-adapted rhodopsin were used to screen the library in this manner. See Tables IX and X, below. Six of the sequences obtained using light-activated rhodopsin were 100-1000 times more potent than the native sequence at binding rhodopsin and are listed in Table IX. When the Gαt library was used to pan light-activated rhodopsin, residues L344, C347 and G348 were invariant. Also, in each of the highest affinity sequences, the basic residue at position 341 (R341) was changed to a neutral residue. When the Gαt library was used to pan dark-adapted rhodopsin, the L344, C347 and G348 residues were no longer invariant (L344 present in 62.5% of sequences, C347 present in 25% of sequences, G348 present in 75% of sequences) and the residue at position 341 was usually unchanged. Thus, the conformation of the receptor in its inactive, dark-adapted state allows it to bind to a different set of peptide analogs than the light-activated receptor. In addition, it appears that in the light-activated receptor, it is the last seven amino acids of the peptide which are most important (344-350) while the first six amino acids (340-345) are more important for dark-adapted rhodopsin binding.

TABLE IX

Light-Activated Rhodopsin High Affinity Sequences.

| Clone No. | SEQ ID NO: | Sequence |
|---|---|---|
| Library Sequence | 124 | IRENLKDCGLF |
| 8 | 125 | LLENLRDCGMF |
| 9 | 126 | IQGVLKDCGLL |
| 10 | 127 | ICENLKECGLF |
| 18 | 128 | MLENLKDCGLF |
| 23 | 129 | VLEDLKSCGLF |
| 24 | 130 | MLKNLKDCGMF |
| 3 | 131 | LLDNIKDCGLF |
| 4 | 132 | ILTKLTDCGLF |
| 6 | 133 | LRESLKQCGLF |
| 11 | 134 | IHASLRDCGLF |
| 13 | 135 | IRGSLKDCGLF |
| 14 | 136 | IFLNLKDCGLF |
| 15/28 | 137 | IRENLEDCGLF |
| 16 | 138 | IIDNLKDCGLF |
| 17 | 139 | MRESLKDCGLF |
| 19 | 140 | IRETLKDCGLL |
| 26 | 141 | ILADVIDCGLF |
| 27 | 142 | MCESLKECGLF |

TABLE X

Dark-Adapted Rhodopsin High Affinity Sequences.

| Clone No. | SEQ ID NO: | Sequence |
|---|---|---|
| Library Sequence | 124 | IRENLKDCGLF |
| 2 | 143 | IREKWKDLALF |
| 3 | 144 | VRDNLKNCFLF |
| 7 | 145 | IGEQIEDCGPF |
| 17 | 146 | IRNNLKRYGMF |
| 21 | 147 | IRENLKDLGLV |
| 26 | 148 | IRENFKYLGLW |
| 33/37 | 149 | SLEILKDWGLF |
| 41 | 150 | IRGTLKGWGLF |

Example 8

Screens of PAR1 with a Gq Peptide Library

The methods of Example 7 were used to screen different sources of PAR1 receptor using the Gq library. Purified PAR1, reconstituted in lipid vesicles (Example 6), membranes prepared from Sf9 insect cells expressing PAR1 (Example 3) and membranes prepared from mammalian cells overexpressing PAR1 were used. The results of the screens are presented in Tables XI, XII and XIII, respectively. The peptide used as the competitor for all three screens was LQLNLKEYNLV (SEQ ID NO:2). The 4-residue linker sequences are random and are optionally present at the amino terminus of the binding peptide. These results show that the identified high affinity peptides are similar for all three sources of screened PAR1. When a Gq-biased library is used to pan PAR1, the positions that appear to be critical for receptor recognition, and thus are invariant, are N348, L349 and V350.

TABLE XI

Reconstituted Purified Recombinant PAR1 Receptor; Screening Results.

| Clone | Linker | SEQ ID NO: | | SEQ ID NO: |
|---|---|---|---|---|
|  |  |  | LQLNLKEYNLV | 2 |
| R2-16 | *SWV | 151 | LQFNLNDCNLV | 102 |
| R2-17 | FVNC | 152 | LQRNKKQYNLC | 160 |

TABLE XI-continued

Reconstituted Purified Recombinant PAR1 Receptor; Screening Results.

| Clone | Linker | SEQ ID NO: | | SEQ ID NO: |
|---|---|---|---|---|
| R2-18 | EVRR | 153 | MKLKLKEDNLV | 103 |
| R2-20 | *RVQ | 154 | HQLDLLEYNLG | 104 |
| R2-21 | RLTR | 155 | LQLRYKCYNLV | 161 |
| R3-37 | SR*K | 156 | LQQSLIEYNLL | 111 |
| R3-38 | MTHS | 157 | VHVKLKEYNLV | 162 |
| R3-44 | SGPQ | 158 | LQLNVKEYNLV | 163 |
| R3-46 | ML*N | 159 | LRIYLKGYNLV | 164 |

TABLE XII

PAR1 Receptor Sf9 Insect Cell Membranes; Screening Results.

| Clone | Linker | SEQ ID NO: | | SEQ ID NO: |
|---|---|---|---|---|
|  |  |  | LQLNLKEYNLV | 2 |
| S1-13 | S*IR | 165 | MKLNVSESNLV | 94 |
| S1-18 | RWIV | 166 | LQLNLKVYNLV | 175 |
| S1-23 | G*GH | 167 | LELNLKVYNLF | 176 |
| S2-26 | RSEV | 168 | LQLKHKENNLM | 100 |
| S2-30 | CEPG | 169 | LHLNMAEVSLV | 177 |
| S2-36 | HQMA | 170 | LQVNLEEYHLV | 101 |
| S3-6 | VPSP | 171 | LQKNLKEYNMV | 106 |
| S3-8 | QMPN | 172 | LQMYLRGYNLV | 108 |
| S3-10 | MWPS | 173 | LKRYLKESNLV | 178 |
| S3-15 | C*VE | 174 | MNLTLKECNLV | 110 |

TABLE XIII

Mammalian (CHO) Cells Overexpressing PAR1; Screening Results.

| Clone | Linker | SEQ ID NO: | | SEQ ID NO: |
|---|---|---|---|---|
|  |  |  | LQLNLKEYNLV | 2 |
| C4-5 | PRQL | 179 | LQLKRGEYILV | 183 |
| C4-19 | VRPS | 3 | LQLNRNEYYLV | 4 |
| C5-10 | SRHT | 11 | LRLNGKELNLV | 12 |
| C5-12 | FFWV | 180 | CSLKLKAYNLV | 184 |
| C4-16 | QRDT | 181 | LQMNHNEYNLV | 185 |
| C7-3 | NFRN | 182 | PQLNLNAYNLV | 186 |
| C7-10 | LPQM | 9 | QRLNVGEYNLV | 10 |
| C7-13 | LSTN | 7 | LHLNLKEYNLV | 8 |
| C7-14 | LSRS | 5 | LQQKLKEYSLV | 6 |

Example 9

Identification of GPCR-Binding High Affinity Peptide Analogs (Panning)

The methods of Example 7 were repeated using recombinant reconstituted $\beta_2$ adrenergic receptor panned with the Gs Library. Results of the panning screens and ELISA binding affinity of the selected peptides are shown in Table XIV, below.

TABLE XIV

β2-Adrenergic Receptor screened with Gs library.

| | | SEQ ID NO | ELISA |
|---|---|---|---|
| Competitor | QRMHLRQYELL | 13 |  |
| AG1 | QGMQLRRFKLR | 187 | .435 |

TABLE XIV-continued

β2-Adrenergic Receptor screened with Gs library.

|       |             | SEQ ID NO |      |
|-------|-------------|-----------|------|
| AG20  | RWLHWQYRGRG | 188       | .431 |
| AG19  | PRPRLLRFKIP | 189       | .361 |
| AG2   | QGEHLRQLQLQ | 190       | .330 |
| AG4   | QRLRLGPDELF | 191       | .291 |
| BAR1  | QRIHRRPFKFF | 192       | .218 |
| AG3   | QRMPLRLFEFL | 193       | .217 |
| BAR2  | QRVHLRQDELL | 194       | .197 |
| AG11  | DRMHLWRFGLL | 195       | .192 |
| AG9   | QRMPLRQYELL | 196       | .190 |
| BAR3  | QWMDLRQHELL | 197       | .185 |
| AG18  | QRMNLGPCGLL | 198       | .155 |
| BAR20 | NCMKFRSCGLF | 199       | .079 |
| AG13  | QRLHLRGYEFL | 200       | .054 |
| BAR11 | HRRHIGEFALL | 201       | .048 |
| BAR8  | ERLHRRLFQLH | 202       | .047 |
| BAR40 | PCIQLGQYESF | 203       | .028 |
| BAR31 | QRLRLRKYRLF | 204       | .026 |

Example 10

Identification of GPCR-Binding High Affinity Peptide Analogs (Panning)

The methods of Example 7 repeated using rhodopsin screening with a Gt library. Results of the panning screens and ELISA binding affinity of the selected peptides are shown in Table XV, below. To identify the rank order of binding, the lysates were analyzed using ELISA methods in which the secondary antibody was conjugated to HRP. Following addition of the substrate, the microplate was read using a spectrophotometer. The binding is the $OD_{450}$ for wells with receptor—$OD_{450}$ for wells in which no receptor (control wells with empty lipid vesicles).

TABLE XV

Rhodopsin screened with Gt library.

|            |            | SEQ ID NO: |       |       |
|------------|------------|------------|-------|-------|
| Competitor | IRENLKDCGLF | 124       | ELISA |       |
| L33        | IVEILEDCGLF | 205       | 1.007 |       |
| L4         | MLDNLKACGLF | 206       | .908  |       |
| L3         | ILENLKDCGLF | 207       | .839  |       |
| L14        | LRENLKDCGLL | 208       | .833  |       |
| L38        | LLDILKDCGLF | 209       | .823  |       |
| L15        | VRDILKDCGLF | 210       | .621  |       |
| L34        | ILESLNECGLF | 211       | .603  |       |
| L17        | ILQNLKDCGLF | 212       | .600  |       |
| L7         | MLDNLKDCGLF | 213       | .525  |       |
| L10        | IHDRLKDCGLF | 214       | .506  |       |
| L20        | IRGSLKDCGLF | 135       | .423  |       |
| L6         | ICENLKDCGLF | 215       | .342  |       |
| L8         | IVKNLEDCGLF | 216       | .257  |       |

TABLE XV-continued

Rhodopsin screened with Gt library.

|     |            | SEQ ID NO: |      |
|-----|------------|------------|------|
| L13 | ISKNLRDCGLL | 217       | .187 |
| L10 | IRDNLKDCGLF | 218       | .162 |

Example 11

Additional Peptide Analogs

Chinese hamster ovary-expressed PAR1 was screened against the Gt, G12 and G13 libraries, using the competitor peptide indicated in Table XVI below. Additional peptide analogs were identified using the Gt, G12 or G13 library as indicated and IRENLKDCGLF (SEQ ID NO:124), LQEN-LKDIMLQ (SEQ ID NO:38) or LQDNLKQLMLQ (SEQ ID NO:233), respectively as competitor with screening for high affinity binding to PAR1 receptor obtained from Chinese hamster ovary cells as described in Example 1, indicated in Table XVII, below.

TABLE XVI

Peptides Identified with CHO EXPRESSED PAR1.

| Gt library (IRENLKDCGLF; SEQ ID NO:124) | |
|---|---|
| IREFLTDCGLF | 219 |
| IRLDLKDVSLF | 220 |
| ICERLNDCGLC | 221 |
| PRDNTKVRGLF | 222 |
| FWGNLQDSGLF | 223 |
| RRGNGKDCRHF | 224 |

| G12 library (LQENLKDIMLQ; SEQ ID NO:38) | |
|---|---|
| LQENLKEMMLQ | 225 |
| LEENLKYRMLD | 226 |
| LQEDLKGMTLQ | 227 |
| LQETMKDQSLQ | 228 |
| PQVNLKSIMRQ | 229 |
| WQHKLSEVMLQ | 230 |
| LKEHLMERMLQ | 231 |
| LLGMLEPLMEQ | 232 |

| G13 library (LQDNLKQLMLQ; SEQ ID NO:233) | |
|---|---|
| LQDNLRHLMLQ | 234 |
| LQDKINHLMLQ | 235 |
| LQANRKLGMLQ | 236 |
| LIVKVKQLIWQ | 237 |
| MRAKLNNLMLE | 238 |
| LQDNLRHLIQ | 239 |
| LQDNRNQLLF | 240 |

TABLE XVII

PAR1 Binding Peptides Screened using a G11 Library (LQLNLKEYNLV; SEQ ID NO:2)

| CHO EXPRESSED | SEQ ID NO: | Recomb/Reconst | SEQ ID NO: | SF9 EXPRESSED | SEQ ID NO: |
|---|---|---|---|---|---|
| LQLNVKEYNLV | 163 | LQLNVKEYNLV | 163 | LQLNLKVYNLV | 175 |
| LQLNRKNYNLV | 241 | LQLRVKEYKRG | 244 | LQLKHKENNLM | 100 |

TABLE XVII-continued

PAR1 Binding Peptides Screened using a G11 Library
(LQLNLKEYNLV; SEQ ID NO:2)

| CHO EXPRESSED | SEQ ID NO: | Recomb/Reconst | SEQ ID NO: | SF9 EXPRESSED | SEQ ID NO: |
|---|---|---|---|---|---|
| LQLRYKCYNLV | 161 | LQLRYKCYNLV | 161 | LQKNLKEYNMV | 106 |
| LQLDLKESNMV | 242 | LQIYLKGYNLV | 245 | LQVNLEEYHLV | 101 |
| LQLNLKKYNRV | 243 | LQFNLNDCNLV | 102 | LFLNLKEYSLV | 257 |
| LQLRVKEYKRG | 244 | LQRNKKQYNLG | 160 | LELNLKVYNLV | 258 |
| LQRNKKQYNLG | 160 | LQRNKNQYNLG | 254 | LPLNPKEYSLV | 109 |
| LQIYLKGYNLV | 245 | LQQSLIEYNLL | 111 | LPLNLIDFSLM | 259 |
| LQFNLNDCNLV | 102 | LRLDFSEKQLV | 105 | LPRNLKEYDLG | 260 |
| LQYNLKESFVV | 246 | LYLDLKEYCLF | 255 | LRLNDIEALLV | 261 |
| LQQSLIEYNLL | 111 | HQLDLLEYNLG | 104 | LVLNRIEYNLL | 262 |
| LQRDHVEYKLF | 247 | VQVKLKEYNLV | 251 | LHLNMAEVSLV | 177 |
| LVIKPKEFNLV | 248 | MKLKLKEDNLV | 103 | MNLTLKECNLV | 110 |
| IQLNLKNYNIV | 249 | SAKELDQYNLG | 256 | MKLNVSESNLV | 94 |
| HQLDLLEYNLG | 104 | VHVKLKEYNLV | 162 | LKRYLKESNLV | 178 |
| MQLNLKEYNLV | 250 | | | LKRKLKESNMG | 263 |
| VQVKLKEYNLV | 251 | | | LKRKVKEYNLG | 264 |
| QLLNQYVYNLV | 252 | | | LELNLKVYNLF | 176 |
| MKLELKEDNLV | 103 | | | LQMYLRGYNLV | 108 |
| WRLSLKVYNLV | 253 | | | | |
| LQLKRGEYILV | 183 | | | | |
| LQLNRNEYYLV | 4 | | | | |
| LRLNGKELNLV | 12 | | | | |
| CSLKLKAYNLV | 184 | | | | |
| LQMHNEYNLV | 185 | | | | |
| PQLNLNAYNLV | 186 | | | | |
| QRLNVGEYNLV | 10 | | | | |
| LHLNLKEYNLV | 8 | | | | |
| LQQKLKEYSLV | 6 | | | | |

Example 12

Preparation of LacI Lysates

In the last round of panning, several clones were selected from the (+) receptor plates and grown up overnight in LB-Amp media. Three hundred microliters of the overnight culture was diluted in 3 mL LB-Amp media for "ELISA lysate culture." Another 30 μL was added to an equal volume of 50% glycerol was stored in labeled microcentrifuge tubes at −70° C. The remaining 4.5 mL was used to make DNA using a standard miniprep protocol (Qiagen Spinprep™ kits) and sequenced using a 19 base pair reverse primer which is homologous to the vector at a site 56 basepairs downstream from the TAA stop codon that terminates the random region of the library (GAAAATCTTCTCTCATCCG; SEQ ID NO:265). The DNA was stored at −20° C. The ELISA lysate culture was allowed to shake for one hour at 37° C. Expression was induced by adding 33 μL 20% arabinose (0.2% final concentration) with shaking at 37° C. for 2-3 hours. The culture then was subjected to sedimentation at 4000×g for five minutes, the pellet resuspended in 3 mL cold WTEK buffer, resedimented at 4000×g for five minutes and the pellet resuspended in 1 mL cold TEK buffer. After transfer to 1.5 mL microcentrifuge tubes, the pellet was sedimented at 13,000×g for two minutes and the supernatant aspirated. The cell pellet was resuspended in 1 mL lysis buffer (42 mL HE, 5 mL 50% glycerol, 3 mL 10 mg/mL BSA in HE, 750 μL 10 mg/mL lysozyme in HE and 62.5 μL 0.2 M PMSF) and incubated on ice for one hour. One hundred ten microliters 2M KCl was added to the lysis mixture and inverted to mix, then sedimented at 13,000×g for 15 minutes at 4° C. The clear crude lysate (about 0.9 mL supernatant) was transferred to a new tube and stored at −70° C.

Example 13

PAR1 Receptor-Specific Binding of LacI-Peptide Fusion Proteins

Figure 4:
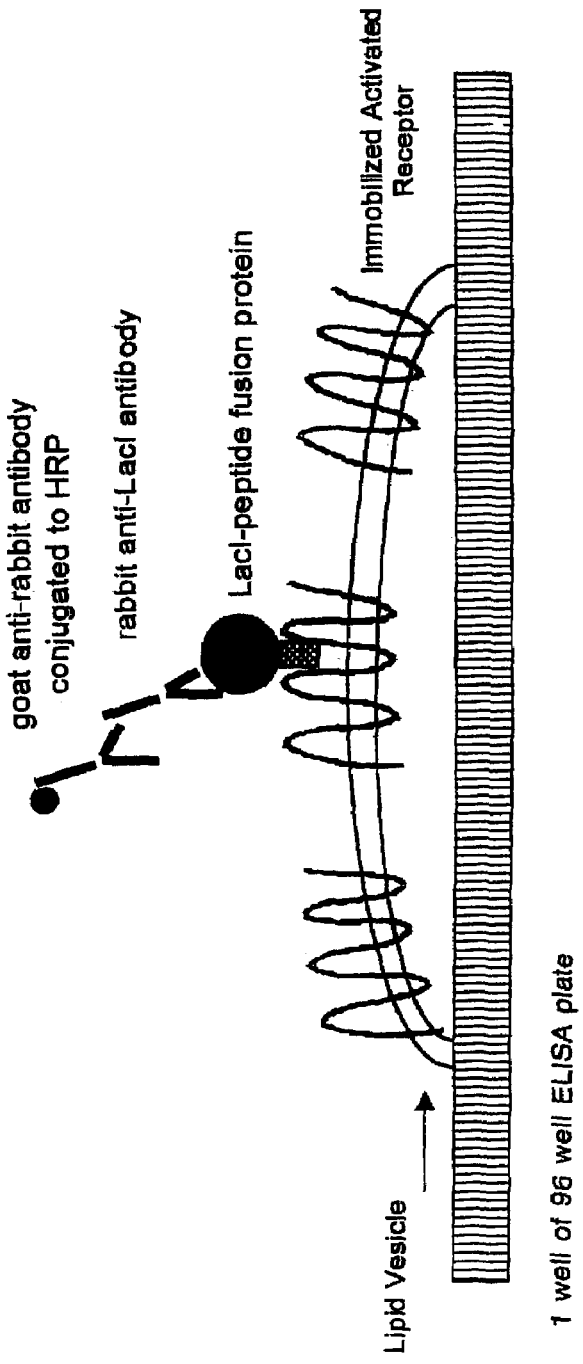
FIG. 4 is a schematic diagram showing an ELISA procedure.
Figure 5:
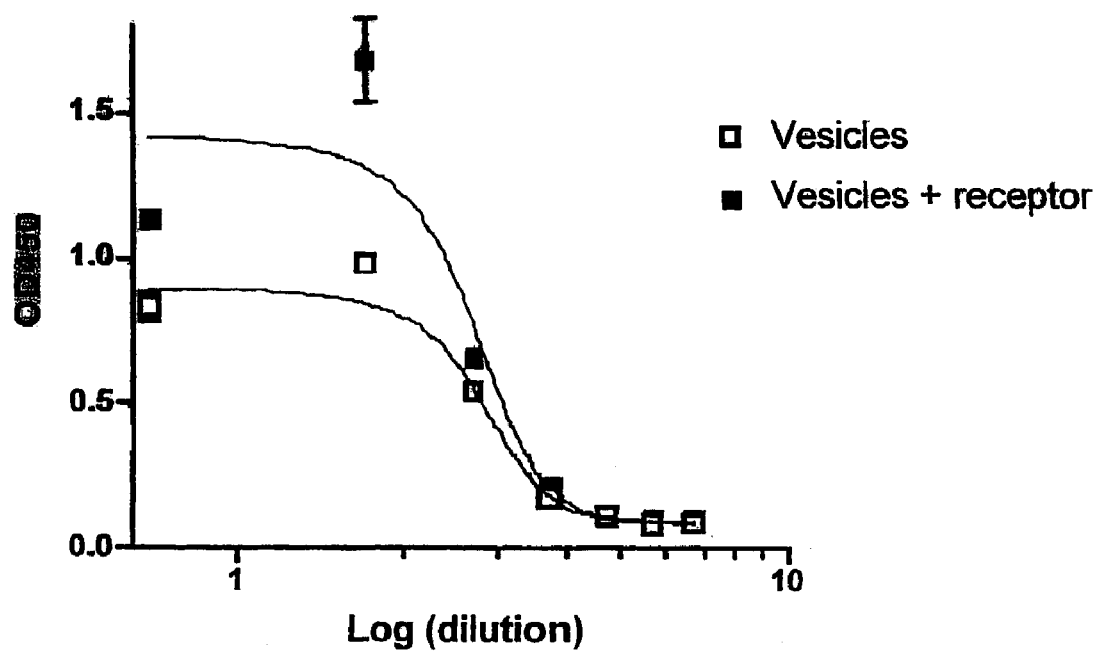
FIG. 5 provides results showing that the LacI-Gq fusion protein binds thrombin receptor in a concentration-dependent manner.

The binding properties of the peptide encoded by individual clones were assayed as follows. Purified PAR1 receptor prepared from Sf9 insect cells (1-10,000 pg/mL in 50 mM Tris-HCl, pH 7.4, 10% glycerol) was reconstituted in lipid vesicles according to Example 6. A serial dilution of the membranes containing receptor ranging from 0.2 to 20,000 μg/mL (+/− receptor) was added to wells on a microtiter plate and shaken gently for one hour at 4° C. After washing, a 1:1 to 1:10,000 serial dilution of a LacI-Gq lysate prepared from the LacI-Gq clone according to the methods described in Example 12 was added to the wells, the plate was shaken gently for one hour at 4° C., and washed. Anti-LacI antibodies (Stratagene) were added (1:1000) and the plate shaken gently for one hour at 4° C. After washing, HRP-conjugated goat anti-rabbit antibodies (Kierkegaard and Perry Laboratories) were added (1:2500) and the plate shaken gently for one hour at 4° C. The plate was washed, color was developed using horseradish peroxidase, and then read in an ELISA reader at $OD_{450}$. The general methodology for the ELISA is illustrated in FIG. 4. The results, see FIG. 5, show that the LacI-Gq fusion protein binds thrombin receptor in a concentration-dependent manner. The ability of the LacI-Gq fusion protein to bind the empty vesicles was significantly less than vesicles reconstituted with thrombin receptor.

Example 14

Screening in the Presence of a High Affinity Peptide

To identify peptides having even higher affinity to light-activated rhodopsin than those identified by the panning procedure described in Example 7, a high affinity peptide was included in the library incubations in rounds three and four. Peptide 8 (LLENLRDCGMF; SEQ ID NO:125) had been identified in the first screening as a peptide exhibiting binding to light-activated rhodopsin 1000-fold higher than the native sequence. Screening of the Gαt library was performed as in Example 7, except that 10 µL 100 µM (100 nM final concentration) peptide 8 was included in the wells in rounds three and four. This screen revealed several clones that both bind rhodopsin with very high affinity and stabilize it in its active form, metarhodopsin II. See Table XVIII, below. Comparing Tables IX and XVIII, it is clear using peptide 8 in the screen resulted in a change at position 341 to a neutral residue. Residues L344, C347 and G348 remained stable whether peptide 8 was included in the screen or not. Use of peptide 8 resulted in a higher incidence of isoleucine at position 340 (17% with native peptide versus 71% with peptide 8) and a lower incidence of glutamine at position 342 (67% with native peptide versus 29% with peptide 8) This type of information not only contributes to the discovery of highly potent analog peptides for use as drugs or drug screening compounds, but also furthers the understanding of the structural framework which underlies the sites of contact between Gα and receptor.

Figure 6:
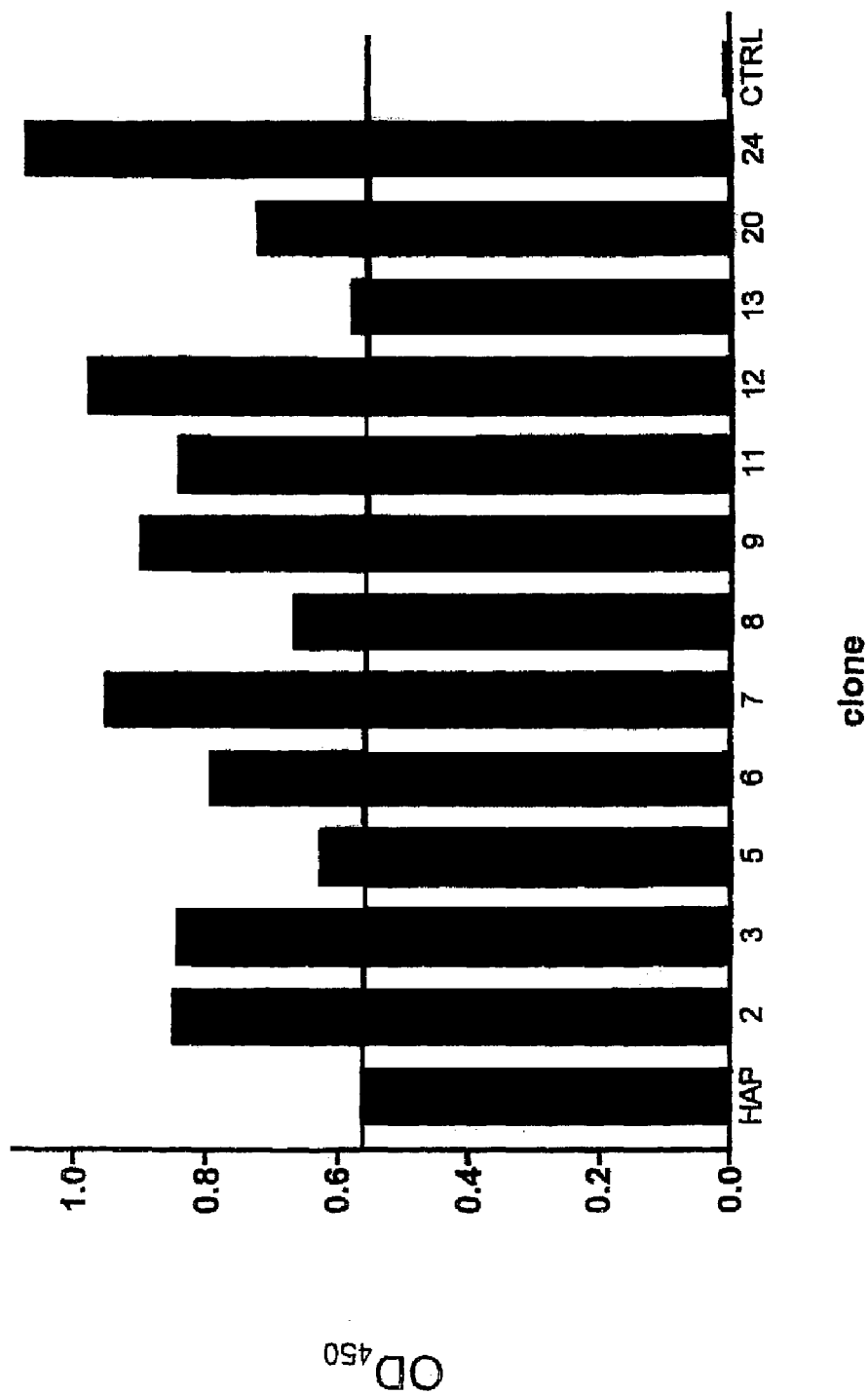
FIG. 6 shows data from binding assays performed on some of the clones identified using peptide 8 in the screening process.

Binding assays performed on some of the clones identified in this way are shown in FIG. 6. All peptides identified using peptide 8 in the screening process bound with equal or greater affinity to light-activated rhodopsin as did peptide 8. Compare the first bar (HAP=peptide 8) with the remaining bars.

TABLE XVIII

Exemplary Light-Activated Rhodopsin High Affinity Sequences Identified in Screens with Addition of Peptide 8.

| Clone No. | SEQ ID NO: | Sequence |
|---|---|---|
| Library Sequence | 124 | IRENLKDCGLF |
| Peptide 8 | 125 | LLENLRDCGMF |
| 3 | 266 | ILENLKDCGLL |
| 7 | 213 | MLDNLKDCGLF |
| 8 | 216 | IVKNLEDCGLF |
| 10 | 218 | IRDNLKDCGLF |
| 13 | 217 | ISKNLRDCGLL |
| 17 | 212 | ILQNLKDCGLF |
| 19 | 206 | MLDNLKACGLF |

Example 15

Subcloning into MBP Vectors and Preparation of MBP Crude Lysates pELM3 was digested at room temperature with AgeI (New England Biolabs) and the cut vector was separated from uncut vector on a 0.7% agarose gel. DNA was purified (Qiagen Extract-a-gel kit) and digested with ScaI (New England Biolabs). The 5.6 kb MBP vector fragment was separated on a 1% agarose gel and purified as above. During the final affinity purification round of the peptide library, a 20 mL portion of the 200 mL amplification culture was set aside before harvesting the cells. This 20 mL portion was allowed to grow to saturation, usually overnight, and DNA was prepared from the cells (Qiagen midi-prep kit). The pJS142 plasmid DNA was digested with BspEI and ScaI. The 0.9 kb peptide-encoding fragment was separated from the 3.1 and 1.7 kb vector fragments on a 1% agarose gel and purified.

Different ratios of the 5.6 kb MBP vector fragment and the peptide-encoding 0.9 kb fragment (1:2, 1:1, 2.5:1, 5:1, 10:1) were ligated in ligase buffer containing 0.4 mM ATP at 14° C. overnight with T4 DNA ligase. The ligation was terminated by increasing the temperature to 65° C. for ten minutes. To lower the background, the ligation mixture was digested with XbaI before isopropanol precipitation using 1 µL glycogen as a carrier. After one wash with 80% ethanol, the pellet was resuspended in 20 µL double-distilled water. ARI814 cells were transformed as described in Example 7 using 1 µL of the precipitated XbaI digested ligation mix. After allowing the cells to shake for one hour at 37° C. in 1 mL SOC, 100 µL of the suspension was spread on LB-Amp Plates. Crude lysates were prepared as described for LacI lysates in Example 12.

Example 16

MBP-Peptide Fusion Protein Purification

An overnight culture (1 mL) of a single MBP-peptide fusion protein clone was inoculated into 200 mL LB-AMP media. The culture was shaken at 37° C. until $OD_{600}$=0.5. Protein expression was induced by addition of 150 µL 1 M IPTG (final concentration 0.3 mM), with continued shaking at 37° C. for two hours. The culture then was sedimented at 5000×g for 20 minutes and resuspended in 5 mM column buffer (10 mM Tris, pH 7.4; 200 mM NaCl; 1 mM EDTA; 1 mM DTT) and 16.25 µL 0.2 M PMSF was added. The resuspended cell pellet was then stored at −70° C. The stored pellet was thawed in cold water and placed in an ice bath. The pellet was sonicated in short pulses of less than 15 seconds with a Fisher Scientific 55 Sonic Dismembrator (40% constant time, output 5, repeating five times with a total one minute duration). The sonicated pellet was subjected to centrifugation at 9000×g for 30 minutes, after which the supernatant was saved and diluted to 100 mL using column buffer. Usually, the protein concentration was approximately 2.5 mg/mL. A column was prepared by pouring 7.5 ml amylose resin in a BioRad disposable column and washing with eight volumes of column buffer. The diluted crude extract was loaded by gravity flow at about 1 mL/min and the column was washed again with eight volumes of column buffer. The fusion protein was eluted with 10 mL 10 mM maltose in column buffer and concentrated using Amicon centriplus 30™ columns, then aliquoted and stored at −70° C.

Example 17

Method for Screening Library Crude Lysates by ELISA

Microtiter wells were coated with 0.1-1.0 µg/well rhodopsin receptor in a final volume of 100 µL HEK containing 1 mM DTT with shaking at 4° C. for one hour. The wells then were blocked with bovine serum albumin (BSA) by adding 100 μL 2% BSA in HEK with 1 mM DTT to the wells and continuing shaking at 4° C. for at least 30 minutes, then washed four times with HEK containing 1 mM DTT. Crude lysates were diluted 1:50 in HEK containing 1 mM DTT and added to the coated wells (100 μL per well). The plates were shaken at 4° C. for one hour, washed four times with PBS/0.05% Tween™20 1 mM maltose and then probed with 100 μL 1:1000 rabbit anti-MBP antibodies (New England BioLabs) in PBS containing 0.05% Tween™ 20 and 1 mM maltose, with shaking for 30 minutes at 4° C. After another wash, the wells were probed with 100 μL 1:7500 goat anti-rabbit secondary antibodies conjugated to horseradish peroxidase in PBS containing 1% BSA and 1 mM maltose with shaking for 30 minutes at 4° C. The plate was washed four times with PBS containing 0.05% Tween™ 20 and 1 mM maltose. Horseradish peroxidase substrate (Bio-Fx; 100 μL) was added and the color developed for 20-30 minutes. The reaction was stopped by addition of 100 μL 2N sulfuric acid and the plate read at $OD_{450}$. If the color reaction occurred too quickly (less than 10 minutes) or if the background in negative control wells was too high (greater than 0.2) the assay was repeated using 1:100 or 1:200 dilutions of the crude lysates.

Example 18

Binding Assay of High Affinity Rhodopsin Binding Peptide Fusion Proteins

The entire population of peptide-coding sequences identified in round 4 of panning (see Example 7) was transferred from pJS142 to pELM3 (New England Biolabs). This plasmid is a pMal-c2 derivative with a modified polylinker, inducible by isopropyl β-thiogalacto-pyranoside and containing the *E. coli* malE gene with a deleted leader sequence and leads to cytoplasmic expression of MBP fusion proteins. The MBP-carboxyl terminal peptide analog fusion proteins were expressed in *E. coli*.

Figure 7:
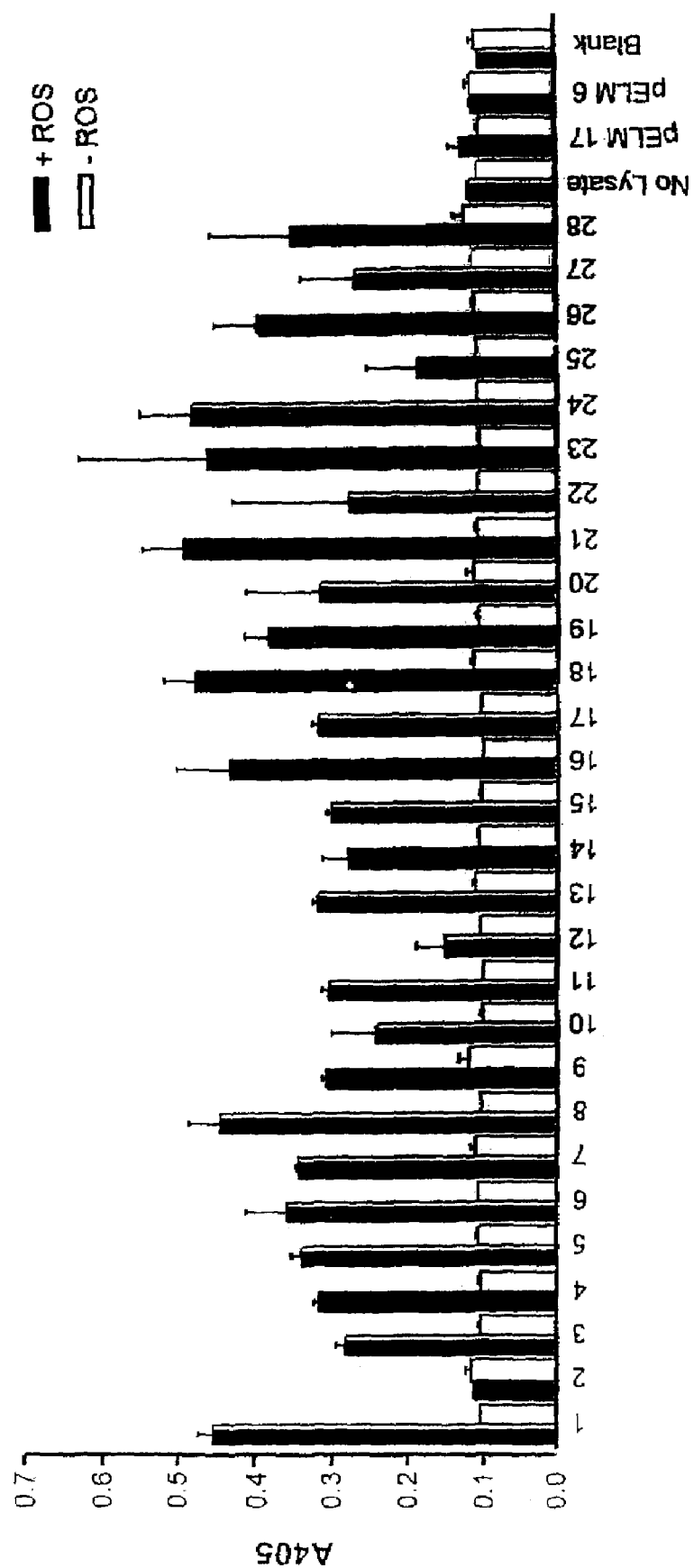
FIG. 7 provides binding data for LacI peptide fusion proteins to PAR1 receptor. pELM6 is the MBP vector alone; pELM17 is the MBP-native Gt340-350 peptide fusion protein.

For the assay, in the dark, 1 μg/well of ROS membranes (rhodopsin) as described in Example 5 was directly immobilized on microtiter wells in cold HEK/DTT for one hour at 4° C. The wells were rinsed, blocked with 1% BSA in HEK/DTT for one hour at 4° C. and rinsed again. Bound rhodopsin was activated by exposure to light for 5 minutes on ice before addition of the MBP fusion proteins (crude bacterial lysates were diluted 1:50 in HEK with 1 μM dithiothreitol; purified proteins were used at 0.2-120 nM). The MBP-Gαt340-350K341R (pELM17) fusion protein and MBP with linker sequence only (pELM6) were present in control wells at 50 nM final concentration. After 30 minutes, wells were washed and rabbit anti-MBP antibody (New England Biolabs) was added. The anti-MBP antibody was used at a 1:1000 dilution for crude lysates and a 1:3000 dilution for purified proteins. After 30 minutes, wells were rewashed and goat anti-rabbit antibody conjugated to horseradish peroxidase (1:7500 dilution for crude lysates; 1:10,000 dilution for purified proteins; Kierkagaard & Perry Laboratories) was added. After 30 minutes, the plate was washed four times with PBS containing 0.05% Tween™20. Horseradish peroxidase substrate (100 μl) was added and color was allowed to develop for about 20 minutes. The reaction was stopped by addition of 100 μl 2N sulfuric acid. The results are presented in FIG. 7. Values indicate absorbance at $OD_{450}$. The positive control for the assay was pELM 17, which encodes the MBP fusion protein Gαt340-350K341R. pELM6, which expresses MBP protein fused to a linker sequence only, served as the negative control. "No lysate" control wells were included to reflect any intrinsic, non-specific binding within the assay. See FIG. 7.

The $IC_{50}$ values of the high affinity MBP fusion proteins ranged from 3.8 to 42 nM, up to 3 orders of magnitude more potent than the 6 μM $IC_{50}$ of MBP-Gαt340-350K341R. In all the highest affinity sequences, position 341, which is a positively charged residue in the native sequence, was changed to a neutral residue. Leu344, Cys347, and Gly348 were found to be invariant and hydrophobic residues were always located at positions 340, 349, and 350, indicating the critical nature of these residues.

Example 19

Binding of High Affinity Peptide Fusion Proteins to Rhodopsin can be Competitively Inhibited by Heterotrimeric Gt When light-activated rhodopsin was screened for peptides based on the C-terminus of Gt, a large number of high-affinity sequences were obtained. Binding of MBP fusion proteins containing the high affinity peptide from the library (sequences from clones 8, 9, 10, 18, 23, 24, as well as pELM17 which encodes the wild-type peptide sequence, and pELM6 which contains no peptide; MBP-8, MBP-9, MBP-10, MBP-18, MBP-23, MBP-24, MBP-pELM17) were assessed for their ability to bind rhodopsin (0.5 μg rhodopsin/well) in the presence or absence of heterotrimeric Gt.

Figure 8:
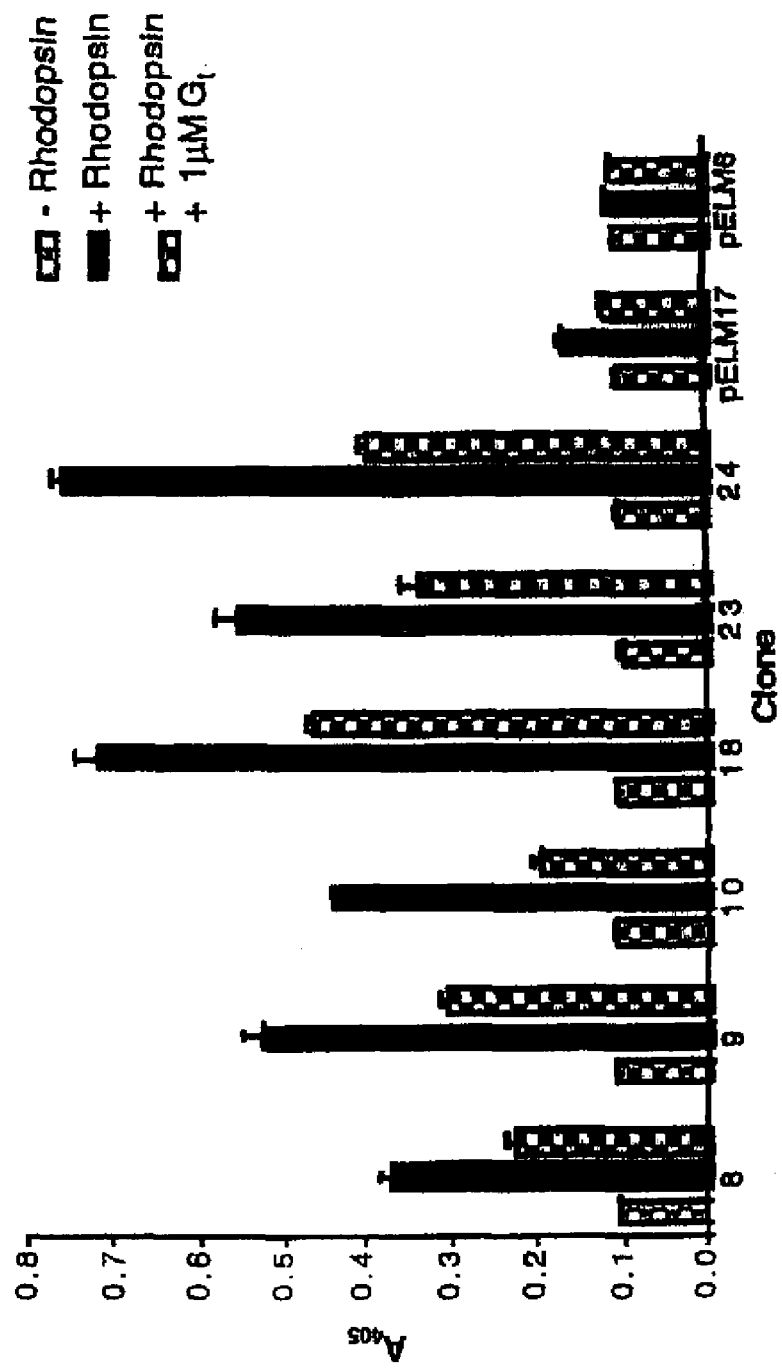
FIG. 8 is a bar graph comparing binding of high affinity fusion proteins to the high affinity peptide 8 fusion protein (MBP 8).

Lysate (50 μl) from each clone was added and incubated in the light. After 45 minutes, 1 μM heterotrimeric Gt was added and the solution incubated for 30 minutes. Anti-MBP antibody was added, followed by goat anti-rabbit alkaline phosphatase conjugated antibody and substrate. The color was allowed to develop. Absorbance data are presented in FIG. 8.

Most peptide sequences obtained were highly homologous to the native Gαt C-terminal sequence. Several of these sequences are of very high affinity (>1000-fold higher than the parent peptide) and are potent and specific antagonists of receptor-mediated G protein activation. The high-affinity peptide fusion proteins were tested for binding to light-activated rhodopsin and for their ability to stabilize the MII conformation (Table XXI).

The screen used MBP-8 because this peptide bound to rhodopsin with high affinity and stabilized MII. MBP-18 and MBP-24, which both showed even higher binding affinities than did MBP-8 to rhodopsin, were not used because the affinity was so high that the small molecules might not have been able to competitively inhibit their binding. Of course, the screen may be repeated using another peptide as is convenient, for example peptides that are of higher affinity to find even more potent small molecules.

TABLE XIX

Absorbance at $OD_{450}$ in a Panning ELISA and EC50 values for MII binding and MII Stabilization for Selected MBP-High Affinity Peptide Fusion Proteins.

| | | SEQ ID NO: | ELISA $OD_{450}$ | MII binding $EC_{50}$ | MII stabilization $EC_{50}$ |
|---|---|---|---|---|---|
| Gt | IKENLKDCGLF | 15 | .01 | 6000 nM | >100 μM |
| 9 | LQQVLKDCGLL | 267 | .35 | 10 nM | 1.05 μM |

TABLE XIX-continued

Absorbance at $OD_{450}$ in a Panning ELISA and EC50 values for MII binding and MII Stabilization for Selected MBP-High Affinity Peptide Fusion Proteins.

| | | SEQ ID NO: | ELISA $OD_{450}$ | MII binding $EC_{50}$ | MII stabilization $EC_{50}$ |
|---|---|---|---|---|---|
| 10 | ICENLKDCGLF | 215 | .36 | 42 nM | 5.40 μM |
| 8 | LLENLRDCGMI | 268 | .54 | 7.8 nM | 0.94 μM |
| 18 | MLENLKDCGLF | 128 | .58 | 3.8 nM | 1.24 μM |
| 24 | MLKNLKDCGMF | 130 | .61 | 6.6 nM | 0.49 μM |
| 23 | VLEDLKSCGLF | 129 | .66 | 20 nM | 3.50 μM |

Heterotrimeric Gt competitively inhibited high affinity peptide fusion protein binding to light-activated rhodopsin. See FIG. 8. The heterotrimeric Gt contains multiple determinants of rhodopsin binding and is membrane bound via myristoylation of the α subunit and farnesylation of the γ subunit carboxyl terminus. Thus, the selected peptide sequences from the combinatorial library bind to the receptor with very high affinity.

Example 20

Binding of MBP Clones to PAR1

Figure 9:
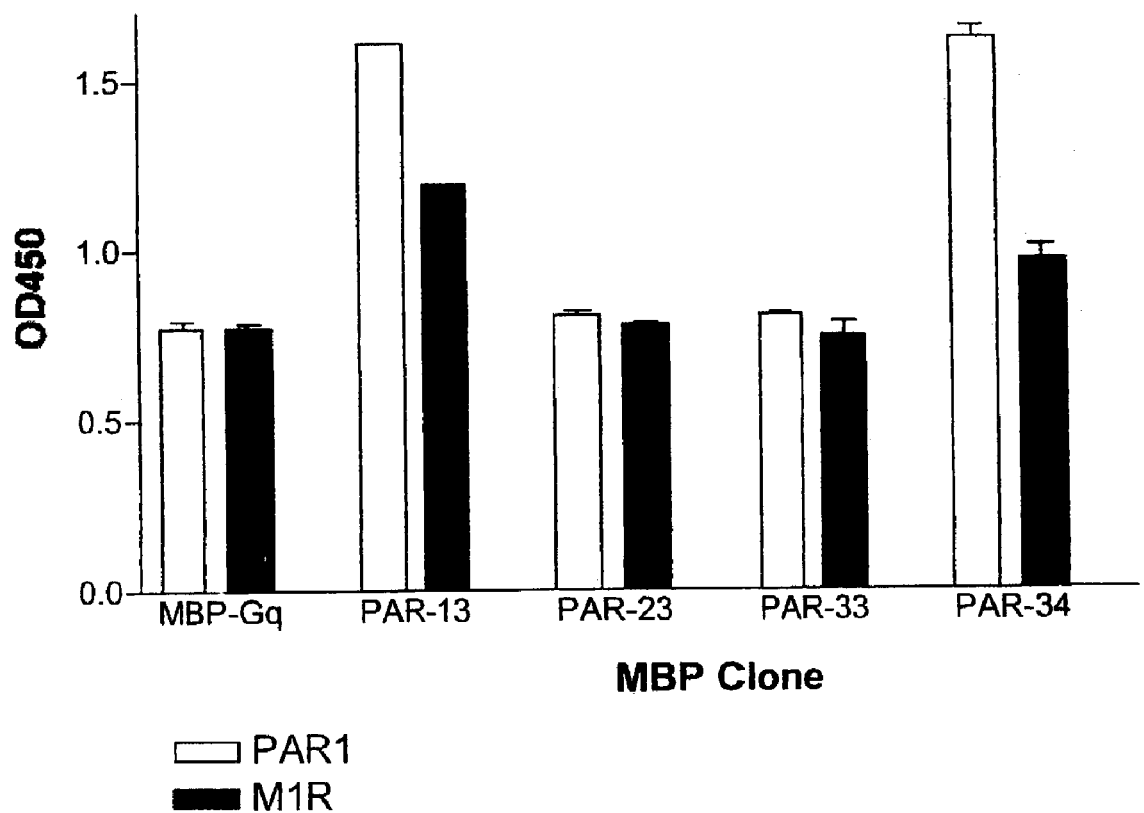
FIG. 9 presents ELISA results from panning CHO cells overexpressing human thrombin receptor (PAR1) using purified MBP-C-terminal fusion proteins. MBP-G11=xxxx (SEQ ID NO: 1) LQLNLKEYNLV (SEQ ID NO: 2); PAR-13=VRPS (SEQ ID NO: 3) LQLNRNEYYLV (SEQ ID NO: 4); PAR-23=LSRS (SEQ ID NO: 5) LQQKLKEY-SLV (SEQ ID NO:6); PAR-33=LSTN (SEQ ID NO: 7) LHLNLKEYNLV (SEQ ID NO: 8); PAR-34=LPQM (SEQ ID NO: 9) QRLNVGEYNLV (SEQ ID NO: 10); PAR-45=SRHT (SEQ ID NO: 11) LRLNGKELNLV (SEQ ID NO:12).

To identify high affinity peptides that bind PAR1, membranes prepared from mammalian cells (Chinese hamster ovary) overexpressing PAR1 were panned with the G11 peptide library. ELISA binding affinity results of selected clones are shown in FIG. 9 for their binding to membranes prepared from SF9 cells expressing either PAR1 or the Gq-coupled muscarinic M1 receptor. To quantitate the binding, purified MBP clones were analyzed using ELISA methods in which the secondary antibody was conjugated to HRP. The binding for the control MBP-Gq fusion protein is shown. See FIG. 9. The data are the average of two separate experiments done in duplicate. MBP clones PAR-13 and PAR-34 both show both high affinity binding for PAR1 as well as specificity. MBP clones PAR-23 and PAR-33 appear to be both of low affinity and low specificity. See Table XIII for the sequences.

Example 21

Binding Specificity of LacI-Peptide Fusion Proteins

Figure 10:
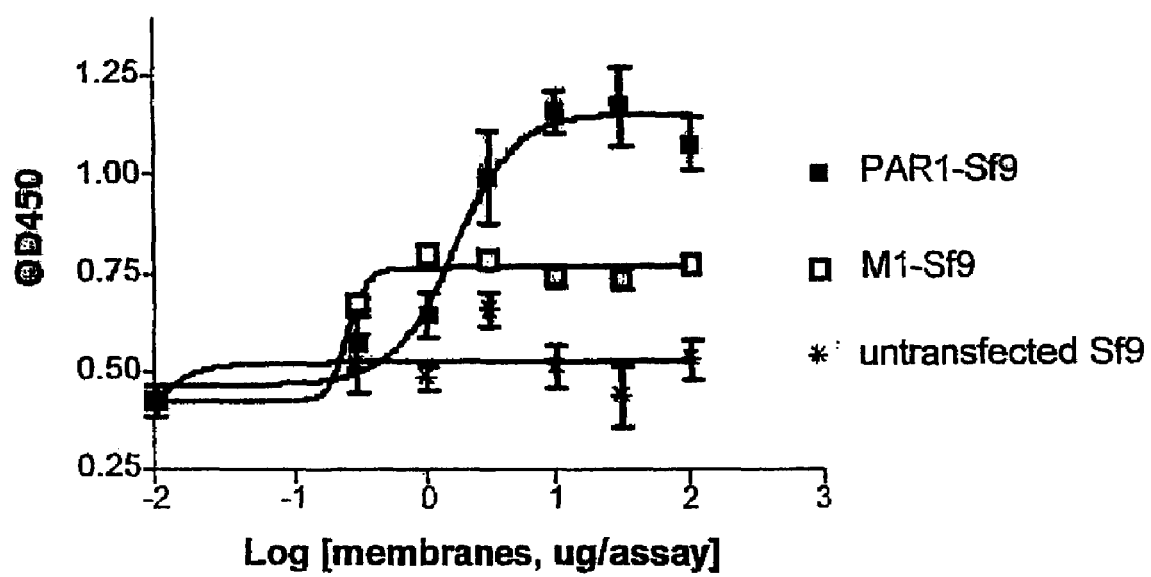
FIG. 10 presents a dose-response curve of SF9 membranes (PAR1 receptor) assayed with lacI-Gq lysates.

PAR1 binding clones of LacI-peptide fusion protein selected from the G11 Library were diluted 1:100 in HEK/DTT and tested for dose-responsive binding to Sf9 insect cell membranes from cells expressing no receptor, the M1 receptor (which couples to Gi) or PAR1 receptor, prepared according to Example 3. Increasing amounts of membrane as indicated in FIG. 10 were coated in microtiter wells, incubated and rinsed. LacI-peptide fusion protein lysates were added, incubated and rinsed, and the receptor-bound LacI-peptide fusion protein was measured as described above using a LacI antibody. Results for a single, representative clone are presented in FIG. 10, and demonstrate the specificity of the selected peptides for PAR1.

Example 22

Binding of Native Gαq-Maltose Binding Protein-Peptide Fusion Protein to PAR1

Figure 11:
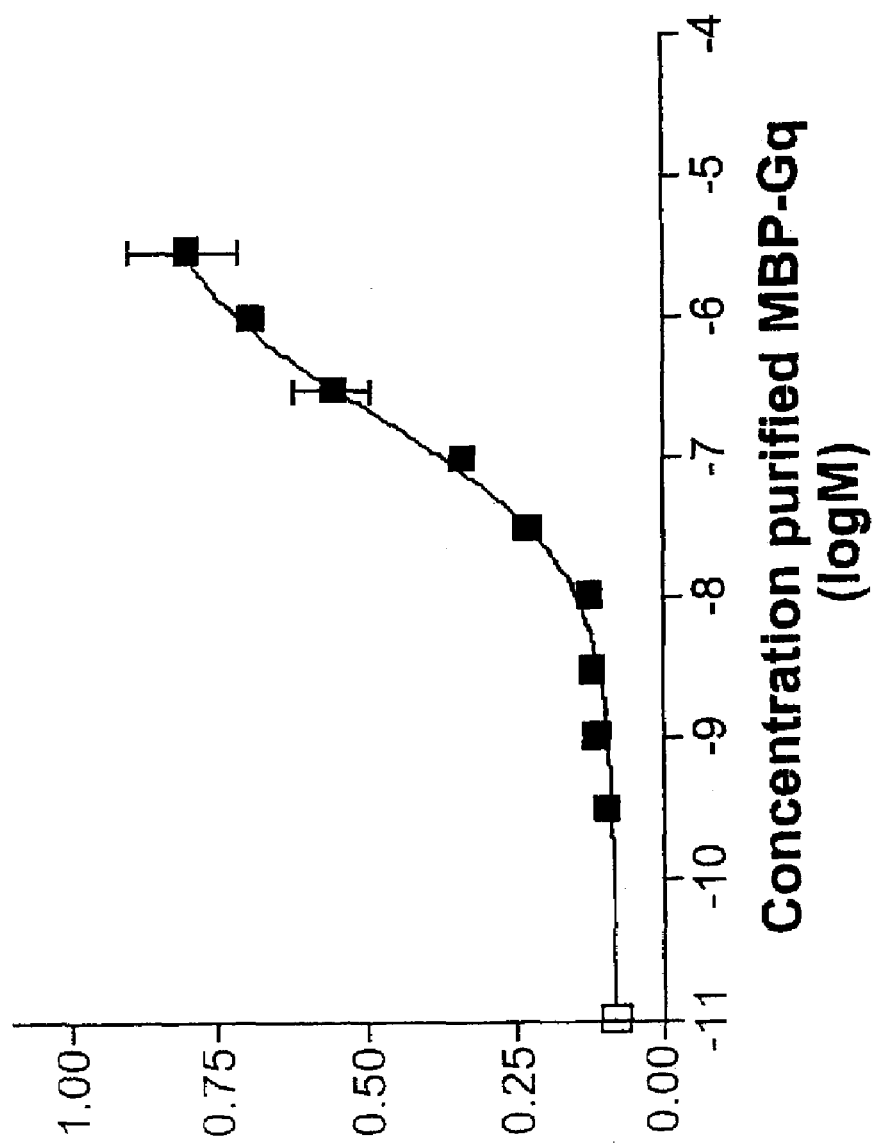
FIG. 11 is a concentration response curve demonstrating binding of native Gq peptide-maltose binding protein to PAR1 reconstituted in lipid vesicles.

Microtiter wells were coated with purified, reconstituted PAR1 in the presence of 100 mmoles thrombin receptor activating peptide, as described above in Example 6. Purified maltose binding protein-Gαq (MBP-Gαq) was added at the concentrations indicated in FIG. 11 and incubated one hour on a shaker at 4° C. The wells were rinsed and then probed with a rabbit anti-maltose binding protein antibody, followed by alkaline phosphatase conjugated secondary antibodies, as described above. Substrate was added and the color was allowed to develop about 20 minutes. Absorbance at 405 nm was measured and dose-response curves were calculated using GraphPad Prism (version 2.0). See results in FIG. 11. The calculated $IC_{50}$ of Gαq binding to activated PAR1 was 214 nM.

Example 23

Figure 12:
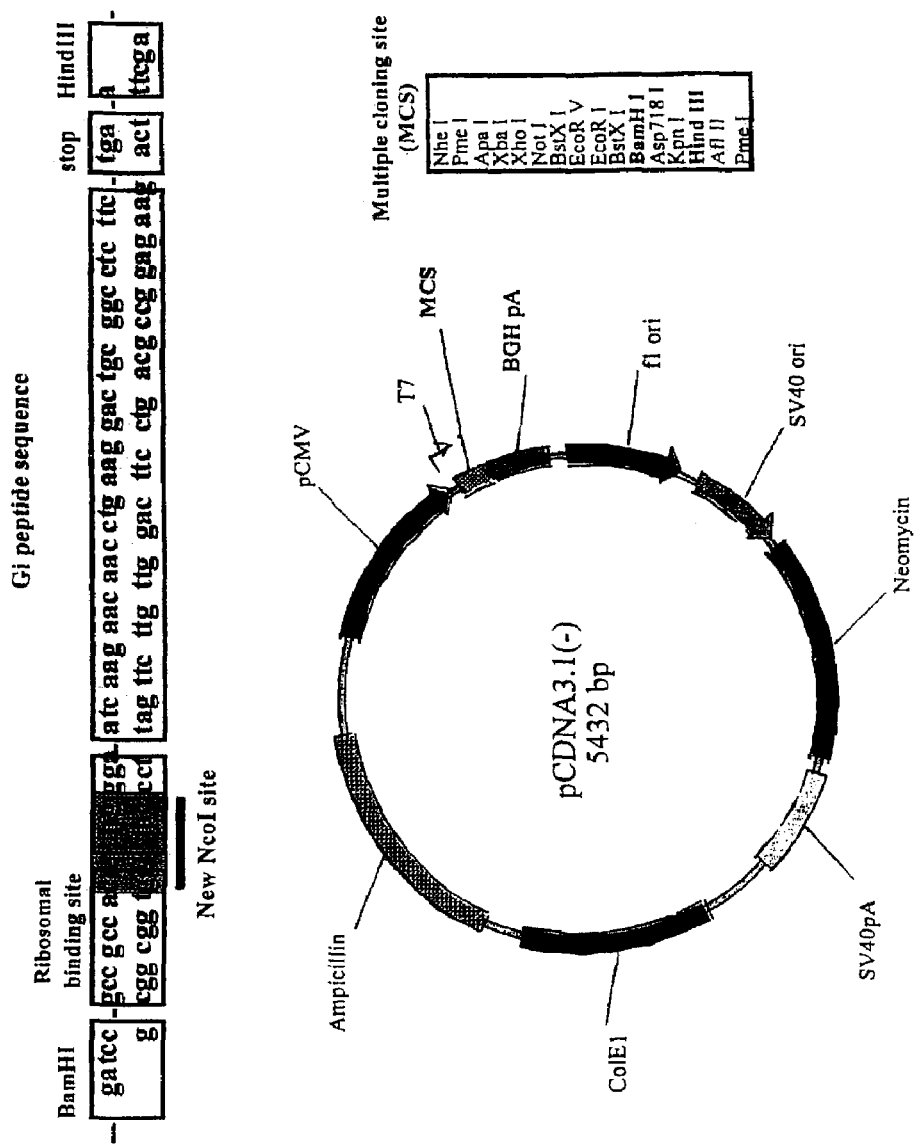
FIG. 12 is a schematic diagram showing an exemplary cDNA minigene construct. SEQ ID NOS:270 and 271 are shown.

Design of Oligonucleotides for Gα Peptide Minigene Constructs cDNA encoding the last 11 amino acids of Gα subunits was synthesized (Great American Gene Company) with newly engineered 5'- and 3'-ends. The 5'-end contained a BamHI restriction enzyme site followed by the human ribosome-binding consensus sequence (5'-GCCGCCACC-3'; SEQ ID NO:269), a methionine codon (ATG) for translation initiation, and a glycine codon (GGA) to protect the ribosome binding site during translation and the nascent peptide against proteolytic degradation. A HindIII restriction enzyme site was synthesized at the 3' end immediately following the translational stop codon (TGA). Thus, the full-length 56 bp oligonucleotide for the $G\alpha_{i1/2}$ carboxyl terminal sequence was 5'-gatccgccgccaccatgggaatcaagaa-caacctgaaggactgcggcctcttctgaa-3' (SEQ ID NO:270) and the complimentary strand was 5'-agctttcagaagaggccgcagtcct-tcaggttgttcttgattcccatggtggcggcg-3' (SEQ ID NO:271). See FIG. 12. As a control, oligonucleotides encoding the $G\alpha i_{1/2}$ carboxyl terminus in random order (GαiR) with newly engineered 5'- and 3'-ends also were synthesized.

The DNA was diluted in sterile $ddH_2O$ to form a stock concentration at 100 μM. Complimentary DNA was annealed in 1×NEBuffer 3 (50 mM Tris-HCl, 10 mM $MgCl_2$, 100 mM NaCl, 1 mM DTT; New England Biolabs) at 85° C. for 10 minutes then allowed to cool slowly to room temperature. The DNA then was subjected to 4% agarose gel electrophoresis and the annealed band was excised. DNA was purified from the band using a kit, according to the manufacture's protocol (GeneClean II Kit, Bio101). After digestion with each restriction enzyme, the pcDNA 3.1(-) plasmid vector was subjected to 0.8% agarose gel electrophoresis, the appropriate band cut out, and the DNA purified as above (GeneClean II Kit, Bio101). The annealed/cleaned cDNA was ligated for 1 hour at room temperature into the cut/cleaned pCDNA 3.1 plasmid vector (Invitrogen) previously cut with BamHI and HindIII.

Figure 13:
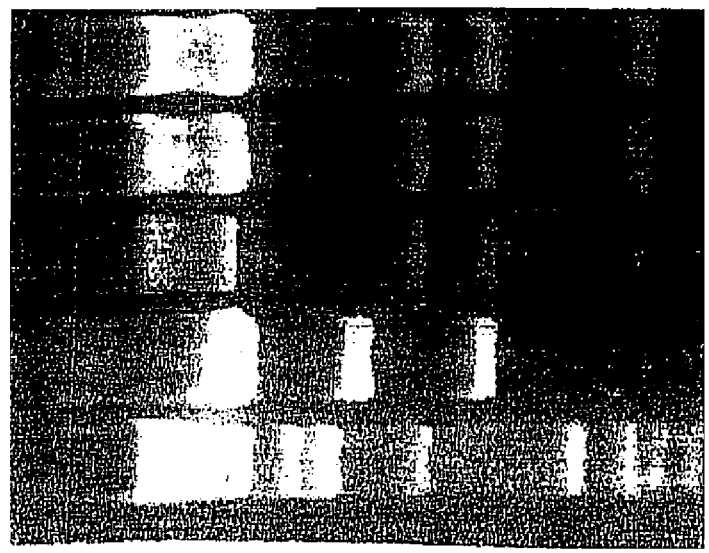
FIG. 13 is an agarose gel of a NcoI digest of minigene vector. Lane 1 is a 1 kb DNA ladder; lane 2 is pcDNA 3.1; lane 3 is pcDNA-Gαi; lane 4 is pcDNA-GαiR; and lane 5 is pcDNA-Gαq.

For the ligation reaction, several different ratios of insert to vector cDNA (ranging from 25 μM:25 pM to 250 pM:25 pM annealed cDNA) were plated. Following the ligation reaction, the samples were heated to 65° C. for 5 min to deactivate the T4 DNA ligase. The ligation mixture (1 μl) was electroporated into 50 μl competent cells as described in Example 7 and the cells immediately placed into 1 ml of SOC (Gibco). After 1 hour shaking at 37° C., 100 μl of the electroporated cells containing the minigene plasmid DNA was spread on LB/Amp plates and incubated at 37° C. for 12-16 hours. To verify that insert was present, colonies were grown overnight in LB/Amp and their plasmid DNA purified (Qiagen SpinKit). The plasmid DNA was digested with NcoI (New England Biolabs, Inc.) for 1 hour at 37° C. and subjected to 1.5% (3:1) agarose gel electrophoresis. Vector alone produced 3 bands. When the 56 bp annealed oligonucleotide insert is present, there is a new NcoI site resulting in a shift in the band pattern such that the digest pattern goes from three bands (3345 bp, 1352 bp, 735 bp) to four bands (3345 bp, 1011 bp, 735 bp, 380 bp). See FIG. 13. DNA with the correct electrophoresis pattern was sequenced to confirm the appropriate sequence. This method may be used to insert any high affinity peptide to create a minigene constant.

Example 24

Expression of Peptides from Minigene Constructs

Expression of the GPCR binding peptides was achieved using constructs which included minigene inserts corresponding to the carboxyl terminal sequences of various G protein α subunits (Gαi, Gαo, Gαs, Gαq, Gα11, Gα12, Gα13, Gα14), as well as a control minigene containing the Gαi sequence in random order (GαiR). The minigene insert DNAs were made by synthesizing short complimentary oligonucleotides corresponding to the peptide sequences from the carboxyl terminus of each Gα with BamHI and HindIII restriction sites at the 5' and 3' ends, respectively. Complementary oligonucleotides were annealed and ligated into the mammalian expression vector pcDNBA3.1 according to the methods of Gilchrist et al., *J. Biol. Chem.* 274:6610-6616, 1999, the disclosures of which are hereby incorporated by reference.

Figure 14:
FIG. 14 is an agarose gel of PCR products showing transcription of peptide minigene RNA in transfected cells. Lane 1 contains size markers, lane 2 contains PCR products from cells transfected with pcDNA-GiR, lane 3 contains PCR products from cells transfected with pcDNA-Gi, and lane 4 contains PCR products from cells transfected with pcDNA3.1, the empty vector.

Human embryonic kidney (HEK) 293 cells were transfected using a standard calcium phosphate procedure according to the methods of Sambrook et al., Molecular Cloning: A Laboratory Manual, Cold Spring Harbor Laboratory Press, New York, vol. 1-3 (1989), the disclosures of which are hereby incorporated by reference. To confirm the transcription of minigene constructs in transfected cells, total RNA was isolated from the cells 48 hours post transfection with pcDNA-Gαi or pcDNA-GαiR using methods known in the art. Reverse transcriptase PCR was used to make cDNA and PCR analysis was performed using the cDNA as template with primers specific for the relevant Gα carboxyl terminal peptide insert (forward: 5'-ATCCGC-CGCCACCATGGGA (SEQ ID NO:272); reverse: 5'-GC-GAAAGGAGCGGGGCGCTA (SEQ ID NO:273)). These primers for the Gα minigenes amplify a 434 bp fragment only if the inserted peptide-encoding oligonucleotides are present; no band is observed in cells transfected with the empty pcDNA3.1 vector. The PCR products were separated on 1.5% agarose gels. The presence of a single 434 bp band indicated that Gα carboxyl terminus peptide minigene RNA had been transcribed. See FIG. 14. Control experiments were done using a T7 forward primer with the vector reverse primer to verify the presence of the pcDNA3.1 vector, and G3DPH primers (Clonetech) to approximate the amount of total RNA.

To verify that the peptide was being produced in the transfected cells, the cells were lysed and homogenized 48 hours post transfection according to known methods. Cytosolic extracts were analyzed by gradient reversed phase HPLC as follows: 100 μL of cytosolic fraction extract was loaded onto a C4 column (Vydac) equilibrated with 0.1% TFA in ddH$_2$O. The peptide was eluted using 0.1% TFA in an acetonitrile gradient which increased from 0-60% over 45 minutes. Peaks were collected, lyophilized, and analyzed using ion mass spray analysis (University of Illinois-Urbana Champagne). Mass spectrometry analysis for peak 1 from Gαi$_{1/2}$ peptide vector (pcDNA-Gαi) transfected cells, and from cells transfected with pcDNA-GαiR indicated that a 1450 Dalton peptide (the expected molecular weight for both 13 amino acid peptide sequences) was present in each cytosolic extract. The minigene-encoded peptides were the major peptides found in the cytosol, strongly indicating that the vectors produced the appropriate peptide sequences in large amounts.

Example 25

Interfacial G Protein Peptide Inhibition of Thrombin-Mediated Inositol Phosphate Accumulation HMEC were seeded onto 6-well plates 24 hours before transfection at 1×10$^5$ well. Cells were transiently transfected with pcDNA3.1, pcDNA-Gαi, pcDNA-GαiR, or pcDNA-Gq as described in Example 24. After 24 hours, cells were incubated in 2 mL culture medium containing 4 μCi/mL [$^3$H]-myoinositol to obtain steady-state labeling of cellular inositol lipids. Transiently transfected cells were assayed for inositol phosphate (IP) accumulation 48 hours after transfection. Two hours prior to stimulation with α-thrombin, cells were washed, and medium replaced with medium containing 5 mM LiCl. Cells were stimulated with 10 nM α-thrombin for 10 minutes. Inositol phosphate (IP) formation was stopped by aspiration of the medium and addition of ice-cold methanol (final concentration 5%).

Figure 15:
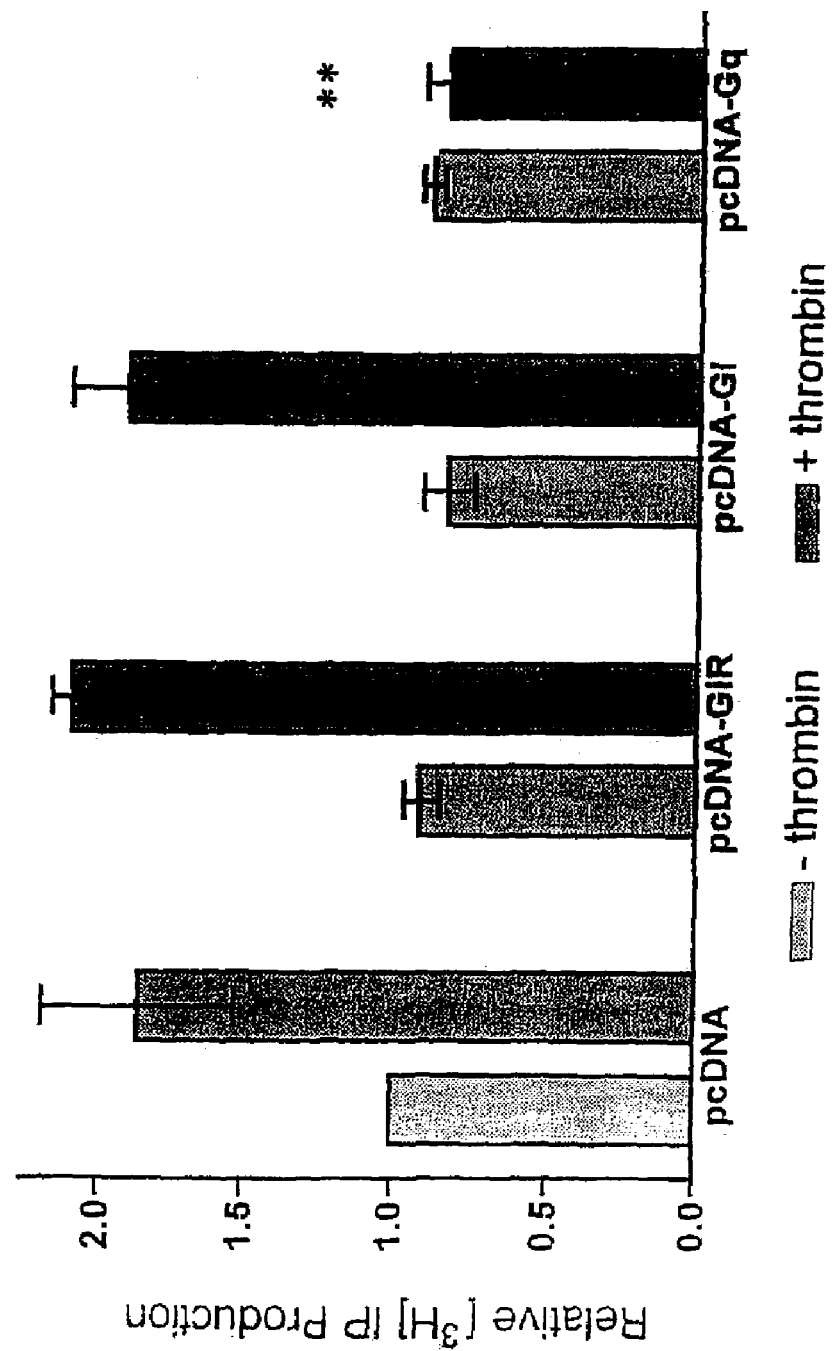
FIG. 15 is a bar graph showing the relative [$^3$H] inositol phosphate production after thrombin stimulation normalized against the basal value.

Perchloric acid-lysed cells were centrifuged at 2500 rpm, 4° C. for 5 min. The supernatant containing IP was eluted through a Poly-Prep chromatography column (Bio-Rad) containing 1.6 ml anion exchange resin (DOWEX AG1-X8, formate form, 200-400 mesh). The perchloric acid-precipitated pellets (containing phosphatidylinositols and lipids) were resuspended in 1 ml chloroform-methanol-10 M HCl (200:100:1, v/v/v). These suspensions were mixed with 350 μL HCl and 350 μL chloroform and sedimented for 5 min at 2500 rpm to separate the phases. The lower, hydrophobic phase was recovered and dried in counting vials to determine the amount of radioactivity in total phosphatidylinositols. The relative amount of [$^3$H]-IP generated was calculated as follows: ([$^3$H]-IP (cpm)/[$^3$H]-IP (cpm)+[$^3$H]-inositol (cpm)). Each value was normalized using the basal value (no thrombin stimulation) obtained in pcDNA transfected cells. See FIG. 15. The results presented are the normalized mean±SEM of at least 3 independent experiments performed in triplicate. The ** symbol indicates $p<0.005$. Results indicate that addition of thrombin increased IP production in control cells (pcDNA, pcDNA-GiR). Cells transfected with PcDNA-Gq had no thrombin-mediated IP production increase, while cells transfected with pcDNA-Gi had a normal response. This indicates that transfection of the Gq C-terminal minigene vector into HMEC with subsequent expression of the Gq C-terminal peptide can inhibit thrombin-mediated increases in IP.

Example 26

Interfacial G Protein Peptide Inhibition of Thrombin-Induced P1 Hydrolysis and Intracellular Ca$^{++}$ Rise To determine whether expression of the Gαq C-terminal minigene vector could affect intracellular [Ca$^{++}$]$_i$ levels, HMEC were transfected with empty vector (pcDNA) or with pcDNA-Gαi, pcDNA-Gαq, or pcDNA-GαiR minigene DNA (1 µg), which encode high affinity peptides identified for their ability to bind the receptors. Transfected cells were seeded at a low confluency on coverslips in a 24-well plate 48 hours post transfection. The cells were allowed to adhere for two hours. The medium was aspirated and each coverslip was incubated with 10 µM Oregon Green 488 BAPTA-1 acetoxymethyl ester (a calcium-sensitive dye) and 0.1% (v/v) Pluronic F-127 and allowed to incubate for 20-30 minutes at 37° C., then rinsed twice with wash buffer. Basal conditions were established before addition of thrombin (~70 nM) in $Ca^{++}$ buffer. Recordings were made every 10 seconds and continued for 170 seconds after stimulation with thrombin. Images were quantitated using NIH Image. Data from at least 70 individually recorded cells were used to calculate the changes in fluorescence (y-axis). See FIG. 16A, which presents fluorescence in ($[Ca^{++}]_i$ level) increase 30 seconds after thrombin addition. Each bar in FIG. 16A represents the mean (($F_S-F_B/F_B-1$)±SEM of over 70 individually recorded cells. The ** symbol indicates p<0.005. FIG. 16B shows the kinetics of $[Ca^{++}]_i$; fluorescence changes after cell stimulation with thrombin. Data presented are the mean (($F_S-F_B/F_B-1$)±SEM at each recording point for cells transfected with cDNA for the empty vector (pcDNA) or the Gq C-terminal minigene vector (pcDNA-Gαq). The arrow indicates the time thrombin was added. Each time point represents over 100 individually recorded cells.

Figure 16:
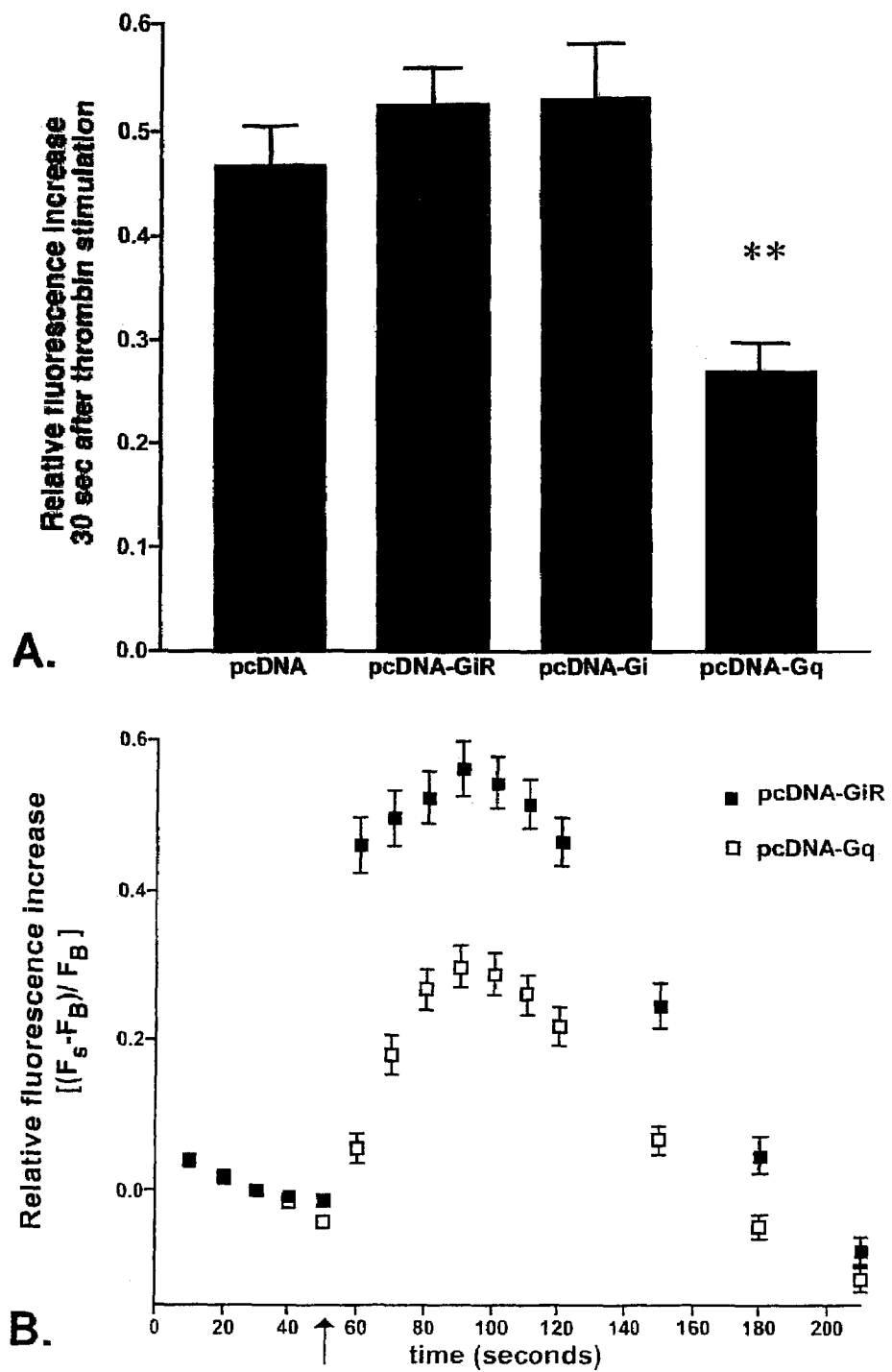
FIG. 16 presents data showing inhibition of a GPCR mediated increase in intracellular calcium concentration in the presence or absence of a minigene vector encoding the identified high affinity peptide.
Figure 17:
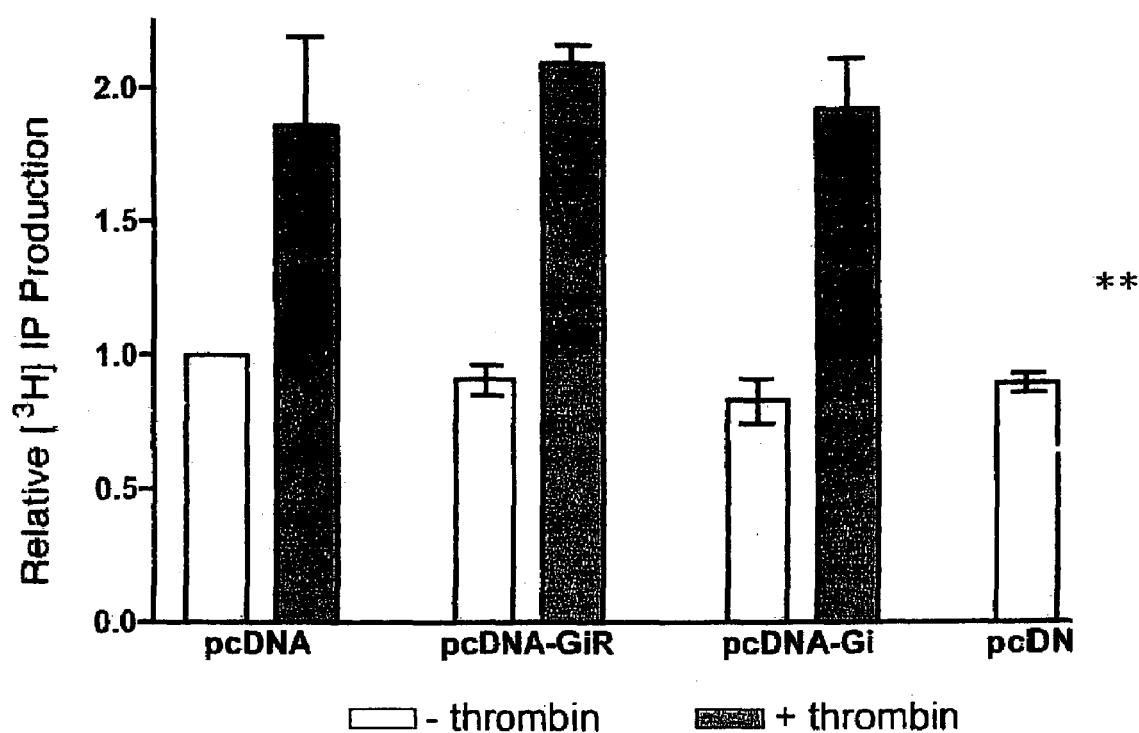
FIG. 17 presents data showing inhibition of a GPCR-mediated phosphoinositol (PI) hydrolysis in the presence or absence of a minigene vector encoding the identified high affinity peptide.

As shown in FIG. 16, following cell activation by addition of thrombin there was a transient increase in intracellular $[Ca^{++}]_i$ levels. Thirty seconds after the addition of thrombin, cells transfected with pcDNA-Gαq had a calcium response that was 44% decreased as compared to cells transfected with pcDNA (FIG. 16A). pcDNA-Gαq transfected cells had a 45% decrease compared to those transfected with pcDNA when all time points measured after thrombin stimulation are averaged (FIG. 16B). This decrease appears to be specific as cells transfected with pcDNA-Gαi or pcDNA-GαiR did not have any effect on thrombin stimulated $[Ca^{++}]_i$ levels. Thus, cells expressing the Gαq C-terminal peptide appear to be inhibited in their ability to stimulate $[Ca^{++}]_i$ levels following activation with thrombin, indicating a specific block of this downstream mediator by expression of Gαq.

pcDNA, pcDNA-GiR, pcDNA-Gi, pcDNA-Gq, or pcDNA-Gs minigene constructs were transfected into HMEC and used to assay inositol phosphate (IP) accumulation. After 24 hours, cells were reseeded onto 24-well plates and labeled with [³H]-myoinositol (2 µCi/ml). After 48 hours, cells were rinsed, and incubated with or without thrombin (10 nM) for 10 minutes. Total IP accumulation was assayed as described above using Dowex™ columns to separate [³H]IP. The relative amount of [³H]IP generated was calculated as follows: ([³H]IP (cpm)/[³H]IP (cpm)+[³H] inositol (cpm)). Each value was normalized by the basal value (no thrombin stimulation) obtained in pcDNA transfected cells. See FIG. 17. The results presented are the normalized mean±SEM of at least three independent experiments performed in triplicate. The ** symbol indicates p<0.005.

Example 27

Figure 18:
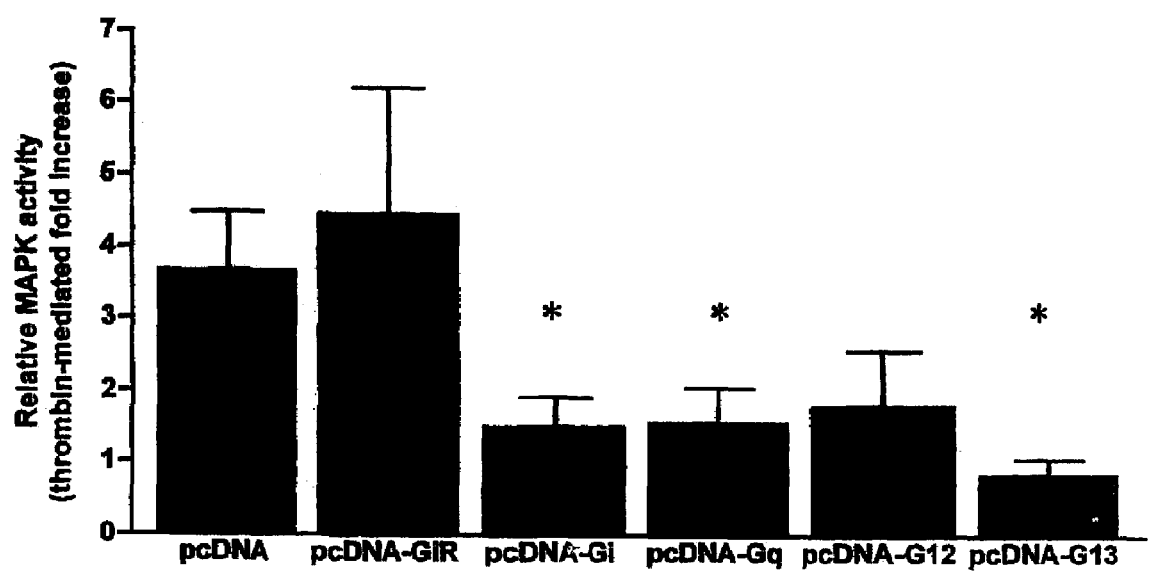
FIG. 18 is a bar graph indicating relative GPCR-mediated increase of MAPK activity in the presence or absence of a minigene vector encoding the identified high affinity peptide in cells expressing GPCR-binding peptides.

Prevention of Thrombin-Induced MAPK Activity by GPCR-binding C-terminal Peptides Hemagglutanin (HA)-MAPK (1×10⁵/mL was co-transfected into HMEC with the pcDNA, pcDNA-Gαi, pcDNA-Gαq or pcDNA-GαiR minigene constructs using the methods described in Example 24. After 30 hours, cells were serum-starved for 18 hours and then treated with 10 nM thrombin for 20 minutes. Cells were then lysed with RIPA buffer (50 mM Tris, pH 7.5, 150 mM NaCl, 2 mM EDTA, 1% Triton X-100, 0.5% deoxycholate, 0.1% SDS, 10% glycerol, 10 µg/mL aprotinin and 10 µg/mL leupeptin) and HA-MAPK protein immunoprecipitated using 12CA5 antibody (Roche Molecular Biochemicals; Indianapolis, Ind.) (one hour, 4° C.) and Protein A sepharose beads (three hours, 4° C.). Immune complexes were washed three times in RIPA buffer. Kinase activity in the immunoprecipitates was measured using maltose binding protein (MBP) substrate and a kinase assay kit (Upstate Biotechnology, Inc., Lake Placid, N.Y.). MAPK activity (nmol/min/mg) was obtained for each, and the relative increase of MAPK activity (thrombin-mediated fold increase) was calculated as follows: (stimulated activity (nmol/min/mg)–basal activity (nmol/min/mg))/basal activity (nmol/min/mg). Results are presented as the mean±SEM of at least three independent experiments in FIG. 18. A * symbol indicates p<0.05.

Addition of 10 mmol thrombin resulted in a 3.66 fold increase in HA-MAPK activity in cells transfected with the pcDNA control vector. Similarly, cells transfected with pcDNA-GiR had an essentially equivalent increase in thrombin mediated MAPK activity with (4.46 fold increase). However, endothelial cells transfected with a minigene construct encoding the Gαi, Gαq, Gα12 or Gα13 GPCR binding peptides showed a significant decrease in thrombin-mediated HA-MAPK activity (59%, 57%, 50% and 77%, respectively) compared to cells transfected with pcDNA.

Example 28

Reduction of Thrombin-Induced Transendothelial Electrical Resistance

Figure 19:
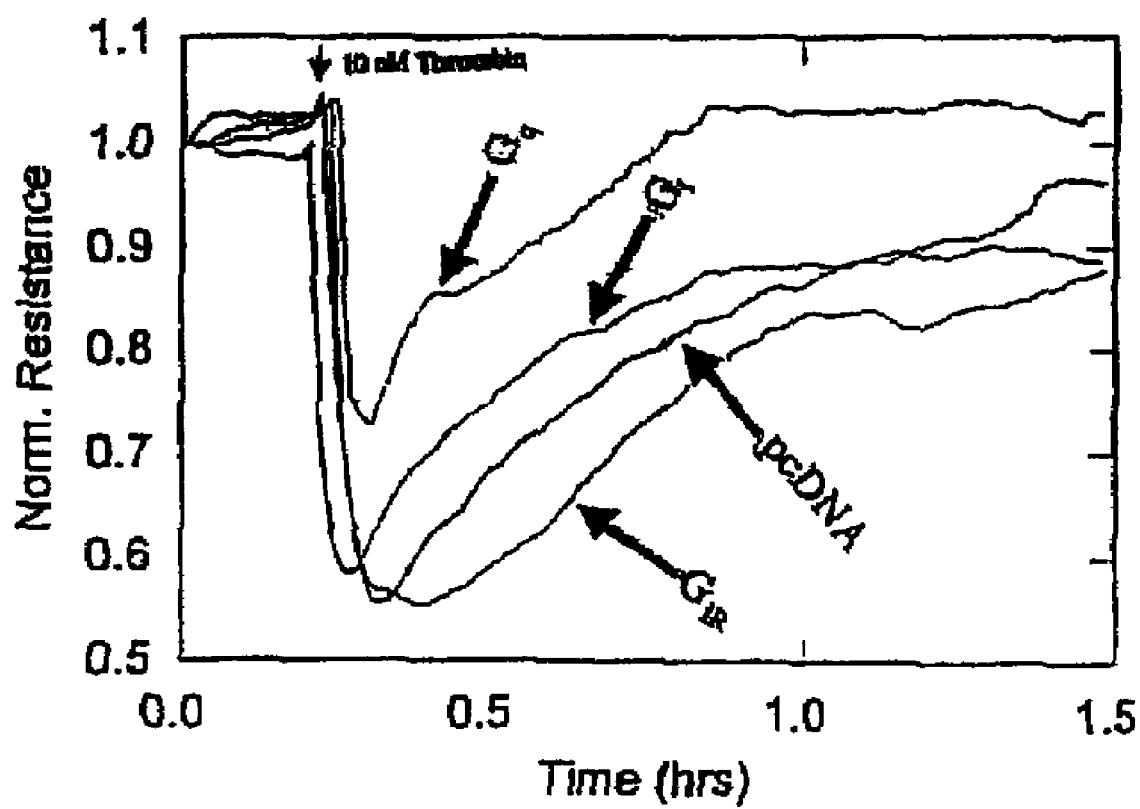
FIG. 19 shows reduction of thrombin-induced transendothelial electrical resistance in cells expressing Gαq, Gαi, GαiR or empty vector.

Transendothelial electrical resistance (TEER) was measured by passing an alternating current (50 µA; 2 pulses every minute) across monolayers of HMEC expressing Gαq, Gαi, GαiR or no minigene construct. Basal TEER did not change significantly with minigene transfection. Upon addition of 10 nM thrombin, however, there was a decrease in the TEER of cells expressing the Gαq minigene compared to non-transfected cells in the presence of 10 nM thrombin. See FIG. 19 (representative of multiple experiments). The decrease in transendothelial electrical resistance in response to thrombin was significantly reduced in endothelial cells transfected with the minigene for the carboxyl terminus of Gαq, while there was no effect in cells transfected with Gαi, GαiR, or empty vector. These results suggested that Gαq is partially responsible for the effects of thrombin on endothelial cell shape changes.

Example 29

Inhibition of Thrombin-Mediated Stress Fiber Formation

HMEC cells were transfected with pcDNA, pcDNA-Gα12 or pcDNA-Gα13 minigene constructs 1 µg each/100 mm dish. As a marker for transfected cells, the pGreenLantern-1 plasmid, containing the gene for green fluorescent protein (GFP) was co-transfected together with minigene constructs. After 48 hours, cells were serum starved for 18 hours and treated with 10 nM thrombin for 20 minutes. After exposure to thrombin, the cells were fixed with 4% paraformaldehyde, permeabilized with 0.1% Triton X-100 and stained for F-actin with 1 mM rhodamine-phalloidin for 30 minutes. Cells were extensively washed, mounted using Vectashield™ antifade mounting medium (Vector Laboratories, Inc.). Cells were observed with an inverted microscope (Diaphot 200, Nikon, Inc.) equipped for both differential interference contrast microscopy and epifluorescence observation using a 60× oil-immersion objective. Fluorescence and DIC images were recorded for each cell field with a cooled, integrating CCD array camera (Imagepoint, Photometrix, Ltd.) connected to the microscope. See FIG. 20 for fluorescence images showing inhibition of thrombin-mediated stress fiber formation by Gα12 and Gα13 peptides.

Figure 20:
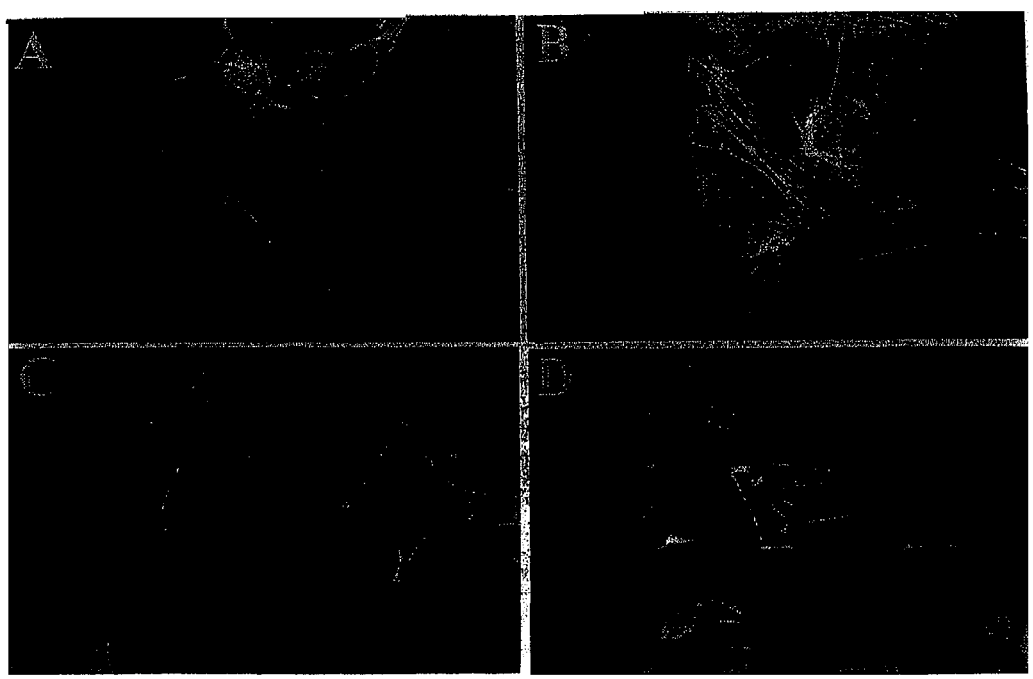
FIG. 20 is a series of photographs of cells stained for F-actin, showing the inhibition of stress fiber formation after exposure to thrombin in cells expressing pcDNA-G12 or pcDNA-G13 minigene construct.

Serum-starved cells transfected with pcDNA exhibited a thin cortical F-actin rim at their margins, and contained few stress fibers (FIG. 20, panel A). Those present were inconspicuous and in apparently random orientation. For HMEC transfected with pcDNA after a 20-minute exposure to thrombin actin had reorganized into prominent stress fibers, typically arranged in a parallel pattern along the longitudinal axis of the cell (FIG. 20, panel B). A very different pattern was observed for cells transfected with pcDNA-Gα12 (FIG. 20, panel C) or pcDNA-Gα13 (FIG. 20, panel D) minigenes after exposure to thrombin. In both pcDNA-Gα12 and pcDNA-Gα13 transfected cells, thrombin stimulation did not result in the appearance of stress fibers. In cells transfected with pcDNA-Gα13, the peripheral actin rim appears thicker and more linear, providing a clear outline of cell-cell junctions. Thus, in agreement with earlier reports, thrombin induced rapid stress fiber formation in endothelial cells. Transfection of either pcDNA-Gα12 or pcDNA-Gα13 minigenes resulted in cells that no longer showed thrombin-induced stress fiber formation. Given that stress fiber formation is dependent on the small GTPase Rho, these results concur with other findings that Gα12 and Gα13 are intimately linked to Rho signaling and demonstrates the ability of GPCR binding peptides to specifically block this G protein pathway when expressed intracellularly.

Example 30

Inhibition of G Protein Activity by GPCR Binding Peptides in Single Intact Cells Human embryonic kidney (HEK) 293 cells, which stably express the $M_2$ mACR (~400 fmol receptor/mg protein), were grown in DMEM (Gibco) supplemented with 10% fetal bovine serum (Gibco), streptomycin/penicillin (100 U each; Gibco) and G418 (500 mg/L; Gibco). Cells were grown under 10% $CO_2$ at 37° C. In all transfections for electrophysiological studies, the CD8 reporter gene system was used to visualize transfected cells using Dynabeads™ coated with anti-CD8-antibodies (Dynal). The following amounts of cDNA were used to transfect the cells: pC1-GIRK1 (rat)–1 µg; πH3-CD*(human)–1 µg; pcDNA3.1, pcDNA-Gαi, pcDNA-GαiR, pcDNA-Gαq, or pcDNA-Gαs–4 µg. Thus, typically the total amount of cDNA used for transfecting one 10 cm disk was 7 µg. The cDNAs for GIRK1 and GIRK4 were gifts from F. Lesage and M. Lazdunski (Nice, France). A standard calcium phosphate procedure was used for transient transfection of HEK cells according to the methods of Schenborn et al., *Meth. Mol. Biol.* 130:135-145, 2000. All assays were performed 48-72 hours post transfection.

Whole cell currents were recorded from stably $M_2$ mAChR-expressing HEK 293 cells that had been transiently transfected with cDNA for GIRK1, GIRK4 and either pcDNA-Gαi, pcDNA-Gαs, or pcDNA-Gαq. For the measurement of inwardly rectifying $K^+$ currents, whole cell currents were recorded using an extracellular solution contained 120 mM NaCl; 20 mM KCl; 2 mM $CaCl_2$; 1 mM $MgCl_2$; and 10 mM HEPES-NaOH, pH 7.4. The solution for filling the patch pipettes was composed of 100 mM potassium glutamate; 40 mM KCl; 5 mM MgATP; 10 mM HEPES-KOH, pH 7.4; 5 mM NaCl; 2 mM EGTA; 1 mM $MgCl_2$; and 0.01 mM GTP. Membrane currents were recorded under voltage clamp, using conventional whole cell patch techniques. See Bunemann et al., *J. Physiol.* 489:701-777, 1995 and Bunemann et al., *J. Physiol.* 482: 81-89, 1995, the disclosures of which are hereby incorporated by reference. To minimize variations due to different transfections or culture conditions, control experiments (transfection with pcDNA-GαiR) were done in parallel. Patch-pipettes were fabricated from borosilicate glass capillaries, (GF-150-10, Warner Instrument Corp.) using a horizontal puller (P-95 Fleming & Poulsen). The DC resistance of the filled pipettes ranged from 3-6 MΩ.

Membrane currents were recorded using a patch-clamp amplifier (Axopatch 200, Axon Instruments). Signals are analog-filtered using a lowpass Bessel filter (1-3 kHz corner frequency). Data were digitally stored using an IBM compatible PC equipped with a hardware/software package (ISO2 by MFK, Frankfurt/Main, Germany) for voltage control, data acquisition and data evaluation. To measure $K^+$ currents in the inward direction, the potassium equilibrium potential was set to about −50 mV and the holding potential was −90 mV. Agonist-induced currents were evoked by application of acetylcholine (ACh; 1 µM) using a solenoid operated superfusion device which allowed for solution exchange within 300 mseconds. Linear voltage ramps (from −120 mV to +60 mV within 500 mseconds) were applied every 10 seconds. By subtracting non-agonist dependent currents, the current voltage properties of the agonist induced currents could be resolved. To exclude experiments in which currents were recorded from cells that may not have expressed the functional channel, only those cells that exhibited a basal non-agonist dependent $Ba^{++}$ (200 µM) sensitive inwardly rectifying current were used for analysis. For analysis of the data, the maximal current density (peak amplitude) of ACh-induced inwardly rectifying $K^+$ currents was measured at −80 mV and compared.

Figure 21:
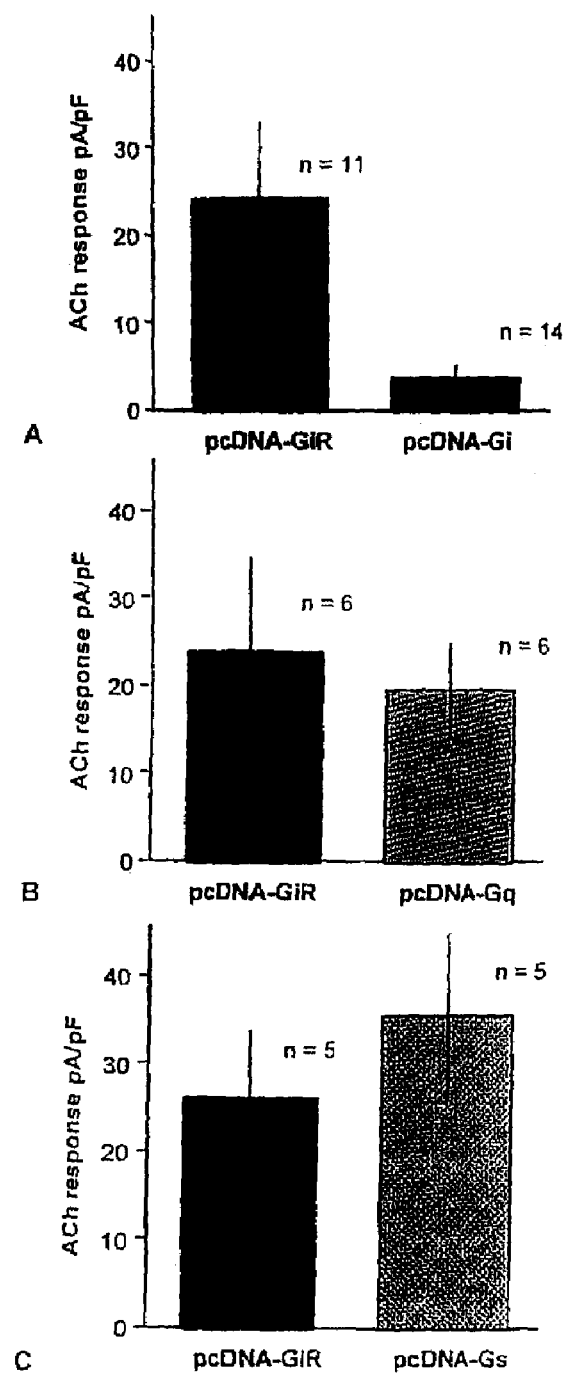
FIG. 21 is a bar graph showing acetylcholine (Ach) response (pA/pF) for HEK 293 cells transiently transfected with GIRK1/GIRK4 and the indicated minigene construct.

Superfusion of HEK 293 cells transiently transfected with GIRK1/GIRK4 and either pcDNA-Gi or pcDNA-GiR DNA with 1 µM ACh revealed that cells transfected with pcDNA-$Gα_i$ DNA have a dramatically impaired response to the $M_2$ mAChR agonist. See FIG. 21, which summarizes data showing the maximum amplitude of ACh evoked currents for the different transfection conditions (cells transfected with GIRK1/GIRK4 and pcDNA-Gi or cells transfected with GIRK1/GIRK4 and pcDNA-GiR). The pcDNA-Gi minigene vector results in high intracellular expression of the Gαi peptide, leading to diminished ability of the receptor to signal the heterotrimeric Gαi.

The maximum current evoked by ACh was 3.7+/−1.5 pA/pF (n=14) in cells transfected with pcDNA-Gi, compared to 24.1+/−8.8 pA/pF (n=11) in cells transfected with pcDNA-GiR. This indicates that the Gαi minigene construct completely blocked the agonist mediated $M_2$ mAChR GIRK1/GIRK4 response while the control minigene construct (pcDNA-GiR) had no effect. Compare FIG. 21A to FIGS. 21B and 21C. Cells transfected with minigene constructs encoding Gα carboxyl termini for Gαq or Gαs pcDNA-Gαq or pcDNA-Gαs were not significantly different than those of cells transfected with the control vectors. These findings confirm the specificity of the inhibition of M$_2$ mAChR-activated G protein-coupled inwardly rectifying K$^+$ current responses by expression of the Gαi minigene.

Example 31

Selective G Protein Signaling Inhibition in Human Microvascular Endothelial Cells Different measures of G-protein signaling final actions were assayed in human microvascular endothelial cells (HMEC) which natively express the thrombin receptor, PAR1. The cells were seeded onto 6-well plates at 1×10$^5$ cells/well and transiently transfected after 24 hours with minigene constructs containing Gα carboxyl terminal peptides (pcDNA, pcDNA-Gαi, or pcDNA-GαiR; 1 µg per well) using Effectene (Qiagen) according to the manufacturer's protocol. After 24 hours, the cells were labeled with 3 µCi/ml [$^3$H]-adenine for 30 minutes at 37° C. After another 24 hours, the cells were washed with serum-free medium containing 1 mM isobutyl-methyl xanthine. To stimulate cAMP accumulation, cells were treated with 1 µM isoproterenol for 30 minutes at 37° C. To see the inhibitory effects of thrombin on cAMP accumulation, cells were pretreated with thrombin (50 nM) for 15 minutes prior to addition of isoproterenol. The reactions were terminated by aspiration of media followed by addition of ice-cold 5% trichloroacetic acid.

Figure 22:
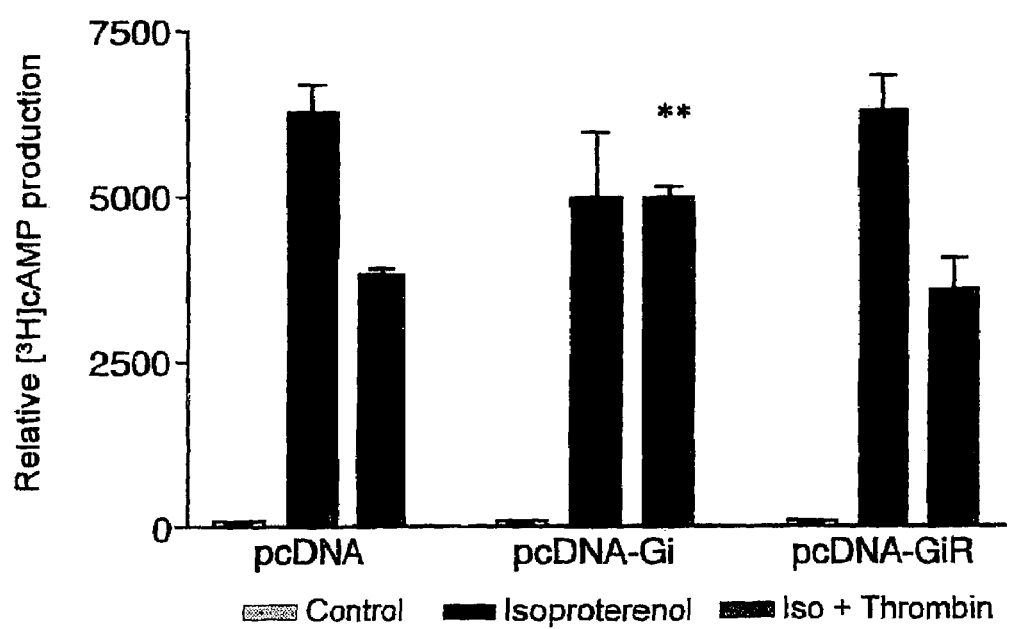
FIG. 22 demonstrates selective G protein mediated adenylyl cyclase inhibition in cells expressing minigene constructs containing Gα carboxyl terminal peptide inserts.

Results are provided in FIG. 22 as (cAMP/cAMP+ATP)× 1000. Three separate experiments were done in duplicate. The ** symbol indicates p<0.005. Basal cAMP levels were essentially equivalent for all conditions tested. Endothelial cells stimulated with isoproterenol to activate β-adrenergic receptors increase their cAMP levels through the Gs pathway. Cells transfected with pcDNA, pcDNA-Gαi, or pcDNA-GαiR showed little difference with 82-, 64-, and 77-fold increases in isoproterenol-mediated cAMP accumulation, respectively. When the endothelial cells were pre-incubated with thrombin prior to addition of isoproterenol, a decrease in cAMP levels was observed due to thrombin activation of the Gi pathway. Endothelial cells transfected with pcDNA and pre-incubated with thrombin showed a 39% decrease in cAMP level over cells stimulated with only isoproterenol. Similarly, cells transfected with pcDNA-GαiR and pre-incubated with thrombin showed had a 43% decrease over cells stimulated with only isoproterenol. However, cells transfected with pcDNA-Gαi and pre-incubated with thrombin had only a 0.1% decrease in cAMP levels as compared to cells stimulated with only isoproterenol. Thus, cells expressing the Gαi C-terminal peptide appear to be unable to inhibit adenyl cyclase following activation with thrombin, indicating that thrombin-mediated Gi signaling was specifically blocked by expression of the pcDNA-Gαi minigene.

Example 32

Screening Method to Identify Inverse Agonists

Urea-washed rod outer segment membrane fragments containing rhodopsin receptor are immobilized onto microtiter wells and blocked as described in Example 7. The receptor is light-activated. Labeled native Gαt carboxyl terminal peptide is added to each well and allowed to shake gently for one hour at 4° C. The wells are washed to remove unbound peptide. Crude bacterial lysates (labeled) from a Gαt carboxyl terminal peptide prepared according to the methods described in Example 7 (200 µL) are added to each well and incubated with shaking for one hour at 4° C.

The wells then are washed to remove unbound label. The supernatants or well-bound labels are quantitated by ELISA to detect dissociation of labeled native peptide from the receptor after incubation with library peptides compared to control wells incubated in the absence of library peptides.

Example 33

Small Molecule Library Screening Method

Small molecule libraries are screened for inhibition of GPCR-mediated G protein signaling as follows. PAR1 thrombin receptor prepared from insect cells according to Example 3 are immobilized onto microtiter wells, blocked and washed. A small molecule library purchased from Chem Div (San Diego, Calif.) are added simultaneously with MBP-peptide fusion protein (0.1-1000 nM) in a 96- or 384-well plate and allowed to shake for one hour at 4° C. Initial screens are performed with the small molecules at about 5-5000 nM. The wells are washed four times in cold PBS containing 0.05% Tween 20™ and 1 mM maltose. The amount of maltose binding protein adhering to the wells is quantitated with anti-MBP antibodies as described in Example 17, versus control wells incubated without library compounds.

Example 34

Identification of Very High Affinity Activated Rhodopsin-Binding Gt-Based Peptides A combinatorial peptide library based on the C-terminal sequence of Gt was constructed by introducing all possible mutations at each position, but with an overall bias toward the Gαt sequence with a K341R change and panned for high-affinity binding. See Martin et al., *J. Biol. Chem.* 271:361-366, 1996; Gilchrist et al., *Methods Enzymol.* 315: 388-404, 2000 the disclosures of which are hereby incorporated by reference, and Examples 7 and 17 for methods used. Specific residues within the C-terminal sequence were highly conserved. Perhaps more interesting is not only the selection against the native amino acid at a given position (R341, the second residue in the peptide shown below) but the apparent selection for a specific amino acid at that location (leucine). See Table XX. Table XXI shows amino acid sequences obtained from screening dark-adapted bovine rhodopsin with the same combinatorial peptide library based on the C-terminal sequence of Gt. As observed with Gt, specific residues within the carboxyl terminal sequence were conserved and specific residues were selected against. Notably, at identical positions there are extreme differences between the selection of light-activated and dark-adapted rhodopsin (i.e., position C347) indicating that upon activation the receptor undergoes a conformational change unmasking new sites which the G protein can interact.

TABLE XX

Alignment of the Highest-Affinity Amino Acid Sequences Screened based on the C-Terminal Sequence of Gt with Light-Activated Rhodopsin.

| Gt Library | xxxx |   |   |   |   |   |   |   |   |   |   |   | SEQ ID NO: 124 |
|---|---|---|---|---|---|---|---|---|---|---|---|---|---|
| 3 | vgrs |   | L |   |   |   |   |   |   |   |   | L | 266 |
| 7 | tskp | M | L | D |   |   |   |   |   |   |   |   | 213 |
| 8 | fvpd | L | L |   |   |   | R |   |   |   | M | F | 125 |
| 9 | trfa | L | Q | Q | V |   |   |   |   |   |   | L | 267 |
| 10 | aldy |   | C |   |   |   |   |   |   |   |   |   | 215 |
| 17 | lnsd |   | L | Q |   |   |   |   |   |   |   |   | 212 |
| 18 | kqrn | M | L |   |   |   |   |   |   |   |   |   | 128 |
| 23 | tggr | V | L |   | D |   |   | K | S |   |   |   | 129 |
| 24 | kgqa | M | L | K |   |   |   |   |   |   | M |   | 130 |

TABLE XXI

Alignment of Amino Acid Sequences Screened based on the C-Terminal Sequence of Gt with Dark-Adapted Rhodopsin.

| Gt Library | xxxx |   |   |   |   |   |   |   |   |   |   |   | SEQ ID NO: 124 |
|---|---|---|---|---|---|---|---|---|---|---|---|---|---|
| 2 | lmec |   |   | K | W |   |   | L | A |   |   |   | 143 |
| 3 | dfwh | V |   | D |   |   |   | N |   | F |   |   | 144 |
| 7 | pgmh |   | G |   | Q | I | E |   |   |   | P |   | 145 |
| 17 | lrht |   |   | N |   |   |   | R | Y |   | M |   | 146 |
| 21 | lkaw |   |   |   |   |   |   | L |   |   |   | V | 147 |
| 26 | glfk |   |   |   | F |   | Y | L |   |   |   | W | 148 |
| 33/37 | rklt | S | L |   | I |   |   | W |   |   |   |   | 149 |
| 31 | rpkl |   | G | T |   | G | W |   |   |   |   |   | 150 |

In all the high affinity sequences selected for binding to the light adapted rhodopsin, position 341, which normally is a positively charged residue was changed to a neutral one. There is an obvious selection for a specific amino acid change from R to L. Peptides synthesized with this single change were assayed for high affinity binding, and the results are shown in Table XX. There was not a selection for a neutral amino acid at position 341 in peptides selected for binding to dark-adapted rhodopsin. See Table XXI. Arg is found 75% of the time. For peptides selected for light-activated rhodopsin, Leu344, Cys347, and Gly348 were found to be invariant, and hydrophobic residues were always located at positions 340, 349 and 350, indicating the critical nature of these residues. This differs considerably from the peptides selected for binding to dark-adapted rhodopsin, which did not show any invariant positions. Most striking is the apparent selection against the Cys347 position. Cys347 and Gly 348 both are part of a type II' β-turn which is required for MII stabilization. This suggests that a site on rhodopsin which is required to bind the Cys 347 of Gt is unmasked only after the receptor has received a photon of light and formed MII. See Gilchrist et al., *Methods Enzymol.* 15:388, 2000. Other works indicate that the critical nature of Cys347 for binding light-activated rhodopsin is due to its hydrophobicity. Aris et al., *J. Biol. Chem.* 276:2333, 2001. Replacement of Cys 347 with a hydrophobic amino acid (Cys347Met, Cys347Val and Cys347Abu) (Abu=2-aminobutyric acid) stabilizes MII to the same extent and with similar potency as the parent peptide. The apparent selection of Lys at 347 in the dark-adapted rhodopsin peptides clearly indicates that binding of the Gα peptide to dark-adapted rhodopsin is very different from light-activated rhodopsin. These results show that the site on rhodopsin recognized by the C-terminal tail of Gt differs depending on whether the receptor is dark-adapted or light-activated. This implies that high affinity peptides selected for binding to light-activated rhodopsin only bind the activated state of the receptor and not dark-adapted receptor.

Example 35

Figure 23:
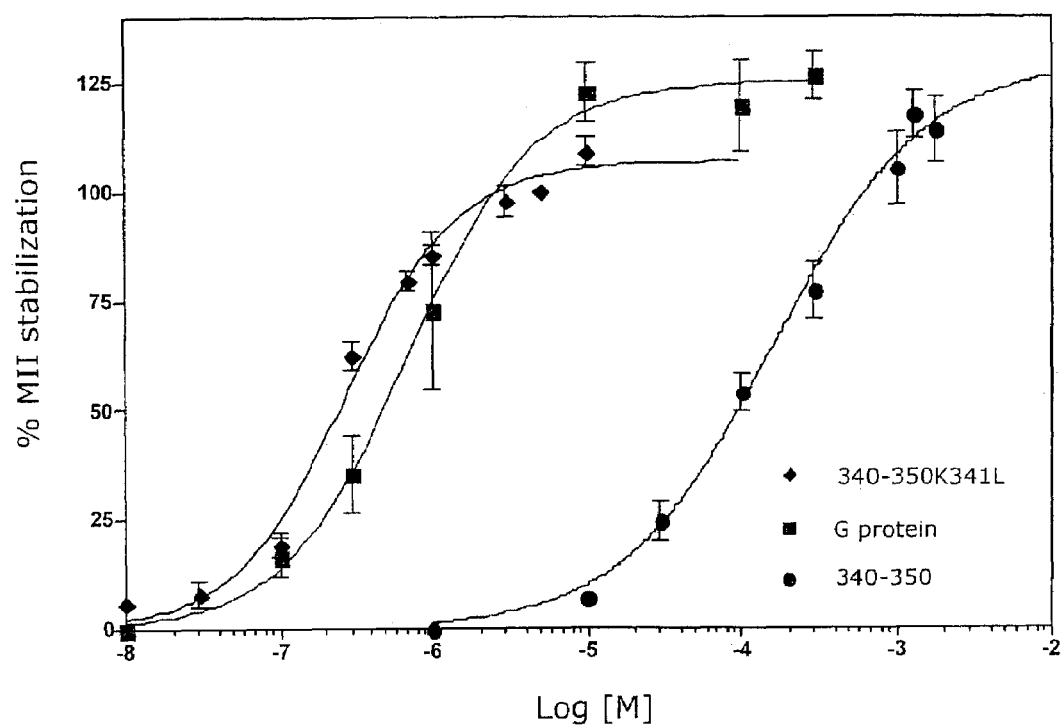
FIG. 23 presents dose-response curves of MII stabilization by αt340350, mutant αt340-350K341L and heterotrimeric Gt.

Assays for Determining Peptide, Peptide-Fusion Protein or Small Molecule Affinities for Metarhodopsin II For the "extra MII" assay, EDTA-washed rhodopsin (Example 5; 5 µM) is incubated in a 50 mM HEPES buffer, pH 8.2, with 100 mM NaCl, 1 mM $MgCl_2$, and 1 mM DTT at 5.3° C., in the absence or presence of varying concentrations of Gt340-350 analogs or Gt. The sample is maintained at 5.4° C. using a water-jacketed and thermostated circulator cuvette holder in an SLM Aminco DW2000 spectrophotometer at 390 and 440 nm. A flash of light bleaching 10% of the rhodopsin is presented and after a 1 min incubation, a second spectrum is measured and the difference in spectrum calculated. "Extra" MII is calculated as the difference between the absorbance at 390 and 440. Dose response curves of MII stabilization by αt340350 (λ), mutant α340-350K341L(v), and heterotrimeric Gt (v) were analyzed by non-linear regression using the program GraphPad PRISM and are shown in FIG. 23.

For the MII decay assay, the absorbance spectra of EDTA-washed ROS (10 µM) is measured in an SLM Aminco DW2000 spectrophotometer in 10 mM $K_2PO_4$, pH 6.5 containing 0.1 M KCl, 0.1 mM EDTA, 1 mM DTT, in the presence of peptide, fusion protein expressing high affinity peptide or small molecule. The spectra are measured in the dark, then completely bleached in room light. The spectra of the bleached sample is measured at intervals of 30 minutes over a 6 hour period.

Example 36

Analysis of Data from Small Molecule Library Screen

Competition ELISA assays were employed to screen a small molecule library (a 10,000 compound library representative of ChemDiv's Diverse Collection of drug-like molecules) for compounds that bind activated rhodopsin and increase/decrease the binding of MBP-8 high affinity peptide fusion protein. MBP 8 was selected based on its mid-range affinity. The screen may be repeated using an MBP which displays higher affinity and ability to stabilize MII (i.e., MBP 18; Table XIX). These types of screens may be used with libraries of any size, therefore it is possible to increase the size of the compound library by 10 fold or greater and continue screening for small molecule hits in a similar manner.

A software program that displays results of screening as a colorometric readout with a unique color coding that represents the amount of inhibition or stimulation of bound light-activated rhodopsin-bound peptide fusion protein is advantageous and preferred. Two representative 96-well plates in which light-activated-rhodopsin-bound MBP-8 high-affinity peptide fusion proteins were assayed for competitive binding by 80 different compounds. Experiments were done in duplicate, and the results of the two separate plates averaged.

Figure 24:
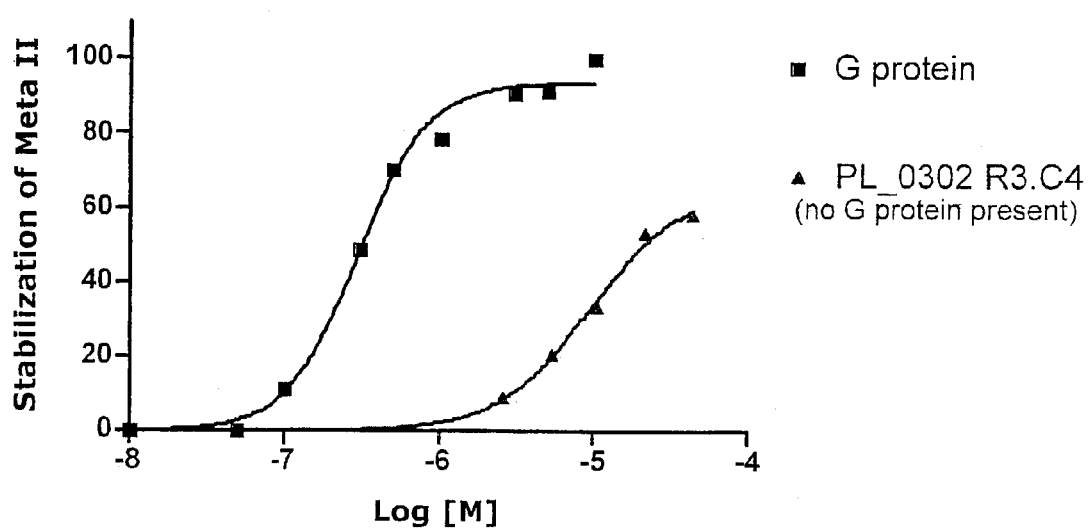
FIG. 24 shows stabilization of MII by small molecule PL_0302R3C4.

Dose response curves of MII (FIG. 24) indicate that both PL_0302 R3.C4 (σ), and heterotrimeric Gt (v) stabilize the active form of rhodopsin. EDTA-washed rhodopsin (5 μM) was incubated in a 50 mM HEPES buffer, pH 8.2, with 100 mM NaCl, 1 mM $MgCl_2$, and 1 mM DTT at 5.3° C., and "extra" MII was measured. For compounds that enhanced MBP-8 binding over 25% using the color coded readout, dose studies were performed to generate $EC_{50}$ curves. Table XXII below provides the calculated $EC_{50}$ for metarhodopsin II stabilization of each compound.

TABLE XXII $EC_{50}$ values for selected small molecules on the binding of MBP-8 to MII.

| Small molecule Name | MW (daltons) | Binding of MBP-8 $EC_{50}$ (μM) |
|---|---|---|
| PL_0568 R1.C5 | 291.2 | 0.96 |
| PL_0551 R8.C1 | 328.5 | 0.95 |
| PL_0894 R3.C7 | 424.9 | 10.1 |
| PL_0302 R3.C4 | 290.27 | 11.9 |
| PL_1012 R2.C1 | 433.5 | 5.12 |

Example 37

Figure 25:
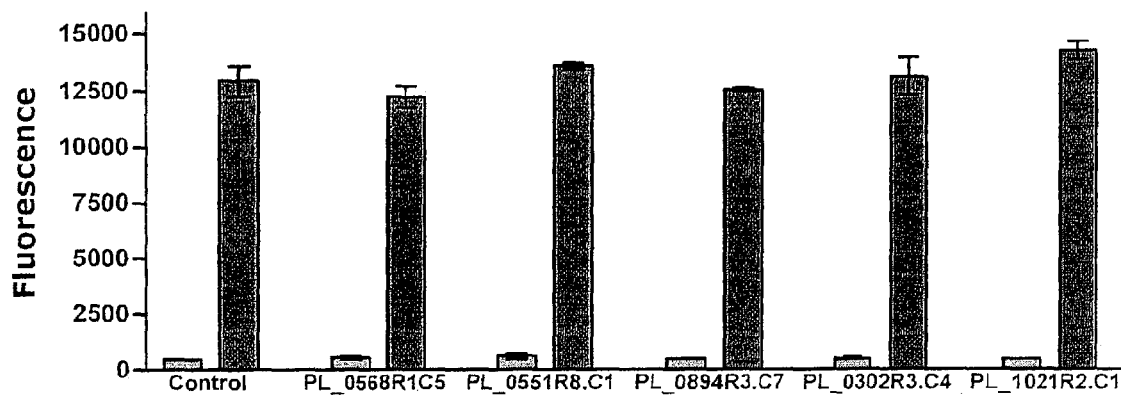
FIG. 25 presents fluorescence data showing super agonists for rhodopsin have no effect on PAR1-stimulated $Ca^{2+}$ transients.

Very High Affinity Agonists for Rhodopsin have no Effect on PAR-1-Stimulated $Ca^{++}$ Transients Small molecules PL_0568 R1.C5, PL_0551 R8.C1, PL-0894 R3.C7, PL_0302 R3.C4, and PL_1012 R2.C1 were tested for their effect on the ability of an unrelated receptor (PAR1) to activate $Ca^{++}$ signaling. Human embryonic kidney cells were cultured in a 96-well format and allowed to adhere for 2 hours. The medium was aspirated and the plate incubated at 37° C. for 30 minutes in 0.5 mL loading buffer (20 mM HEPES (pH 7.4), 130 mM NaCl, 5 mM KCl, 2 mM $CaCl_2$, 1 mM $MgSO_4$, 0.83 mM $Na_2HPO_4$, 0.17 mM $NaH_2PO_4$, 1 mg/ml BSA, 25 mM mannose) containing 0.1% (v/v) Pluronic F127 and 10 μM Oregon Green Bapta-1 acetoxymethyl ester. The small molecules were added to the appropriate wells after 30 minutes and the cells incubated at 37° C. for another 30 minutes. The 96-well plate was tested for calcium concentration using a Flexstation™ system. Basal conditions were established before addition of thrombin (±70 nM). Recordings were made every 5 seconds and continued for >100 seconds after stimulation with thrombin. See FIG. 25.

Example 38

Modulation of MBP-8 Binding to Rhodopsin by Small Molecules

To test the effects of the small molecules in cells, light response experiments were carried out on isolated rods from the dark-adapted retina of a salamander. Single rods were isolated by shredding a small piece of retina. Photoreceptors were mechanically isolated from the dark-adapted retinas and placed in a gravity-fed superfusion chamber on the stage of an inverted microscope. Membrane currents were recorded with a suction electrode as described by Baylor et al., (Baylor et al., *J. Physiol.* (*Lond.*). 288:589-611, 1979; Baylor et al. *J. Physiol.* (*Lond.*). 288:589-611, 1979) in Ringer solution containing 120 mM NaCl, 2.0 mM KCl, 2 mM $NaHCO_3$, 1.6 mM $MgCl_2$, 1.0 mM $CaCl_2$, 10 mM glucose, and 3 mM HEPES, pH 7.6, as described by Rieke and Baylor, *Biophys. J.* 71:2553-2572, 1996. Membrane current collected by the suction electrode was amplified, low-pass filtered at 20 Hz (3 dB point; 8-pole Bessel low-pass), digitized at 100 Hz and stored on a computer for subsequent analysis. Light responses were elicited by 10-msecond flashes of 50-500 nm light. The flash strength was controlled with calibrated neutral density filters. The cell was positioned in the suction electrode to collect as much dark current as possible. Solution changes (by which addition of the small molecule was effected) were achieved with a series of electronically controlled pinch valves (Biochem Valves, Boonton, N.J.) the outlets of which were connected to a common perfusion pipe about 100 μm in diameter. Solution changes with this system were completed in 200-300 mseconds. Solutions were driven by positive pressure through a pair of glass pipes with openings about 50 μm in diameter. The pipes were mounted on a piezoelectric translation stage (Burleigh Instruments, Fishers, N.Y.). Solution changes at the cut end of the outer segment were completed in less than 10 mseconds with this system.

Light stimuli were delivered from a dual beam optical bench. Monochromatic lights were obtained by passing the light from a tungsten-halogen bulb through interference filters with 10 nm nominal bandwidths. Wavelength (520 nm for rods and 440 nm or 620 nm for cones) and intensity of the stimulating light were set with calibrated narrow band interference and neutral density filters, respectively. Salamander L, S, and ultraviolet-sensitive cones have peak sensitivities at 600 nm, 430 nm, and 360 nm (Makino and Dodd, *J. Gen. Physiol.* 108:27-34, 1996) and are readily identified by the relative amplitudes of their responses to 620 nm, 440 nm, and 380 nm lights. After identification, S cones were stimulated with 440 nm light and L cones were stimulated with 620 nm. Ultraviolet-sensitive cones were not studied. Light intensities were controlled with a set of calibrated neutral density filters, and light flashes were produced by an electronically controlled shutter in the light path.

Figure 26:
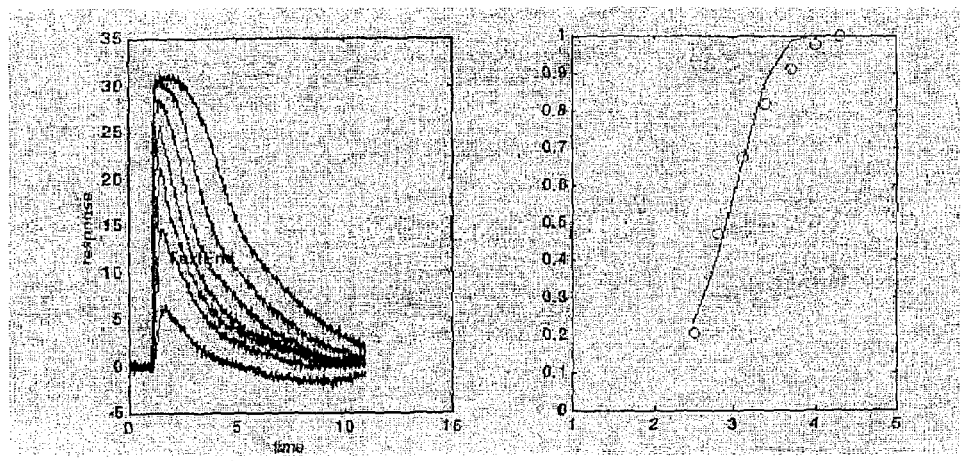
FIG. 26 is a graph showing light responses (as measured by a change in current) from isolated rods of dark-adapted salamander retinas in the presence of small molecule PL_0302R3C4.
Figure 27:
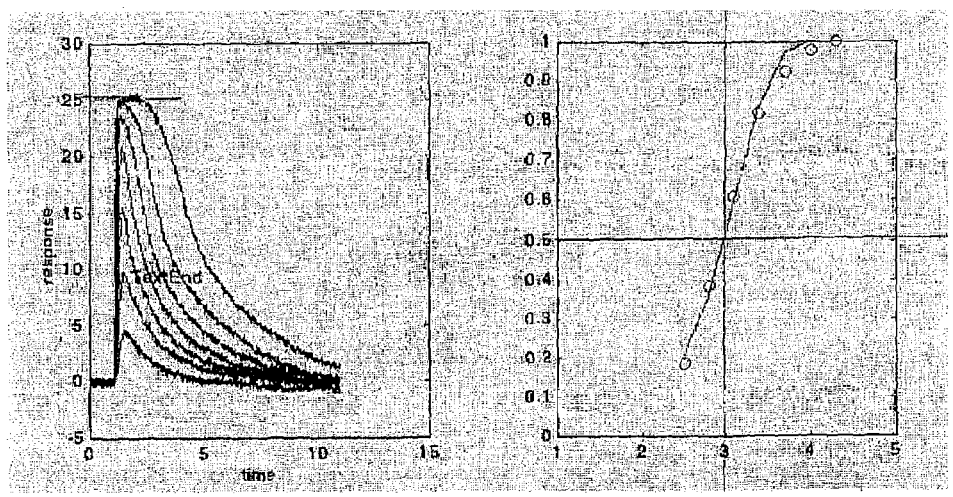
FIG. 27 is a graph showing light responses (as measured by a change in current) from isolated rods of dark-adapted salamander retinas in the absence of a small molecule.
Figure 28:
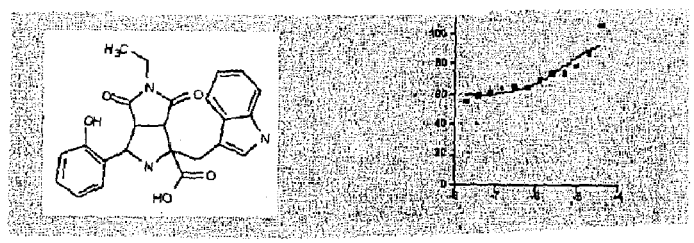
FIG. 28 is an MBP-8 binding curve with added compound PL_1012R2C1, the structure of which is depicted, showing the compound's ability to enhance MBP-8 binding to EDTA-washed rhodopsin.
Figure 29:
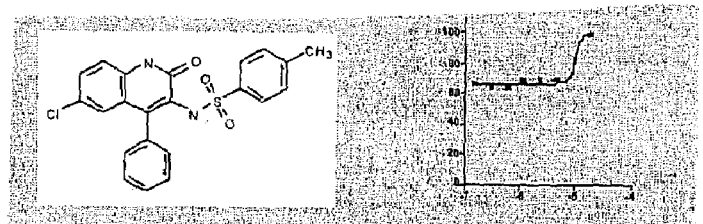
FIG. 29 is an MBP-8 binding curve with added compound PL_0894R3C7, the structure of which is depicted, showing the compound's ability to enhance MBP-8 binding to EDTA-washed rhodopsin.
Figure 30:
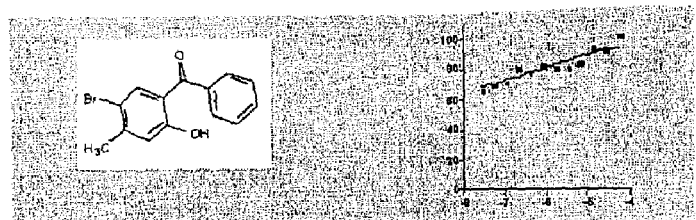
FIG. 30 is an MBP-8 binding curve with added compound PL_0568R1C5, the structure of which is depicted, showing the compound's ability to enhance MBP-8 binding to EDTA-washed rhodopsin.
Figure 31:
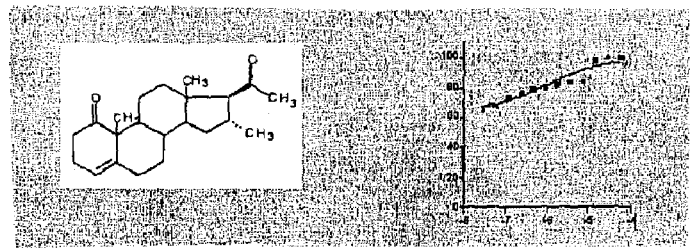
FIG. 31 is an MBP-8 binding curve with added compound PL_0551R8C1, the structure of which is depicted, showing the compound's ability to enhance MBP-8 binding to EDTA-washed rhodopsin.
Figure 32:
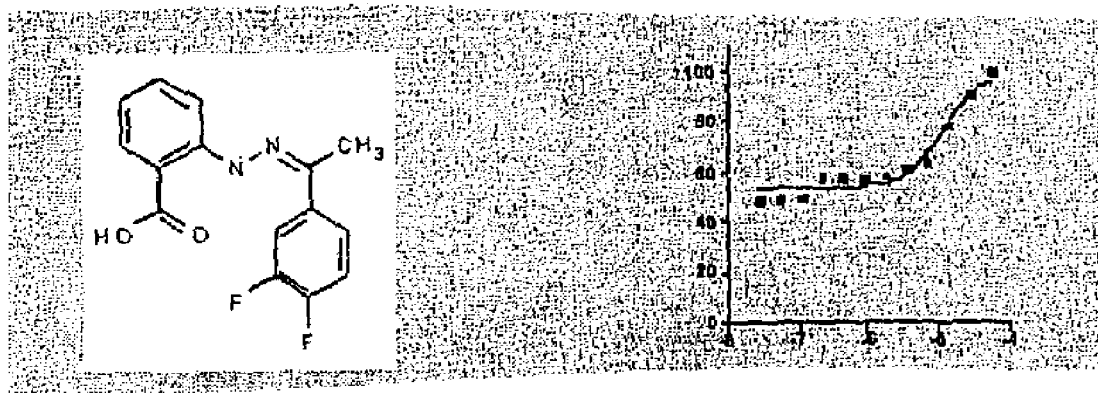
FIG. 32 is an MBP-8 binding curve with added compound PL_0302R3C4, the structure of which is depicted, showing the compound's ability to enhance MBP-8 binding to EDTA-washed rhodopsin.

The results are presented in FIGS. 26 and 27, which show the light response of an isolated rod from the dark-adapted retina of a salamander in the presence or absence of 5 μM compound PL_0302R3C4, respectively. Panel A of each figure shows the membrane current (response) plotted against time for the light responses as a result of increasing light flashes. In panel B, the peak responses have been normalized so that the current at the highest light flash is 1.0. The circles correspond to the peak response for each light flash. In FIG. 27, panel B, the bissecting lines indicate that in the presence of PL_0302R3C4 a lower intensity is required to get the same change of current. The results indicate that compound PL_0302R3C4 increases the peak response (as measured by a change in current) 20%-50%, depending on the intensity of the light flash and thus the amount of rhodopsin receptors activated. The results are representation of these separate experiments. The results suggest taht the compound PL_302R3C4 can serve as an allosteric agonist and increase the signaling activity of the receptor in cells.

Small molecules also were tested for their ability to enhance the binding of MBP-8. PELM6 (the MBP control) and MBP-8 were plated on 96 well plates that contained EDTA-washed rhodopsin. A small molecule compound library was added, and the amount of pELM6 or MBP-8 that remained bound was measured. Standard methods were used.

FIGS. 28-32 show MBP-8 binding curves for the depicted small molecules' ability to enhance binding of the high affinity peptide fusion protein, MBP-8 to EDTA-washed rhodopsin.

The invention claimed is:

1. A method of identifying a GPCR signaling modifying compound that binds to the G Protein binding domain of said GPCR, which comprises:
(a) providing a library of candidate compounds to screen for binding to said G protein binding domain of said GPCR;
(b) providing a GPCR G protein binding domain binding peptide wherein said GPCR G protein binding domain binding peptide binds to the GPCR with higher affinity than the native G protein peptide;
(c) screening said library of candidate compounds for high affinity binding to said G protein binding domain of said GPCR in competition with said GPCR G protein binding domain binding peptide; and
(d) determining whether (i) a member of said library of candidate compounds has binding to said G protein binding domain of said GPCR of equal or higher affinity than that of the peptide of step (b) or (ii) a member of said library of candidate compounds results in increased binding affinity of the peptide of step (b) when it binds to said G protein binding domain of said GPCR; and
(e) identifying compounds that bind to said G protein binding domain of said GPCR of equal or higher affinity than that of the peptide of step (b) or the binding of which to said G protein binding domain of said GPCR result in increased binding affinity of the peptide of step (b).

2. A method of claim 1, wherein said screening of step (c) is performed by testing for binding to an intact GPCR.

3. A method of claim 1, wherein said screening of step (c) is performed by testing for binding to at least an intracellular fragment of a GPCR.

4. A method of claim 1, wherein said GPCR binding peptide of step (b) is a G protein subunit or fragment thereof.

5. A method of claim 4, wherein said G protein subunit fragment is about 7 to about 70 amino acids long.

6. A method of claim 4, wherein said G protein subunit fragment is about 7 to about 55 amino acids long.

7. A method of claim 4, wherein said G protein subunit fragment is about 8 to about 50 amino acids long.

8. A method of claim 4, wherein said G protein subunit fragment is about 9 to about 23 amino acids long.

9. A method of claim 4, wherein said G protein subunit fragment is 11 amino acids long.

10. A method of claim 4, wherein said G protein subunit is a Gα subunit.

11. A method of claim 4, wherein said GPCR binding peptide is a Gα subunit carboxyl terminal peptide.

12. A method of claim 1, wherein binding to said GPCR is determined by measuring a signal generated from interaction of an activating ligand with said GPCR.

13. A method of claim 1, wherein said library of candidate compounds of step (a) is a combinatorial library.

14. A method of assaying intracellular G protein coupled receptor (GPCR) signaling modification, which comprises:
(a) providing a library comprising small molecule compound members for assay;
(b) providing a peptide that binds to said GPCR at the G protein binding domain with higher affinity than a native Gα subunit eleven carboxy-terminal peptide from a Gα subunit that binds said GPCR; and
(c) screening said small molecule library for binding to said GPCR G protein binding domain, wherein said screen is a competitive binding assay performed in the presence of said eleven carboxy terminal peptide of (b) to determine whether a small molecule library member compound binds to said GPCR G protein binding domain with equal or higher affinity than that of said peptide of (b).

15. A method of screening a small molecule library for binding to a GPCR G protein binding domain, which comprises:
(a) providing a peptide that binds to said GPCR at the G protein binding domain with higher affinity than a native Gα subunit eleven carboxy-terminal peptide from a Gα subunit that binds said GPCR; and
(b) screening said small molecule library for binding to said GPCR G protein binding domain, wherein said screen is a competitive binding assay performed in the presence of said eleven carboxy terminal peptide of (a) to determine whether a small molecule library member compound binds to said GPCR G protein binding domain with equal or higher affinity than that of said peptide of (a).

16. A method of claim 14 wherein said peptide of (a) is an undecamer.

17. A method of claim 15 wherein said peptide of (a) is an undecamer.

* * * * *

SEQUENCE LISTING

<160> NUMBER OF SEQ ID NOS: 273

<210> SEQ ID NO 1
<211> LENGTH: 4
<212> TYPE: PRT
<213> ORGANISM: Mammal
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (1)..(4)
<223> OTHER INFORMATION: MBP-G11

<400> SEQUENCE: 1

Xaa Xaa Xaa Xaa
1

<210> SEQ ID NO 2
<211> LENGTH: 11
<212> TYPE: PRT
<213> ORGANISM: Homo sapiens

<400> SEQUENCE: 2

Leu Gln Leu Asn Leu Lys Glu Tyr Asn Leu Val
1               5                   10

<210> SEQ ID NO 3
<211> LENGTH: 4
<212> TYPE: PRT
<213> ORGANISM: Mammal
<220> FEATURE:
<221> NAME/KEY: misc_feature
<222> LOCATION: (1)..(4)
<223> OTHER INFORMATION: PAR-13

<400> SEQUENCE: 3

Val Arg Pro Ser
1

<210> SEQ ID NO 4
<211> LENGTH: 11
<212> TYPE: PRT
<213> ORGANISM: Artificial Sequence
<220> FEATURE:
<223> OTHER INFORMATION: Gq peptide library sequence

<400> SEQUENCE: 4

Leu Gln Leu Asn Arg Asn Glu Tyr Tyr Leu Val
1               5                   10

<210> SEQ ID NO 5
<211> LENGTH: 4
<212> TYPE: PRT
<213> ORGANISM: Mammal

```
<220> FEATURE:
<221> NAME/KEY: misc_feature
<222> LOCATION: (1)..(4)
<223> OTHER INFORMATION: PAR-23

<400> SEQUENCE: 5

Leu Ser Arg Ser
1

<210> SEQ ID NO 6
<211> LENGTH: 11
<212> TYPE: PRT
<213> ORGANISM: Artificial Sequence
<220> FEATURE:
<223> OTHER INFORMATION: Gq peptide library sequence

<400> SEQUENCE: 6

Leu Gln Gln Lys Leu Lys Glu Tyr Ser Leu Val
1               5                   10

<210> SEQ ID NO 7
<211> LENGTH: 4
<212> TYPE: PRT
<213> ORGANISM: Mammal
<220> FEATURE:
<221> NAME/KEY: misc_feature
<222> LOCATION: (1)..(4)
<223> OTHER INFORMATION: PAR-33

<400> SEQUENCE: 7

Leu Ser Thr Asn
1

<210> SEQ ID NO 8
<211> LENGTH: 11
<212> TYPE: PRT
<213> ORGANISM: Artificial Sequence
<220> FEATURE:
<223> OTHER INFORMATION: Gq peptide library sequence

<400> SEQUENCE: 8

Leu His Leu Asn Leu Lys Glu Tyr Asn Leu Val
1               5                   10

<210> SEQ ID NO 9
<211> LENGTH: 4
<212> TYPE: PRT
<213> ORGANISM: Mammal
<220> FEATURE:
<221> NAME/KEY: misc_feature
<222> LOCATION: (1)..(4)
<223> OTHER INFORMATION: PAR-34

<400> SEQUENCE: 9

Leu Pro Gln Met
1

<210> SEQ ID NO 10
<211> LENGTH: 11
<212> TYPE: PRT
<213> ORGANISM: Artificial Sequence
<220> FEATURE:
<223> OTHER INFORMATION: Gq peptide library sequence

<400> SEQUENCE: 10

Gln Arg Leu Asn Val Gly Glu Tyr Asn Leu Val
1               5                   10
```

```
<210> SEQ ID NO 11
<211> LENGTH: 4
<212> TYPE: PRT
<213> ORGANISM: Mammal
<220> FEATURE:
<221> NAME/KEY: misc_feature
<222> LOCATION: (1)..(4)
<223> OTHER INFORMATION: PAR-45

<400> SEQUENCE: 11

Ser Arg His Thr
1

<210> SEQ ID NO 12
<211> LENGTH: 11
<212> TYPE: PRT
<213> ORGANISM: Artificial Sequence
<220> FEATURE:
<223> OTHER INFORMATION: Gq peptide library sequence

<400> SEQUENCE: 12

Leu Arg Leu Asn Gly Lys Glu Leu Asn Leu Val
1               5                   10

<210> SEQ ID NO 13
<211> LENGTH: 11
<212> TYPE: PRT
<213> ORGANISM: Homo sapiens

<400> SEQUENCE: 13

Gln Arg Met His Leu Arg Gln Tyr Glu Leu Leu
1               5                   10

<210> SEQ ID NO 14
<211> LENGTH: 67
<212> TYPE: DNA
<213> ORGANISM: Artificial Sequence
<220> FEATURE:
<223> OTHER INFORMATION: G alpha t library construct
<220> FEATURE:
<221> NAME/KEY: misc_feature
<222> LOCATION: (9)..(9)
<223> OTHER INFORMATION: n = a, c, g or t
<220> FEATURE:
<221> NAME/KEY: misc_feature
<222> LOCATION: (10)..(10)
<223> OTHER INFORMATION: n = a, c, g or t
<220> FEATURE:
<221> NAME/KEY: misc_feature
<222> LOCATION: (12)..(12)
<223> OTHER INFORMATION: n = a, c, g or t
<220> FEATURE:
<221> NAME/KEY: misc_feature
<222> LOCATION: (13)..(13)
<223> OTHER INFORMATION: n = a, c, g or t
<220> FEATURE:
<221> NAME/KEY: misc_feature
<222> LOCATION: (15)..(15)
<223> OTHER INFORMATION: n = a, c, g or t
<220> FEATURE:
<221> NAME/KEY: misc_feature
<222> LOCATION: (16)..(16)
<223> OTHER INFORMATION: n = a, c, g or t
<220> FEATURE:
<221> NAME/KEY: misc_feature
<222> LOCATION: (18)..(18)
<223> OTHER INFORMATION: n = a, c, g or t
<220> FEATURE:
<221> NAME/KEY: misc_feature
<222> LOCATION: (19)..(19)
<223> OTHER INFORMATION: n = a, c, g or t
```

```
<400> SEQUENCE: 14
gaggtggtnn knnknnknnk attcgtgaaa acttaaaaga ttgtggtcgt ttctaactaa      60
gtaaagc                                                               67

<210> SEQ ID NO 15
<211> LENGTH: 11
<212> TYPE: PRT
<213> ORGANISM: Homo sapiens

<400> SEQUENCE: 15

Ile Lys Glu Asn Leu Lys Asp Cys Gly Leu Phe
1               5                   10

<210> SEQ ID NO 16
<211> LENGTH: 33
<212> TYPE: DNA
<213> ORGANISM: Homo sapiens

<400> SEQUENCE: 16
atcaaggaga acctgaaaga ctgcggcctc ttc                                  33

<210> SEQ ID NO 17
<211> LENGTH: 11
<212> TYPE: PRT
<213> ORGANISM: Homo sapiens

<400> SEQUENCE: 17

Ile Lys Asn Asn Leu Lys Asp Cys Gly Leu Phe
1               5                   10

<210> SEQ ID NO 18
<211> LENGTH: 33
<212> TYPE: DNA
<213> ORGANISM: Homo sapiens

<400> SEQUENCE: 18
ataaaaaata atctaaaaga ttgtggtctc ttc                                  33

<210> SEQ ID NO 19
<211> LENGTH: 11
<212> TYPE: PRT
<213> ORGANISM: Artificial Sequence
<220> FEATURE:
<223> OTHER INFORMATION: G alpha i 1/2 sequence in random order

<400> SEQUENCE: 19

Asn Gly Ile Lys Cys Leu Phe Asn Asp Lys Leu
1               5                   10

<210> SEQ ID NO 20
<211> LENGTH: 33
<212> TYPE: DNA
<213> ORGANISM: Artificial Sequence
<220> FEATURE:
<223> OTHER INFORMATION: G alpha i 1/2 sequence in random order

<400> SEQUENCE: 20
aacggcatca agtgcctctt caacgacaag ctg                                  33

<210> SEQ ID NO 21
<211> LENGTH: 11
<212> TYPE: PRT
<213> ORGANISM: Homo sapiens
```

<400> SEQUENCE: 21

Ile Lys Asn Asn Leu Lys Glu Cys Gly Leu Tyr
1               5                   10

<210> SEQ ID NO 22
<211> LENGTH: 33
<212> TYPE: DNA
<213> ORGANISM: Homo sapiens

<400> SEQUENCE: 22
attaaaaaca acttaaagga atgtggactt tat                               33

<210> SEQ ID NO 23
<211> LENGTH: 11
<212> TYPE: PRT
<213> ORGANISM: Homo sapiens

<400> SEQUENCE: 23

Ile Ala Lys Asn Leu Arg Gly Cys Gly Leu Tyr
1               5                   10

<210> SEQ ID NO 24
<211> LENGTH: 33
<212> TYPE: DNA
<213> ORGANISM: Homo sapiens

<400> SEQUENCE: 24
atcgccaaaa acctgcgggg ctgtggactc tac                               33

<210> SEQ ID NO 25
<211> LENGTH: 11
<212> TYPE: PRT
<213> ORGANISM: Homo sapiens

<400> SEQUENCE: 25

Ile Ala Asn Asn Leu Arg Gly Cys Gly Leu Tyr
1               5                   10

<210> SEQ ID NO 26
<211> LENGTH: 33
<212> TYPE: DNA
<213> ORGANISM: Homo sapiens

<400> SEQUENCE: 26
attgccaaca acctccgggg ctgcggcttg tac                               33

<210> SEQ ID NO 27
<211> LENGTH: 11
<212> TYPE: PRT
<213> ORGANISM: Homo sapiens

<400> SEQUENCE: 27

Ile Gln Asn Asn Leu Lys Tyr Ile Gly Leu Cys
1               5                   10

<210> SEQ ID NO 28
<211> LENGTH: 33
<212> TYPE: DNA
<213> ORGANISM: Homo sapiens

<400> SEQUENCE: 28
atacagaaca atctcaagta cattggcctt tgc                               33

```
<210> SEQ ID NO 29
<211> LENGTH: 33
<212> TYPE: DNA
<213> ORGANISM: Homo sapiens

<400> SEQUENCE: 29
ctgcagctga acctcaagga gtacaacctg gtc                                    33

<210> SEQ ID NO 30
<211> LENGTH: 11
<212> TYPE: PRT
<213> ORGANISM: Homo sapiens

<400> SEQUENCE: 30

Leu Gln Leu Asn Leu Lys Glu Tyr Asn Ala Val
1               5                   10

<210> SEQ ID NO 31
<211> LENGTH: 33
<212> TYPE: DNA
<213> ORGANISM: Homo sapiens

<400> SEQUENCE: 31
ctccagttga acctgaagga gtacaatgca gtc                                    33

<210> SEQ ID NO 32
<211> LENGTH: 11
<212> TYPE: PRT
<213> ORGANISM: Homo sapiens

<400> SEQUENCE: 32

Gln Arg Met His Leu Lys Gln Tyr Glu Leu Leu
1               5                   10

<210> SEQ ID NO 33
<211> LENGTH: 33
<212> TYPE: DNA
<213> ORGANISM: Homo sapiens

<400> SEQUENCE: 33
cagcggatgc acctcaagca gtatgagctc ttg                                    33

<210> SEQ ID NO 34
<211> LENGTH: 11
<212> TYPE: PRT
<213> ORGANISM: Homo sapiens

<400> SEQUENCE: 34

Leu Gln Leu Asn Leu Arg Glu Phe Asn Leu Val
1               5                   10

<210> SEQ ID NO 35
<211> LENGTH: 33
<212> TYPE: DNA
<213> ORGANISM: Homo sapiens

<400> SEQUENCE: 35
ctacagctaa acctaaggga attcaacctt gtc                                    33

<210> SEQ ID NO 36
<211> LENGTH: 11
<212> TYPE: PRT
<213> ORGANISM: Homo sapiens

<400> SEQUENCE: 36
```

-continued

Leu Ala Arg Tyr Leu Asp Glu Ile Asn Leu Leu
1               5                   10

<210> SEQ ID NO 37
<211> LENGTH: 33
<212> TYPE: DNA
<213> ORGANISM: Homo sapiens

<400> SEQUENCE: 37
ctcgcccgct acctggacga gatcaacctg ctg                         33

<210> SEQ ID NO 38
<211> LENGTH: 11
<212> TYPE: PRT
<213> ORGANISM: Homo sapiens

<400> SEQUENCE: 38

Leu Gln Glu Asn Leu Lys Asp Ile Met Leu Gln
1               5                   10

<210> SEQ ID NO 39
<211> LENGTH: 33
<212> TYPE: DNA
<213> ORGANISM: Homo sapiens

<400> SEQUENCE: 39
ctgcaggaga acctgaagga catcatgctg cag                         33

<210> SEQ ID NO 40
<211> LENGTH: 11
<212> TYPE: PRT
<213> ORGANISM: Homo sapiens

<400> SEQUENCE: 40

Leu His Asp Asn Leu Lys Gln Leu Met Leu Gln
1               5                   10

<210> SEQ ID NO 41
<211> LENGTH: 33
<212> TYPE: DNA
<213> ORGANISM: Homo sapiens

<400> SEQUENCE: 41
ctgcatgaca acctcaagca gcttatgcta cag                         33

<210> SEQ ID NO 42
<211> LENGTH: 33
<212> TYPE: DNA
<213> ORGANISM: Homo sapiens

<400> SEQUENCE: 42
cagcgcatgc accttcgtca gtacgagctg ctc                         33

<210> SEQ ID NO 43
<211> LENGTH: 20
<212> TYPE: DNA
<213> ORGANISM: Artificial Sequence
<220> FEATURE:
<223> OTHER INFORMATION: 5' minigene construct sequence

<400> SEQUENCE: 43
gatccgccgc caccatggga                                        20

<210> SEQ ID NO 44
<211> LENGTH: 4
<212> TYPE: DNA
<213> ORGANISM: Artificial Sequence
<220> FEATURE:
<223> OTHER INFORMATION: 3' minigene construct sequence

<400> SEQUENCE: 44 tgaa                                                                    4

<210> SEQ ID NO 45
<211> LENGTH: 11
<212> TYPE: PRT
<213> ORGANISM: Drosophila melanogaster

<400> SEQUENCE: 45

Ile Lys Asn Asn Leu Lys Gln Ile Gly Leu Phe
1               5                   10

<210> SEQ ID NO 46
<211> LENGTH: 11
<212> TYPE: PRT
<213> ORGANISM: Drosophila melanogaster

<400> SEQUENCE: 46

Leu Ser Glu Asn Val Ser Ser Met Gly Leu Phe
1               5                   10

<210> SEQ ID NO 47
<211> LENGTH: 11
<212> TYPE: PRT
<213> ORGANISM: Homo sapiens

<400> SEQUENCE: 47

Ile Ala Lys Asn Leu Arg Gly Cys Gly Leu Tyr
1               5                   10

<210> SEQ ID NO 48
<211> LENGTH: 11
<212> TYPE: PRT
<213> ORGANISM: Xenopus laevis

<400> SEQUENCE: 48

Ile Ala Tyr Asn Leu Arg Gly Cys Gly Leu Tyr
1               5                   10

<210> SEQ ID NO 49
<211> LENGTH: 11
<212> TYPE: PRT
<213> ORGANISM: Caenorhabditis elegans

<400> SEQUENCE: 49

Ile Gln Ala Asn Leu Gln Gly Cys Gly Leu Tyr
1               5                   10

<210> SEQ ID NO 50
<211> LENGTH: 11
<212> TYPE: PRT
<213> ORGANISM: Caenorhabditis elegans

<400> SEQUENCE: 50

Ile Gln Ser Asn Leu His Lys Ser Gly Leu Tyr
1               5                   10

<210> SEQ ID NO 51

```
<211> LENGTH: 11
<212> TYPE: PRT
<213> ORGANISM: Caenorhabditis elegans

<400> SEQUENCE: 51

Leu Ser Thr Lys Leu Lys Gly Cys Gly Leu Tyr
1               5                   10

<210> SEQ ID NO 52
<211> LENGTH: 11
<212> TYPE: PRT
<213> ORGANISM: Xenopus laevis

<400> SEQUENCE: 52

Ile Lys Ser Asn Leu Met Glu Cys Gly Leu Tyr
1               5                   10

<210> SEQ ID NO 53
<211> LENGTH: 11
<212> TYPE: PRT
<213> ORGANISM: Canis familiaris

<400> SEQUENCE: 53

Val Gln Gln Asn Leu Lys Lys Ser Gly Ile Met
1               5                   10

<210> SEQ ID NO 54
<211> LENGTH: 11
<212> TYPE: PRT
<213> ORGANISM: Schizosaccharomyces pombe

<400> SEQUENCE: 54

Leu Gln His Ser Leu Lys Glu Ala Gly Met Phe
1               5                   10

<210> SEQ ID NO 55
<211> LENGTH: 11
<212> TYPE: PRT
<213> ORGANISM: Drosophila melanogaster

<400> SEQUENCE: 55

Leu Gln Arg Asn Leu Asn Ala Leu Met Leu Gln
1               5                   10

<210> SEQ ID NO 56
<211> LENGTH: 11
<212> TYPE: PRT
<213> ORGANISM: Saccharomyces cerevisiae

<400> SEQUENCE: 56

Glu Asn Thr Leu Lys Asp Ser Gly Val Leu Gln
1               5                   10

<210> SEQ ID NO 57
<211> LENGTH: 11
<212> TYPE: PRT
<213> ORGANISM: Drosophila melanogaster

<400> SEQUENCE: 57

Leu Gln Ser Asn Leu Lys Glu Tyr Asn Leu Val
1               5                   10

<210> SEQ ID NO 58
<211> LENGTH: 11
<212> TYPE: PRT
```

<213> ORGANISM: Xenopus laevis

<400> SEQUENCE: 58

Leu Gln His Asn Leu Lys Glu Tyr Asn Leu Val
1               5                   10

<210> SEQ ID NO 59
<211> LENGTH: 11
<212> TYPE: PRT
<213> ORGANISM: Sporothrix schenckii

<400> SEQUENCE: 59

Ile Gln Glu Asn Leu Arg Leu Cys Gly Leu Ile
1               5                   10

<210> SEQ ID NO 60
<211> LENGTH: 11
<212> TYPE: PRT
<213> ORGANISM: Saccharomyces cerevisiae

<400> SEQUENCE: 60

Ile Gln Gln Asn Leu Lys Lys Ile Gly Ile Ile
1               5                   10

<210> SEQ ID NO 61
<211> LENGTH: 11
<212> TYPE: PRT
<213> ORGANISM: Neurospora crassa

<400> SEQUENCE: 61

Ile Ile Gln Arg Asn Leu Lys Gln Leu Ile Leu
1               5                   10

<210> SEQ ID NO 62
<211> LENGTH: 11
<212> TYPE: PRT
<213> ORGANISM: Filobasidiella neoformans

<400> SEQUENCE: 62

Leu Gln Asn Ala Leu Arg Asp Ser Gly Ile Leu
1               5                   10

<210> SEQ ID NO 63
<211> LENGTH: 11
<212> TYPE: PRT
<213> ORGANISM: Ustilago maydis

<400> SEQUENCE: 63

Leu Thr Asn Ala Leu Lys Asp Ser Gly Ile Leu
1               5                   10

<210> SEQ ID NO 64
<211> LENGTH: 11
<212> TYPE: PRT
<213> ORGANISM: Kluyveromyces lactis

<400> SEQUENCE: 64

Ile Gln Gln Asn Leu Lys Lys Ser Gly Ile Leu
1               5                   10

<210> SEQ ID NO 65
<211> LENGTH: 11
<212> TYPE: PRT
<213> ORGANISM: Kluyveromyces lactis

```
<400> SEQUENCE: 65

Leu Glu Asn Ser Leu Lys Asp Ser Gly Val Leu
1               5                   10

<210> SEQ ID NO 66
<211> LENGTH: 11
<212> TYPE: PRT
<213> ORGANISM: Ustilago maydis

<400> SEQUENCE: 66

Ile Leu Thr Asn Asn Leu Arg Asp Ile Val Leu
1               5                   10

<210> SEQ ID NO 67
<211> LENGTH: 11
<212> TYPE: PRT
<213> ORGANISM: Mus musculus

<400> SEQUENCE: 67

Gln Arg Met His Leu Pro Gln Tyr Glu Leu Leu
1               5                   10

<210> SEQ ID NO 68
<211> LENGTH: 11
<212> TYPE: PRT
<213> ORGANISM: Homo sapiens

<400> SEQUENCE: 68

Gln Arg Met His Leu Lys Gly Tyr Glu Leu Leu
1               5                   10

<210> SEQ ID NO 69
<211> LENGTH: 11
<212> TYPE: PRT
<213> ORGANISM: Coprinus congregatus

<400> SEQUENCE: 69

Leu Gln Leu His Leu Arg Glu Cys Gly Leu Leu
1               5                   10

<210> SEQ ID NO 70
<211> LENGTH: 11
<212> TYPE: PRT
<213> ORGANISM: Lycopersicon esculentum

<400> SEQUENCE: 70

Arg Arg Arg Asn Leu Phe Glu Ala Gly Leu Leu
1               5                   10

<210> SEQ ID NO 71
<211> LENGTH: 11
<212> TYPE: PRT
<213> ORGANISM: Glycine max

<400> SEQUENCE: 71

Arg Arg Arg Asn Leu Leu Glu Ala Gly Leu Leu
1               5                   10

<210> SEQ ID NO 72
<211> LENGTH: 11
<212> TYPE: PRT
<213> ORGANISM: Glycine max

<400> SEQUENCE: 72
```

Arg Arg Arg Asn Pro Leu Glu Ala Gly Leu Leu
1               5                   10

<210> SEQ ID NO 73
<211> LENGTH: 11
<212> TYPE: PRT
<213> ORGANISM: Ustilago maydis

<400> SEQUENCE: 73

Ile Gln Val Asn Leu Arg Asp Cys Gly Leu Leu
1               5                   10

<210> SEQ ID NO 74
<211> LENGTH: 11
<212> TYPE: PRT
<213> ORGANISM: Ustilago maydis

<400> SEQUENCE: 74

Arg Glu Asn Leu Lys Leu Thr Gly Leu Val Gly
1               5                   10

<210> SEQ ID NO 75
<211> LENGTH: 11
<212> TYPE: PRT
<213> ORGANISM: Oryza sativa

<400> SEQUENCE: 75

Asp Glu Ser Met Arg Arg Ser Arg Glu Gly Thr
1               5                   10

<210> SEQ ID NO 76
<211> LENGTH: 11
<212> TYPE: PRT
<213> ORGANISM: Calliphora vicina

<400> SEQUENCE: 76

Met Gln Asn Ala Leu Lys Glu Phe Asn Leu Gly
1               5                   10

<210> SEQ ID NO 77
<211> LENGTH: 11
<212> TYPE: PRT
<213> ORGANISM: Dictyostelium discoideum

<400> SEQUENCE: 77

Thr Gln Cys Val Met Lys Ala Gly Leu Tyr Ser
1               5                   10

<210> SEQ ID NO 78
<211> LENGTH: 11
<212> TYPE: PRT
<213> ORGANISM: Caenorhabditis elegans

<400> SEQUENCE: 78

Ile Ile Ser Ala Ser Leu Lys Met Val Gly Val
1               5                   10

<210> SEQ ID NO 79
<211> LENGTH: 11
<212> TYPE: PRT
<213> ORGANISM: Caenorhabditis elegans

<400> SEQUENCE: 79

Asn Glu Asn Leu Arg Ser Ala Gly Leu His Glu
1               5                   10

```
<210> SEQ ID NO 80
<211> LENGTH: 11
<212> TYPE: PRT
<213> ORGANISM: Caenorhabditis elegans

<400> SEQUENCE: 80

Arg Leu Ile Arg Tyr Ala Asn Asn Ile Pro Val
1               5                   10

<210> SEQ ID NO 81
<211> LENGTH: 11
<212> TYPE: PRT
<213> ORGANISM: Caenorhabditis elegans

<400> SEQUENCE: 81

Ile Ala Lys Asn Leu Lys Ser Met Gly Leu Cys
1               5                   10

<210> SEQ ID NO 82
<211> LENGTH: 11
<212> TYPE: PRT
<213> ORGANISM: Caenorhabditis elegans

<400> SEQUENCE: 82

Ile Gly Arg Asn Leu Arg Gly Thr Gly Met Glu
1               5                   10

<210> SEQ ID NO 83
<211> LENGTH: 11
<212> TYPE: PRT
<213> ORGANISM: Caenorhabditis elegans

<400> SEQUENCE: 83

Ile Gln His Thr Met Gln Lys Val Gly Ile Gln
1               5                   10

<210> SEQ ID NO 84
<211> LENGTH: 11
<212> TYPE: PRT
<213> ORGANISM: Caenorhabditis elegans

<400> SEQUENCE: 84

Ile Gln Lys Asn Leu Gln Lys Ala Gly Met Met
1               5                   10

<210> SEQ ID NO 85
<211> LENGTH: 11
<212> TYPE: PRT
<213> ORGANISM: Dictyostelium discoideum

<400> SEQUENCE: 85

Leu Lys Asn Ile Phe Asn Thr Ile Ile Asn Tyr
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Gq library peptide

<400> SEQUENCE: 86

Leu Leu Leu Gln Leu Val Glu His Thr Leu Val
1               5                   10
```

```
<210> SEQ ID NO 87
<211> LENGTH: 11
<212> TYPE: PRT
<213> ORGANISM: Artificial Sequence
<220> FEATURE:
<223> OTHER INFORMATION: Gq library peptide

<400> SEQUENCE: 87

His Arg Leu Asn Leu Leu Glu Tyr Cys Leu Val
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Gq library peptide

<400> SEQUENCE: 88

Glu Gln Trp Asn Met Asn Thr Phe His Met Ile
1               5                   10

<210> SEQ ID NO 89
<211> LENGTH: 11
<212> TYPE: PRT
<213> ORGANISM: Artificial Sequence
<220> FEATURE:
<223> OTHER INFORMATION: Gq library peptide

<400> SEQUENCE: 89

Ser Gln Val Lys Leu Gln Lys Gly His Leu Val
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Gq library sequence

<400> SEQUENCE: 90

Leu Arg Leu Leu Leu Glu Tyr Asn Leu Gly
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Gq library peptide

<400> SEQUENCE: 91

Arg Arg Leu Lys Val Asn Glu Tyr Lys Leu Leu
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Gq library peptide

<400> SEQUENCE: 92

Leu Gln Leu Arg Leu Arg Glu His Asn Leu Val
1               5                   10
```

```
<210> SEQ ID NO 93
<211> LENGTH: 11
<212> TYPE: PRT
<213> ORGANISM: Artificial Sequence
<220> FEATURE:
<223> OTHER INFORMATION: Gq library peptide

<400> SEQUENCE: 93

His Val Leu Asn Ser Lys Glu Tyr Asn Gln Val
1               5                   10

<210> SEQ ID NO 94
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 94

Met Lys Leu Asn Val Ser Glu Ser Asn Leu Val
1               5                   10

<210> SEQ ID NO 95
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 95

Leu Gln Thr Asn Gln Lys Glu Tyr Asp Met Asp
1               5                   10

<210> SEQ ID NO 96
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 96

Leu Gln Leu Asn Pro Arg Glu Asp Lys Leu Trp
1               5                   10

<210> SEQ ID NO 97
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 97

Arg His Leu Asp Leu Asn Ala Cys Asn Met Gly
1               5                   10

<210> SEQ ID NO 98
<211> LENGTH: 10
<212> TYPE: PRT
<213> ORGANISM: Artificial Sequence
<220> FEATURE:
<223> OTHER INFORMATION: G alpha 11 library peptide

<400> SEQUENCE: 98

Leu Arg Asn Asp Ile Glu Ala Leu Leu Val
1               5                   10
```

<210> SEQ ID NO 99
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 99

Leu Val Gln Asp Arg Gln Glu Ser Ile Leu Val
1               5                   10

<210> SEQ ID NO 100
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 100

Leu Gln Leu Lys His Lys Glu Asn Asn Leu Met
1               5                   10

<210> SEQ ID NO 101
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 101

Leu Gln Val Asn Leu Glu Glu Tyr His Leu Val
1               5                   10

<210> SEQ ID NO 102
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 102

Leu Gln Phe Asn Leu Asn Asp Cys Asn Leu Val
1               5                   10

<210> SEQ ID NO 103
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 103

Met Lys Leu Lys Leu Lys Glu Asp Asn Leu Val
1               5                   10

<210> SEQ ID NO 104
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 104

His Gln Leu Asp Leu Leu Glu Tyr Asn Leu Gly
1               5                   10

<210> SEQ ID NO 105

```
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 105

Leu Arg Leu Asp Phe Ser Glu Lys Gln Leu Val
1               5                   10

<210> SEQ ID NO 106
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 106

Leu Gln Lys Asn Leu Lys Glu Tyr Asn Met Val
1               5                   10

<210> SEQ ID NO 107
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 107

Leu Gln Tyr Asn Leu Met Glu Asp Tyr Leu Asn
1               5                   10

<210> SEQ ID NO 108
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 108

Leu Gln Met Tyr Leu Arg Gly Tyr Asn Leu Val
1               5                   10

<210> SEQ ID NO 109
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 109

Leu Pro Leu Asn Pro Lys Glu Tyr Ser Leu Val
1               5                   10

<210> SEQ ID NO 110
<211> LENGTH: 11
<212> TYPE: PRT
<213> ORGANISM: Artificial Sequence
<220> FEATURE:
<223> OTHER INFORMATION: G alpha 11 library peptide

<400> SEQUENCE: 110

Met Asn Leu Thr Leu Lys Glu Cys Asn Leu Val
1               5                   10

<210> SEQ ID NO 111
<211> LENGTH: 11
```

```
<212> TYPE: PRT
<213> ORGANISM: Artificial Sequence
<220> FEATURE:
<223> OTHER INFORMATION: G alpha 11 library peptide

<400> SEQUENCE: 111

Leu Gln Gln Ser Leu Ile Glu Tyr Asn Leu Leu
1               5                   10

<210> SEQ ID NO 112
<211> LENGTH: 13
<212> TYPE: PRT
<213> ORGANISM: Artificial Sequence
<220> FEATURE:
<223> OTHER INFORMATION: G alpha i minigene peptide

<400> SEQUENCE: 112

Met Gly Ile Lys Asn Asn Leu Lys Asp Cys Gly Leu Phe
1               5                   10

<210> SEQ ID NO 113
<211> LENGTH: 13
<212> TYPE: PRT
<213> ORGANISM: Artificial Sequence
<220> FEATURE:
<223> OTHER INFORMATION: G alpha i R minigene peptide

<400> SEQUENCE: 113

Met Gly Asn Gly Ile Lys Cys Leu Phe Asn Asp Lys Leu
1               5                   10

<210> SEQ ID NO 114
<211> LENGTH: 13
<212> TYPE: PRT
<213> ORGANISM: Artificial Sequence
<220> FEATURE:
<223> OTHER INFORMATION: G alpha q minigene peptide

<400> SEQUENCE: 114

Met Gly Leu Gln Leu Asn Leu Lys Glu Tyr Asn Ala Val
1               5                   10

<210> SEQ ID NO 115
<211> LENGTH: 13
<212> TYPE: PRT
<213> ORGANISM: Artificial Sequence
<220> FEATURE:
<223> OTHER INFORMATION: G alpha q** minigene peptide

<400> SEQUENCE: 115

Met Gly Leu Gln Leu Asn Leu Lys Glu Tyr Asn Thr Leu
1               5                   10

<210> SEQ ID NO 116
<211> LENGTH: 13
<212> TYPE: PRT
<213> ORGANISM: Artificial Sequence
<220> FEATURE:
<223> OTHER INFORMATION: G alpha 12 minigene peptide

<400> SEQUENCE: 116

Met Gly Leu Gln Glu Asn Leu Lys Asp Ile Met Leu Gln
1               5                   10

<210> SEQ ID NO 117
<211> LENGTH: 13
<212> TYPE: PRT
```

<213> ORGANISM: Artificial Sequence
<220> FEATURE:
<223> OTHER INFORMATION: G alpha 13 minigene peptide

<400> SEQUENCE: 117

Met Gly Leu His Asp Asn Leu Lys Gln Leu Met Leu Gln
1               5                   10

<210> SEQ ID NO 118
<211> LENGTH: 68
<212> TYPE: DNA
<213> ORGANISM: Artificial Sequence
<220> FEATURE:
<223> OTHER INFORMATION: G alpha t library construct
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 118
gaggtggtnn knnknnknnk attcaaggag aacctgaagg actgcggcct cttctaacta      60
agtaaagc                                                              68

<210> SEQ ID NO 119
<211> LENGTH: 67
<212> TYPE: DNA
<213> ORGANISM: Artificial Sequence
<220> FEATURE:
<223> OTHER INFORMATION: Gs library construct
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:

```
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 119
gaggtggtnn knnknnknnk ctgcagctga acctgaagga gtacaatctg gtctaactaa       60
gtaaagc                                                                 67

<210> SEQ ID NO 120
<211> LENGTH: 67
<212> TYPE: DNA
<213> ORGANISM: Artificial Sequence
<220> FEATURE:
<223> OTHER INFORMATION: G12 library construct
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 120
gaggtggtnn knnknnknnk ctgcaggaga acctgaagga catcatgctg cagtaactaa       60
gtaaagc                                                                 67

<210> SEQ ID NO 121
<211> LENGTH: 67
<212> TYPE: DNA
<213> ORGANISM: Artificial Sequence
<220> FEATURE:
<223> OTHER INFORMATION: G13 library construct
<220> FEATURE:
<221> NAME/KEY: misc_feature
<222> LOCATION: (9)..(9)
<223> OTHER INFORMATION: n is a, c, g, or t
```

```
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 121
gaggtggtnn knnknnknnk ctgcatgaca acctcaagca gcttatgcta cagtaactaa      60
gtaaagc                                                                67

<210> SEQ ID NO 122
<211> LENGTH: 67
<212> TYPE: DNA
<213> ORGANISM: Artificial Sequence
<220> FEATURE:
<223> OTHER INFORMATION: G15 library construct
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 122
gaggtggtnn knnknnknnk ctcgcccggt acctggacga gattaatctg ctgtaactaa      60
```

```
gtaaagc                                                             67
```

<210> SEQ ID NO 123
<211> LENGTH: 67
<212> TYPE: DNA
<213> ORGANISM: Artificial Sequence
<220> FEATURE:
<223> OTHER INFORMATION: Gz library construct
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 123

```
gaggtggtnn knnknnknnk atacagaaca atctcaagta cattggcctt tgctaactaa   60
gtaaagc                                                             67
```

<210> SEQ ID NO 124
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 124

```
Ile Arg Glu Asn Leu Lys Asp Cys Gly Leu Phe
1               5                   10
```

<210> SEQ ID NO 125
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 125

```
Leu Leu Glu Asn Leu Arg Asp Cys Gly Met Phe
1               5                   10
```

<210> SEQ ID NO 126
<211> LENGTH: 11
<212> TYPE: PRT
<213> ORGANISM: Artificial Sequence

```
<220> FEATURE:
<223> OTHER INFORMATION: G alpha t library peptide

<400> SEQUENCE: 126

Ile Gln Gly Val Leu Lys Asp Cys Gly Leu Leu
1               5                   10

<210> SEQ ID NO 127
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 127

Ile Cys Glu Asn Leu Lys Glu Cys Gly Leu Phe
1               5                   10

<210> SEQ ID NO 128
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 128

Met Leu Glu Asn Leu Lys Asp Cys Gly Leu Phe
1               5                   10

<210> SEQ ID NO 129
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 129

Val Leu Glu Asp Leu Lys Ser Cys Gly Leu Phe
1               5                   10

<210> SEQ ID NO 130
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 130

Met Leu Lys Asn Leu Lys Asp Cys Gly Met Phe
1               5                   10

<210> SEQ ID NO 131
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 131

Leu Leu Asp Asn Ile Lys Asp Cys Gly Leu Phe
1               5                   10

<210> SEQ ID NO 132
<211> LENGTH: 11
<212> TYPE: PRT
<213> ORGANISM: Artificial Sequence
<220> FEATURE:
```

```
<223> OTHER INFORMATION: G alpha t library peptide

<400> SEQUENCE: 132

Ile Leu Thr Lys Leu Thr Asp Cys Gly Leu Phe
1               5                   10

<210> SEQ ID NO 133
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 133

Leu Arg Glu Ser Leu Lys Gln Cys Gly Leu Phe
1               5                   10

<210> SEQ ID NO 134
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 134

Ile His Ala Ser Leu Arg Asp Cys Gly Leu Phe
1               5                   10

<210> SEQ ID NO 135
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 135

Ile Arg Gly Ser Leu Lys Asp Cys Gly Leu Phe
1               5                   10

<210> SEQ ID NO 136
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 136

Ile Phe Leu Asn Leu Lys Asp Cys Gly Leu Phe
1               5                   10

<210> SEQ ID NO 137
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 137

Ile Arg Glu Asn Leu Glu Asp Cys Gly Leu Phe
1               5                   10

<210> SEQ ID NO 138
<211> LENGTH: 11
<212> TYPE: PRT
<213> ORGANISM: Artificial Sequence
<220> FEATURE:
<223> OTHER INFORMATION: G alpha t library peptide
```

-continued

<400> SEQUENCE: 138

Ile Ile Asp Asn Leu Lys Asp Cys Gly Leu Phe
1               5                   10

<210> SEQ ID NO 139
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 139

Met Arg Glu Ser Leu Lys Asp Cys Gly Leu Phe
1               5                   10

<210> SEQ ID NO 140
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 140

Ile Arg Glu Thr Leu Lys Asp Cys Gly Leu Leu
1               5                   10

<210> SEQ ID NO 141
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 141

Ile Leu Ala Asp Val Ile Asp Cys Gly Leu Phe
1               5                   10

<210> SEQ ID NO 142
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 142

Met Cys Glu Ser Leu Lys Glu Cys Gly Leu Phe
1               5                   10

<210> SEQ ID NO 143
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 143

Ile Arg Glu Lys Trp Lys Asp Leu Ala Leu Phe
1               5                   10

<210> SEQ ID NO 144
<211> LENGTH: 11
<212> TYPE: PRT
<213> ORGANISM: Artificial Sequence
<220> FEATURE:
<223> OTHER INFORMATION: G alpha t library sequence

```
<400> SEQUENCE: 144

Val Arg Asp Asn Leu Lys Asn Cys Phe Leu Phe
1               5                   10

<210> SEQ ID NO 145
<211> LENGTH: 11
<212> TYPE: PRT
<213> ORGANISM: Artificial Sequence
<220> FEATURE:
<223> OTHER INFORMATION: G alpha t library sequence

<400> SEQUENCE: 145

Ile Gly Glu Gln Ile Glu Asp Cys Gly Pro Phe
1               5                   10

<210> SEQ ID NO 146
<211> LENGTH: 11
<212> TYPE: PRT
<213> ORGANISM: Artificial Sequence
<220> FEATURE:
<223> OTHER INFORMATION: G alpha t library sequence

<400> SEQUENCE: 146

Ile Arg Asn Asn Leu Lys Arg Tyr Gly Met Phe
1               5                   10

<210> SEQ ID NO 147
<211> LENGTH: 11
<212> TYPE: PRT
<213> ORGANISM: Artificial Sequence
<220> FEATURE:
<223> OTHER INFORMATION: G alpha t library sequence

<400> SEQUENCE: 147

Ile Arg Glu Asn Leu Lys Asp Leu Gly Leu Val
1               5                   10

<210> SEQ ID NO 148
<211> LENGTH: 11
<212> TYPE: PRT
<213> ORGANISM: Artificial Sequence
<220> FEATURE:
<223> OTHER INFORMATION: G alpha t library sequence

<400> SEQUENCE: 148

Ile Arg Glu Asn Phe Lys Tyr Leu Gly Leu Trp
1               5                   10

<210> SEQ ID NO 149
<211> LENGTH: 11
<212> TYPE: PRT
<213> ORGANISM: Artificial Sequence
<220> FEATURE:
<223> OTHER INFORMATION: G alpha t library sequence

<400> SEQUENCE: 149

Ser Leu Glu Ile Leu Lys Asp Trp Gly Leu Phe
1               5                   10

<210> SEQ ID NO 150
<211> LENGTH: 11
<212> TYPE: PRT
<213> ORGANISM: Artificial Sequence
<220> FEATURE:
<223> OTHER INFORMATION: G alpha t library sequence

<400> SEQUENCE: 150
```

Ile Arg Gly Thr Leu Lys Gly Trp Gly Leu Phe
1               5                   10

<210> SEQ ID NO 151
<211> LENGTH: 3
<212> TYPE: PRT
<213> ORGANISM: Artificial Sequence
<220> FEATURE:
<223> OTHER INFORMATION: G alpha t library linker sequence

<400> SEQUENCE: 151

Ser Trp Val
1

<210> SEQ ID NO 152
<211> LENGTH: 4
<212> TYPE: PRT
<213> ORGANISM: Artificial Sequence
<220> FEATURE:
<223> OTHER INFORMATION: G alpha t library linker sequence

<400> SEQUENCE: 152

Phe Val Asn Cys
1

<210> SEQ ID NO 153
<211> LENGTH: 4
<212> TYPE: PRT
<213> ORGANISM: Artificial Sequence
<220> FEATURE:
<223> OTHER INFORMATION: G alpha t library linker sequence

<400> SEQUENCE: 153

Glu Val Arg Arg
1

<210> SEQ ID NO 154
<211> LENGTH: 3
<212> TYPE: PRT
<213> ORGANISM: Artificial Sequence
<220> FEATURE:
<223> OTHER INFORMATION: G alpha t library linker sequence

<400> SEQUENCE: 154

Arg Val Gln
1

<210> SEQ ID NO 155
<211> LENGTH: 4
<212> TYPE: PRT
<213> ORGANISM: Artificial Sequence
<220> FEATURE:
<223> OTHER INFORMATION: G alpha t library linker sequence

<400> SEQUENCE: 155

Arg Leu Thr Arg
1

<210> SEQ ID NO 156
<211> LENGTH: 3
<212> TYPE: PRT
<213> ORGANISM: Artificial Sequence
<220> FEATURE:
<223> OTHER INFORMATION: G alpha t library linker sequence

<400> SEQUENCE: 156

Ser Arg Lys
1

<210> SEQ ID NO 157
<211> LENGTH: 4
<212> TYPE: PRT
<213> ORGANISM: Artificial Sequence
<220> FEATURE:
<223> OTHER INFORMATION: G alpha t library linker sequence

<400> SEQUENCE: 157

Met Thr His Ser
1

<210> SEQ ID NO 158
<211> LENGTH: 4
<212> TYPE: PRT
<213> ORGANISM: Artificial Sequence
<220> FEATURE:
<223> OTHER INFORMATION: G alpha t library linker sequence

<400> SEQUENCE: 158

Ser Gly Pro Gln
1

<210> SEQ ID NO 159
<211> LENGTH: 3
<212> TYPE: PRT
<213> ORGANISM: Artificial Sequence
<220> FEATURE:
<223> OTHER INFORMATION: G alpha t library linker sequence

<400> SEQUENCE: 159

Met Leu Asn
1

<210> SEQ ID NO 160
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 160

Leu Gln Arg Asn Lys Lys Gln Tyr Asn Leu Gly
1               5                   10

<210> SEQ ID NO 161
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 161

Leu Gln Leu Arg Tyr Lys Cys Tyr Asn Leu Val
1               5                   10

<210> SEQ ID NO 162
<211> LENGTH: 11
<212> TYPE: PRT
<213> ORGANISM: Artificial Sequence
<220> FEATURE:
<223> OTHER INFORMATION: G alpha t library pepetide

<400> SEQUENCE: 162

Val His Val Lys Leu Lys Glu Tyr Asn Leu Val

-continued 1               5               10

<210> SEQ ID NO 163
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 163

Leu Gln Leu Asn Val Lys Glu Tyr Asn Leu Val
1               5               10

<210> SEQ ID NO 164
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 164

Leu Arg Ile Tyr Leu Lys Gly Tyr Asn Leu Val
1               5               10

<210> SEQ ID NO 165
<211> LENGTH: 3
<212> TYPE: PRT
<213> ORGANISM: Artificial Sequence
<220> FEATURE:
<223> OTHER INFORMATION: G alpha 11 library linker sequence

<400> SEQUENCE: 165

Ser Ile Arg
1

<210> SEQ ID NO 166
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 166

Arg Trp Ile Val
1

<210> SEQ ID NO 167
<211> LENGTH: 3
<212> TYPE: PRT
<213> ORGANISM: Artificial Sequence
<220> FEATURE:
<223> OTHER INFORMATION: G alpha 11 library linker sequence

<400> SEQUENCE: 167

Gly Gly His
1

<210> SEQ ID NO 168
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 168

Arg Ser Glu Val
1

```
<210> SEQ ID NO 169
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 169

Cys Glu Pro Gly
1

<210> SEQ ID NO 170
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 170

His Gln Met Ala
1

<210> SEQ ID NO 171
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 171

Val Pro Ser Pro
1

<210> SEQ ID NO 172
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 172

Gln Met Pro Asn
1

<210> SEQ ID NO 173
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 173

Met Trp Pro Ser
1

<210> SEQ ID NO 174
<211> LENGTH: 3
<212> TYPE: PRT
<213> ORGANISM: Artificial Sequence
<220> FEATURE:
<223> OTHER INFORMATION: G alpha 11 library linker sequence

<400> SEQUENCE: 174

Cys Val Glu
1
```

```
<210> SEQ ID NO 175
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 175

Leu Gln Leu Asn Leu Lys Val Tyr Asn Leu Val
1               5                   10

<210> SEQ ID NO 176
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 176

Leu Glu Leu Asn Leu Lys Val Tyr Asn Leu Phe
1               5                   10

<210> SEQ ID NO 177
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 177

Leu His Leu Asn Met Ala Glu Val Ser Leu Val
1               5                   10

<210> SEQ ID NO 178
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 178

Leu Lys Arg Tyr Leu Lys Glu Ser Asn Leu Val
1               5                   10

<210> SEQ ID NO 179
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 179

Pro Arg Gln Leu
1

<210> SEQ ID NO 180
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 180

Phe Phe Trp Val
1
```

```
<210> SEQ ID NO 181
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 181

Gln Arg Asp Thr
1

<210> SEQ ID NO 182
<211> LENGTH: 4
<212> TYPE: PRT
<213> ORGANISM: Artificial Sequence
<220> FEATURE:
<223> OTHER INFORMATION: G alpha 11 library linker sequence

<400> SEQUENCE: 182

Asn Phe Arg Asn
1

<210> SEQ ID NO 183
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 183

Leu Gln Leu Lys Arg Gly Glu Tyr Ile Leu Val
1               5                   10

<210> SEQ ID NO 184
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 184

Cys Ser Leu Lys Leu Lys Ala Tyr Asn Leu Val
1               5                   10

<210> SEQ ID NO 185
<211> LENGTH: 11
<212> TYPE: PRT
<213> ORGANISM: Artificial Sequence
<220> FEATURE:
<223> OTHER INFORMATION: G alpha library peptide

<400> SEQUENCE: 185

Leu Gln Met Asn His Asn Glu Tyr Asn Leu Val
1               5                   10

<210> SEQ ID NO 186
<211> LENGTH: 11
<212> TYPE: PRT
<213> ORGANISM: Artificial Sequence
<220> FEATURE:
<223> OTHER INFORMATION: G alpha t library peptide

<400> SEQUENCE: 186

Pro Gln Leu Asn Leu Asn Ala Tyr Asn Leu Val
1               5                   10

<210> SEQ ID NO 187
```

```
<211> LENGTH: 11
<212> TYPE: PRT
<213> ORGANISM: Artificial Sequence
<220> FEATURE:
<223> OTHER INFORMATION: Gs library peptide

<400> SEQUENCE: 187

Gln Gly Met Gln Leu Arg Arg Phe Lys Leu Arg
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Gs library peptide

<400> SEQUENCE: 188

Arg Trp Leu His Trp Gln Tyr Arg Gly Arg Gly
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Gs library peptide

<400> SEQUENCE: 189

Pro Arg Pro Arg Leu Leu Arg Phe Lys Ile Pro
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Gs library peptide

<400> SEQUENCE: 190

Gln Gly Glu His Leu Arg Gln Leu Gln Leu Gln
1               5                   10

<210> SEQ ID NO 191
<211> LENGTH: 11
<212> TYPE: PRT
<213> ORGANISM: Artificial Sequence
<220> FEATURE:
<223> OTHER INFORMATION: Gs library peptide

<400> SEQUENCE: 191

Gln Arg Leu Arg Leu Gly Pro Asp Glu Leu Phe
1               5                   10

<210> SEQ ID NO 192
<211> LENGTH: 11
<212> TYPE: PRT
<213> ORGANISM: Artificial Sequence
<220> FEATURE:
<223> OTHER INFORMATION: Gs library peptide

<400> SEQUENCE: 192

Gln Arg Ile His Arg Arg Pro Phe Lys Phe Phe
1               5                   10

<210> SEQ ID NO 193
<211> LENGTH: 11
```

```
<212> TYPE: PRT
<213> ORGANISM: Artificial Sequence
<220> FEATURE:
<223> OTHER INFORMATION: Gs library peptide

<400> SEQUENCE: 193

Gln Arg Met Pro Leu Arg Leu Phe Glu Phe Leu
1               5                   10

<210> SEQ ID NO 194
<211> LENGTH: 11
<212> TYPE: PRT
<213> ORGANISM: Artificial Sequence
<220> FEATURE:
<223> OTHER INFORMATION: Gs library peptide

<400> SEQUENCE: 194

Gln Arg Val His Leu Arg Gln Asp Glu Leu Leu
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Gs library peptide

<400> SEQUENCE: 195

Asp Arg Met His Leu Trp Arg Phe Gly Leu Leu
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Gs library peptide

<400> SEQUENCE: 196

Gln Arg Met Pro Leu Arg Gln Tyr Glu Leu Leu
1               5                   10

<210> SEQ ID NO 197
<211> LENGTH: 11
<212> TYPE: PRT
<213> ORGANISM: Artificial Sequence
<220> FEATURE:
<223> OTHER INFORMATION: Gs library peptide

<400> SEQUENCE: 197

Gln Trp Met Asp Leu Arg Gln His Glu Leu Leu
1               5                   10

<210> SEQ ID NO 198
<211> LENGTH: 11
<212> TYPE: PRT
<213> ORGANISM: Artificial Sequence
<220> FEATURE:
<223> OTHER INFORMATION: Gs library peptide

<400> SEQUENCE: 198

Gln Arg Met Asn Leu Gly Pro Cys Gly Leu Leu
1               5                   10

<210> SEQ ID NO 199
<211> LENGTH: 11
<212> TYPE: PRT
```

```
<213> ORGANISM: Artificial Sequence
<220> FEATURE:
<223> OTHER INFORMATION: Gs library peptide

<400> SEQUENCE: 199

Asn Cys Met Lys Phe Arg Ser Cys Gly Leu Phe
1               5                   10

<210> SEQ ID NO 200
<211> LENGTH: 11
<212> TYPE: PRT
<213> ORGANISM: Artificial Sequence
<220> FEATURE:
<223> OTHER INFORMATION: Gs library peptide

<400> SEQUENCE: 200

Gln Arg Leu His Leu Arg Gly Tyr Glu Phe Leu
1               5                   10

<210> SEQ ID NO 201
<211> LENGTH: 11
<212> TYPE: PRT
<213> ORGANISM: Artificial Sequence
<220> FEATURE:
<223> OTHER INFORMATION: Gs library peptide

<400> SEQUENCE: 201

His Arg Arg His Ile Gly Pro Phe Ala Leu Leu
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Gs library peptide

<400> SEQUENCE: 202

Glu Arg Leu His Arg Arg Leu Phe Gln Leu His
1               5                   10

<210> SEQ ID NO 203
<211> LENGTH: 11
<212> TYPE: PRT
<213> ORGANISM: Artificial Sequence
<220> FEATURE:
<223> OTHER INFORMATION: Gs library peptide

<400> SEQUENCE: 203

Pro Cys Ile Gln Leu Gly Gln Tyr Glu Ser Phe
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Gs library peptide

<400> SEQUENCE: 204

Gln Arg Leu Arg Leu Arg Lys Tyr Arg Leu Phe
1               5                   10

<210> SEQ ID NO 205
<211> LENGTH: 11
<212> TYPE: PRT
<213> ORGANISM: Artificial Sequence
```

```
<220> FEATURE:
<223> OTHER INFORMATION: Gt library peptide

<400> SEQUENCE: 205

Ile Val Glu Ile Leu Glu Asp Cys Gly Leu Phe
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Gt library peptide

<400> SEQUENCE: 206

Met Leu Asp Asn Leu Lys Ala Cys Gly Leu Phe
1               5                   10

<210> SEQ ID NO 207
<211> LENGTH: 11
<212> TYPE: PRT
<213> ORGANISM: Artificial Sequence
<220> FEATURE:
<223> OTHER INFORMATION: Gt library peptide

<400> SEQUENCE: 207

Ile Leu Glu Asn Leu Lys Asp Cys Gly Leu Phe
1               5                   10

<210> SEQ ID NO 208
<211> LENGTH: 11
<212> TYPE: PRT
<213> ORGANISM: Artificial Sequence
<220> FEATURE:
<223> OTHER INFORMATION: Gt library peptide

<400> SEQUENCE: 208

Leu Arg Glu Asn Leu Lys Asp Cys Gly Leu Leu
1               5                   10

<210> SEQ ID NO 209
<211> LENGTH: 11
<212> TYPE: PRT
<213> ORGANISM: Artificial Sequence
<220> FEATURE:
<223> OTHER INFORMATION: Gt library peptide

<400> SEQUENCE: 209

Leu Leu Asp Ile Leu Lys Asp Cys Gly Leu Phe
1               5                   10

<210> SEQ ID NO 210
<211> LENGTH: 11
<212> TYPE: PRT
<213> ORGANISM: Artificial Sequence
<220> FEATURE:
<223> OTHER INFORMATION: Gt library peptide

<400> SEQUENCE: 210

Val Arg Asp Ile Leu Lys Asp Cys Gly Leu Phe
1               5                   10

<210> SEQ ID NO 211
<211> LENGTH: 11
<212> TYPE: PRT
<213> ORGANISM: Artificial Sequence
<220> FEATURE:
```

<223> OTHER INFORMATION: Gt library peptide

<400> SEQUENCE: 211

Ile Leu Glu Ser Leu Asn Glu Cys Gly Leu Phe
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Gt library sequence

<400> SEQUENCE: 212

Ile Leu Gln Asn Leu Lys Asp Cys Gly Leu Phe
1               5                   10

<210> SEQ ID NO 213
<211> LENGTH: 11
<212> TYPE: PRT
<213> ORGANISM: Artificial Sequence
<220> FEATURE:
<223> OTHER INFORMATION: Gt library sequence

<400> SEQUENCE: 213

Met Leu Asp Asn Leu Lys Asp Cys Gly Leu Phe
1               5                   10

<210> SEQ ID NO 214
<211> LENGTH: 11
<212> TYPE: PRT
<213> ORGANISM: Artificial Sequence
<220> FEATURE:
<223> OTHER INFORMATION: Gt library sequence

<400> SEQUENCE: 214

Ile His Asp Arg Leu Lys Asp Cys Gly Leu Phe
1               5                   10

<210> SEQ ID NO 215
<211> LENGTH: 11
<212> TYPE: PRT
<213> ORGANISM: Artificial Sequence
<220> FEATURE:
<223> OTHER INFORMATION: Gt library peptide

<400> SEQUENCE: 215

Ile Cys Glu Asn Leu Lys Asp Cys Gly Leu Phe
1               5                   10

<210> SEQ ID NO 216
<211> LENGTH: 11
<212> TYPE: PRT
<213> ORGANISM: Artificial Sequence
<220> FEATURE:
<223> OTHER INFORMATION: Gt library peptide

<400> SEQUENCE: 216

Ile Val Lys Asn Leu Glu Asp Cys Gly Leu Phe
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Gt library peptide

```
<400> SEQUENCE: 217

Ile Ser Lys Asn Leu Arg Asp Cys Gly Leu Leu
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Gt library peptide

<400> SEQUENCE: 218

Ile Arg Asp Asn Leu Lys Asp Cys Gly Leu Phe
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Gt library peptide

<400> SEQUENCE: 219

Ile Arg Glu Phe Leu Thr Asp Cys Gly Leu Phe
1               5                   10

<210> SEQ ID NO 220
<211> LENGTH: 11
<212> TYPE: PRT
<213> ORGANISM: Artificial Sequence
<220> FEATURE:
<223> OTHER INFORMATION: Gt library peptide

<400> SEQUENCE: 220

Ile Arg Leu Asp Leu Lys Asp Val Ser Leu Phe
1               5                   10

<210> SEQ ID NO 221
<211> LENGTH: 11
<212> TYPE: PRT
<213> ORGANISM: Artificial Sequence
<220> FEATURE:
<223> OTHER INFORMATION: Gt library sequence

<400> SEQUENCE: 221

Ile Cys Glu Arg Leu Asn Asp Cys Gly Leu Cys
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Gt library peptide

<400> SEQUENCE: 222

Pro Arg Asp Asn Thr Lys Val Arg Gly Leu Phe
1               5                   10

<210> SEQ ID NO 223
<211> LENGTH: 11
<212> TYPE: PRT
<213> ORGANISM: Artificial Sequence
<220> FEATURE:
<223> OTHER INFORMATION: Gt library peptide
```

<400> SEQUENCE: 223

Phe Trp Gly Asn Leu Gln Asp Ser Gly Leu Phe
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Gt library peptide

<400> SEQUENCE: 224

Arg Arg Gly Asn Gly Lys Asp Cys Arg His Phe
1               5                   10

<210> SEQ ID NO 225
<211> LENGTH: 11
<212> TYPE: PRT
<213> ORGANISM: Artificial Sequence
<220> FEATURE:
<223> OTHER INFORMATION: G12 library peptide

<400> SEQUENCE: 225

Leu Gln Glu Asn Leu Lys Glu Met Met Leu Gln
1               5                   10

<210> SEQ ID NO 226
<211> LENGTH: 11
<212> TYPE: PRT
<213> ORGANISM: Artificial Sequence
<220> FEATURE:
<223> OTHER INFORMATION: G12 library peptide

<400> SEQUENCE: 226

Leu Glu Glu Asn Leu Lys Tyr Arg Met Leu Asp
1               5                   10

<210> SEQ ID NO 227
<211> LENGTH: 11
<212> TYPE: PRT
<213> ORGANISM: Artificial Sequence
<220> FEATURE:
<223> OTHER INFORMATION: G12 library peptide

<400> SEQUENCE: 227

Leu Gln Glu Asp Leu Lys Gly Met Thr Leu Gln
1               5                   10

<210> SEQ ID NO 228
<211> LENGTH: 11
<212> TYPE: PRT
<213> ORGANISM: Artificial Sequence
<220> FEATURE:
<223> OTHER INFORMATION: G12 library peptide

<400> SEQUENCE: 228

Leu Gln Glu Thr Met Lys Asp Gln Ser Leu Gln
1               5                   10

<210> SEQ ID NO 229
<211> LENGTH: 11
<212> TYPE: PRT
<213> ORGANISM: Artificial Sequence
<220> FEATURE:
<223> OTHER INFORMATION: G12 library peptide

<400> SEQUENCE: 229

```
Pro Gln Val Asn Leu Lys Ser Ile Met Arg Gln
1               5                   10

<210> SEQ ID NO 230
<211> LENGTH: 11
<212> TYPE: PRT
<213> ORGANISM: Artificial Sequence
<220> FEATURE:
<223> OTHER INFORMATION: G12 library peptide

<400> SEQUENCE: 230

Trp Gln His Lys Leu Ser Glu Val Met Leu Gln
1               5                   10

<210> SEQ ID NO 231
<211> LENGTH: 11
<212> TYPE: PRT
<213> ORGANISM: Artificial Sequence
<220> FEATURE:
<223> OTHER INFORMATION: G12 library peptide

<400> SEQUENCE: 231

Leu Lys Glu His Leu Met Glu Arg Met Leu Gln
1               5                   10

<210> SEQ ID NO 232
<211> LENGTH: 11
<212> TYPE: PRT
<213> ORGANISM: Artificial Sequence
<220> FEATURE:
<223> OTHER INFORMATION: G12 library peptide

<400> SEQUENCE: 232

Leu Leu Gly Met Leu Glu Pro Leu Met Glu Gln
1               5                   10

<210> SEQ ID NO 233
<211> LENGTH: 11
<212> TYPE: PRT
<213> ORGANISM: Artificial Sequence
<220> FEATURE:
<223> OTHER INFORMATION: G13 library peptide

<400> SEQUENCE: 233

Leu Gln Asp Asn Leu Lys Gln Leu Met Leu Gln
1               5                   10

<210> SEQ ID NO 234
<211> LENGTH: 11
<212> TYPE: PRT
<213> ORGANISM: Artificial Sequence
<220> FEATURE:
<223> OTHER INFORMATION: G13 library peptide

<400> SEQUENCE: 234

Leu Gln Asp Asn Leu Arg His Leu Met Leu Gln
1               5                   10

<210> SEQ ID NO 235
<211> LENGTH: 11
<212> TYPE: PRT
<213> ORGANISM: Artificial Sequence
<220> FEATURE:
<223> OTHER INFORMATION: G13 library peptide

<400> SEQUENCE: 235
```

```
Leu Gln Asp Lys Ile Asn His Leu Met Leu Gln
1               5                   10

<210> SEQ ID NO 236
<211> LENGTH: 11
<212> TYPE: PRT
<213> ORGANISM: Artificial Sequence
<220> FEATURE:
<223> OTHER INFORMATION: G13 library peptide

<400> SEQUENCE: 236

Leu Gln Ala Asn Arg Lys Leu Gly Met Leu Gln
1               5                   10

<210> SEQ ID NO 237
<211> LENGTH: 11
<212> TYPE: PRT
<213> ORGANISM: Artificial Sequence
<220> FEATURE:
<223> OTHER INFORMATION: G13 library sequence

<400> SEQUENCE: 237

Leu Ile Val Lys Val Lys Gln Leu Ile Trp Gln
1               5                   10

<210> SEQ ID NO 238
<211> LENGTH: 11
<212> TYPE: PRT
<213> ORGANISM: Artificial Sequence
<220> FEATURE:
<223> OTHER INFORMATION: G13 library peptide

<400> SEQUENCE: 238

Met Arg Ala Lys Leu Asn Asn Leu Met Leu Glu
1               5                   10

<210> SEQ ID NO 239
<211> LENGTH: 10
<212> TYPE: PRT
<213> ORGANISM: Artificial Sequence
<220> FEATURE:
<223> OTHER INFORMATION: G13 library peptide

<400> SEQUENCE: 239

Leu Gln Asp Asn Leu Arg His Leu Ile Gln
1               5                   10

<210> SEQ ID NO 240
<211> LENGTH: 10
<212> TYPE: PRT
<213> ORGANISM: Artificial Sequence
<220> FEATURE:
<223> OTHER INFORMATION: G13 library peptide

<400> SEQUENCE: 240

Leu Gln Asp Asn Arg Asn Gln Leu Leu Phe
1               5                   10

<210> SEQ ID NO 241
<211> LENGTH: 11
<212> TYPE: PRT
<213> ORGANISM: Artificial Sequence
<220> FEATURE:
<223> OTHER INFORMATION: G11 library peptide

<400> SEQUENCE: 241

Leu Gln Leu Asn Arg Lys Asn Tyr Asn Leu Val
```

```
                1               5                   10
```

<210> SEQ ID NO 242
<211> LENGTH: 11
<212> TYPE: PRT
<213> ORGANISM: Artificial Sequence
<220> FEATURE:
<223> OTHER INFORMATION: G11 library peptide

<400> SEQUENCE: 242

```
Leu Gln Leu Asp Leu Lys Glu Ser Asn Met Val
1               5                   10
```

<210> SEQ ID NO 243
<211> LENGTH: 11
<212> TYPE: PRT
<213> ORGANISM: Artificial Sequence
<220> FEATURE:
<223> OTHER INFORMATION: G11 library peptide

<400> SEQUENCE: 243

```
Leu Gln Leu Asn Leu Lys Lys Tyr Asn Arg Val
1               5                   10
```

<210> SEQ ID NO 244
<211> LENGTH: 11
<212> TYPE: PRT
<213> ORGANISM: Artificial Sequence
<220> FEATURE:
<223> OTHER INFORMATION: G11 library peptide

<400> SEQUENCE: 244

```
Leu Gln Leu Arg Val Lys Glu Tyr Lys Arg Gly
1               5                   10
```

<210> SEQ ID NO 245
<211> LENGTH: 11
<212> TYPE: PRT
<213> ORGANISM: Artificial Sequence
<220> FEATURE:
<223> OTHER INFORMATION: G11 library peptide

<400> SEQUENCE: 245

```
Leu Gln Ile Tyr Leu Lys Gly Tyr Asn Leu Val
1               5                   10
```

<210> SEQ ID NO 246
<211> LENGTH: 11
<212> TYPE: PRT
<213> ORGANISM: Artificial Sequence
<220> FEATURE:
<223> OTHER INFORMATION: G11 library peptide

<400> SEQUENCE: 246

```
Leu Gln Tyr Asn Leu Lys Glu Ser Phe Val Val
1               5                   10
```

<210> SEQ ID NO 247
<211> LENGTH: 11
<212> TYPE: PRT
<213> ORGANISM: Artificial Sequence
<220> FEATURE:
<223> OTHER INFORMATION: G11 library peptide

<400> SEQUENCE: 247

```
Leu Gln Arg Asp His Val Glu Tyr Lys Leu Phe
1               5                   10
```

```
<210> SEQ ID NO 248
<211> LENGTH: 11
<212> TYPE: PRT
<213> ORGANISM: Artificial Sequence
<220> FEATURE:
<223> OTHER INFORMATION: G11 library peptide

<400> SEQUENCE: 248

Leu Val Ile Lys Pro Lys Glu Phe Asn Leu Val
1               5                   10

<210> SEQ ID NO 249
<211> LENGTH: 11
<212> TYPE: PRT
<213> ORGANISM: Artificial Sequence
<220> FEATURE:
<223> OTHER INFORMATION: G11 library peptide

<400> SEQUENCE: 249

Ile Gln Leu Asn Leu Lys Asn Tyr Asn Ile Val
1               5                   10

<210> SEQ ID NO 250
<211> LENGTH: 11
<212> TYPE: PRT
<213> ORGANISM: Artificial Sequence
<220> FEATURE:
<223> OTHER INFORMATION: G11 library peptide

<400> SEQUENCE: 250

Met Gln Leu Asn Leu Lys Glu Tyr Asn Leu Val
1               5                   10

<210> SEQ ID NO 251
<211> LENGTH: 11
<212> TYPE: PRT
<213> ORGANISM: Artificial Sequence
<220> FEATURE:
<223> OTHER INFORMATION: G11 library peptide

<400> SEQUENCE: 251

Val Gln Val Lys Leu Lys Glu Tyr Asn Leu Val
1               5                   10

<210> SEQ ID NO 252
<211> LENGTH: 11
<212> TYPE: PRT
<213> ORGANISM: Artificial Sequence
<220> FEATURE:
<223> OTHER INFORMATION: G11 library peptide

<400> SEQUENCE: 252

Gln Leu Leu Asn Gln Tyr Val Tyr Asn Leu Val
1               5                   10

<210> SEQ ID NO 253
<211> LENGTH: 11
<212> TYPE: PRT
<213> ORGANISM: Artificial Sequence
<220> FEATURE:
<223> OTHER INFORMATION: G11 library peptide

<400> SEQUENCE: 253

Trp Arg Leu Ser Leu Lys Val Tyr Asn Leu Val
1               5                   10
```

<210> SEQ ID NO 254
<211> LENGTH: 11
<212> TYPE: PRT
<213> ORGANISM: Artificial Sequence
<220> FEATURE:
<223> OTHER INFORMATION: G11 library peptide

<400> SEQUENCE: 254

Leu Gln Arg Asn Lys Asn Gln Tyr Asn Leu Gly
1               5                   10

<210> SEQ ID NO 255
<211> LENGTH: 11
<212> TYPE: PRT
<213> ORGANISM: Artificial Sequence
<220> FEATURE:
<223> OTHER INFORMATION: G11 library peptide

<400> SEQUENCE: 255

Leu Tyr Leu Asp Leu Lys Glu Tyr Cys Leu Phe
1               5                   10

<210> SEQ ID NO 256
<211> LENGTH: 11
<212> TYPE: PRT
<213> ORGANISM: Artificial Sequence
<220> FEATURE:
<223> OTHER INFORMATION: G11 library peptide

<400> SEQUENCE: 256

Ser Ala Lys Glu Leu Asp Gln Tyr Asn Leu Gly
1               5                   10

<210> SEQ ID NO 257
<211> LENGTH: 11
<212> TYPE: PRT
<213> ORGANISM: Artificial Sequence
<220> FEATURE:
<223> OTHER INFORMATION: G11 library peptide

<400> SEQUENCE: 257

Leu Phe Leu Asn Leu Lys Glu Tyr Ser Leu Val
1               5                   10

<210> SEQ ID NO 258
<211> LENGTH: 11
<212> TYPE: PRT
<213> ORGANISM: Artificial Sequence
<220> FEATURE:
<223> OTHER INFORMATION: G11 library peptide

<400> SEQUENCE: 258

Leu Glu Leu Asn Leu Lys Val Tyr Asn Leu Val
1               5                   10

<210> SEQ ID NO 259
<211> LENGTH: 11
<212> TYPE: PRT
<213> ORGANISM: Artificial Sequence
<220> FEATURE:
<223> OTHER INFORMATION: G11 library peptide

<400> SEQUENCE: 259

Leu Pro Leu Asn Leu Ile Asp Phe Ser Leu Met
1               5                   10

```
<210> SEQ ID NO 260
<211> LENGTH: 11
<212> TYPE: PRT
<213> ORGANISM: Artificial Sequence
<220> FEATURE:
<223> OTHER INFORMATION: G11 library peptide

<400> SEQUENCE: 260

Leu Pro Arg Asn Leu Lys Glu Tyr Asp Leu Gly
1               5                   10

<210> SEQ ID NO 261
<211> LENGTH: 11
<212> TYPE: PRT
<213> ORGANISM: Artificial Sequence
<220> FEATURE:
<223> OTHER INFORMATION: G11 library peptide

<400> SEQUENCE: 261

Leu Arg Leu Asn Asp Ile Glu Ala Leu Leu Val
1               5                   10

<210> SEQ ID NO 262
<211> LENGTH: 11
<212> TYPE: PRT
<213> ORGANISM: Artificial Sequence
<220> FEATURE:
<223> OTHER INFORMATION: G11 library peptide

<400> SEQUENCE: 262

Leu Val Leu Asn Arg Ile Glu Tyr Asn Leu Leu
1               5                   10

<210> SEQ ID NO 263
<211> LENGTH: 11
<212> TYPE: PRT
<213> ORGANISM: Artificial Sequence
<220> FEATURE:
<223> OTHER INFORMATION: G11 library peptide

<400> SEQUENCE: 263

Leu Lys Arg Lys Leu Lys Glu Ser Asn Met Gly
1               5                   10

<210> SEQ ID NO 264
<211> LENGTH: 11
<212> TYPE: PRT
<213> ORGANISM: Artificial Sequence
<220> FEATURE:
<223> OTHER INFORMATION: G11 library peptide

<400> SEQUENCE: 264

Leu Lys Arg Lys Val Lys Glu Tyr Asn Leu Gly
1               5                   10

<210> SEQ ID NO 265
<211> LENGTH: 19
<212> TYPE: DNA
<213> ORGANISM: Artificial Sequence
<220> FEATURE:
<223> OTHER INFORMATION: Reverse primer

<400> SEQUENCE: 265
gaaaatcttc tctcatccg                                              19

<210> SEQ ID NO 266
<211> LENGTH: 11
```

```
<212> TYPE: PRT
<213> ORGANISM: Artificial Sequence
<220> FEATURE:
<223> OTHER INFORMATION: Gt library peptide

<400> SEQUENCE: 266

Ile Leu Glu Asn Leu Lys Asp Cys Gly Leu Leu
1               5                   10

<210> SEQ ID NO 267
<211> LENGTH: 11
<212> TYPE: PRT
<213> ORGANISM: Artificial Sequence
<220> FEATURE:
<223> OTHER INFORMATION: Gt library peptide

<400> SEQUENCE: 267

Leu Gln Gln Val Leu Lys Asp Cys Gly Leu Leu
1               5                   10

<210> SEQ ID NO 268
<211> LENGTH: 11
<212> TYPE: PRT
<213> ORGANISM: Artificial Sequence
<220> FEATURE:
<223> OTHER INFORMATION: Gt library peptide

<400> SEQUENCE: 268

Leu Leu Glu Asn Leu Arg Asp Cys Gly Met Ile
1               5                   10

<210> SEQ ID NO 269
<211> LENGTH: 9
<212> TYPE: DNA
<213> ORGANISM: Homo sapiens

<400> SEQUENCE: 269 gccgccacc                                                              9

<210> SEQ ID NO 270
<211> LENGTH: 57
<212> TYPE: DNA
<213> ORGANISM: Artificial Sequence
<220> FEATURE:
<223> OTHER INFORMATION: Gi alpha 1/2 carboxy terminal sequence
      oligonucleotide

<400> SEQUENCE: 270
gatccgccgc caccatggga atcaagaaca acctgaagga ctgcggcctc ttctgaa       57

<210> SEQ ID NO 271
<211> LENGTH: 57
<212> TYPE: DNA
<213> ORGANISM: Artificial Sequence
<220> FEATURE:
<223> OTHER INFORMATION: complementary strand to Gi alpha 1/2
      oligonucleotide

<400> SEQUENCE: 271
agctttcaga agaggccgca gtccttcagg ttgttcttga ttcccatggt ggcggcg       57

<210> SEQ ID NO 272
<211> LENGTH: 19
<212> TYPE: DNA
<213> ORGANISM: Artificial Sequence
<220> FEATURE:
```

-continued

```
<223> OTHER INFORMATION: forward primer for G alpha carboxyl terminal
      peptide insert

<400> SEQUENCE: 272
atccgccgcc accatggga                                                    19

<210> SEQ ID NO 273
<211> LENGTH: 20
<212> TYPE: DNA
<213> ORGANISM: Artificial Sequence
<220> FEATURE:
<223> OTHER INFORMATION: reverse primer for G alpha carboxyl terminal
      peptide insert

<400> SEQUENCE: 273
gcgaaaggag cggggcgcta                                                   20
```